United States Patent
Pillarsetty et al.

(10) Patent No.: US 11,633,502 B2
(45) Date of Patent: Apr. 25, 2023

(54) BONE MARROW-, RETICULOENDOTHELIAL SYSTEM-, AND/OR LYMPH NODE-TARGETED RADIOLABELED LIPOSOMES AND METHODS OF THEIR DIAGNOSTIC AND THERAPEUTIC USE

(71) Applicant: Memorial Sloan Kettering Cancer Center, New York, NY (US)

(72) Inventors: Naga Vara Kishore Pillarsetty, Jackson Heights, NY (US); Steven M. Larson, New York, NY (US); Sang-gyu Lee, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 16/080,823

(22) PCT Filed: Mar. 7, 2017

(86) PCT No.: PCT/US2017/021092
§ 371 (c)(1),
(2) Date: Aug. 29, 2018

(87) PCT Pub. No.: WO2017/155948
PCT Pub. Date: Sep. 14, 2017

(65) Prior Publication Data
US 2019/0298853 A1     Oct. 3, 2019

Related U.S. Application Data

(60) Provisional application No. 62/304,814, filed on Mar. 7, 2016.

(51) Int. Cl.
*A61K 47/60*    (2017.01)
*A61K 47/54*    (2017.01)
(Continued)

(52) U.S. Cl.
CPC .......... *A61K 47/6911* (2017.08); *A61K 47/50* (2017.08); *A61K 47/547* (2017.08);
(Continued)

(58) Field of Classification Search
CPC ...... A61K 45/06; A61K 47/50; A61K 47/547; A61K 47/60; A61K 47/6911; A61P 7/00;
(Continued)

(56) References Cited

U.S. PATENT DOCUMENTS 5,013,556 A * 5/1991 Woodle .................... A61P 35/00
                                                424/450
7,060,689 B2 * 6/2006 Goins ................. A61K 47/6898
                                                514/44 R (Continued)

FOREIGN PATENT DOCUMENTS

JP      2000-198731 A    7/2000
WO    WO-91/05546 A1    5/1991
(Continued)

OTHER PUBLICATIONS

Shahid et al Effect of saline and non-specific insulin binding on the phase behavior of PEG-grafted phosphoethanolamine-succinyl model membranes, a Dissertation, 2013 (Year: 2013).*

(Continued)

*Primary Examiner* — Adam C Milligan
*Assistant Examiner* — Amanda Michelle Petritsch
(74) *Attorney, Agent, or Firm* — Choate, Hall & Stewart LLP; William R. Haulbrook; Samuel R. Polio

(57) ABSTRACT

Described herein are liposome-based nanocarriers that selectively target bone marrow, minimize tumor delivery, and maintain high drug concentrations in bone marrow when compared to conventional systemic delivery. The composition of the liposome-based nanocarriers may also be tuned to selectively target lymph nodes and other reticuloendothelial (Continued)

system organs (e.g., spleen, e.g., liver). Also described herein are methods of imaging and mapping the bone marrow and/or other reticuloendothelial system organs using the described liposome-based nanocarriers. These methods provide high resolution non-invasive and quantitative imaging via PET, which offers advantages over conventional imaging/tracking methods. Furthermore, in certain embodiments, the liposome-based carriers are used to stabilize and deliver radioprotectant/free radical scavenger drugs to the bone marrow, thereby protecting the bone marrow from subsequent radiation exposure, thereby limiting the adverse impact of radiation exposure on the individual.

34 Claims, 35 Drawing Sheets

(51) Int. Cl.
    *A61P 35/04*     (2006.01)
    *A61K 47/50*     (2017.01)
    *A61K 45/06*     (2006.01)
    *A61K 47/69*     (2017.01)

(52) U.S. Cl.
    CPC .............. *A61K 47/60* (2017.08); *A61P 35/04* (2018.01); *A61K 45/06* (2013.01)

(58) Field of Classification Search
    CPC .......... A61P 19/10; A61P 31/04; A61P 35/00; A61P 35/02; A61P 35/04; A61P 43/00
    See application file for complete search history.

(56) References Cited

U.S. PATENT DOCUMENTS

| | | | |
|---|---|---|---|
| 8,962,015 B2* | 2/2015 | Lau | A61K 9/1277 424/450 |
| 10,307,491 B2* | 6/2019 | Moon | A61K 9/1271 |
| 2003/0129223 A1 | 7/2003 | Wartchow et al. | |
| 2003/0133972 A1 | 7/2003 | Danthi et al. | |
| 2009/0081121 A1 | 3/2009 | Ting et al. | |
| 2013/0204121 A1* | 8/2013 | Andresen | A61B 6/037 600/411 |
| 2015/0202336 A1* | 7/2015 | Petersen | C07B 59/00 424/1.29 |
| 2015/0343100 A1* | 12/2015 | Perez-Medina | A61K 49/0032 424/1.21 |
| 2022/0023450 A1 | 1/2022 | Pillarsetty et al. | |

FOREIGN PATENT DOCUMENTS

| | | |
|---|---|---|
| WO | WO-98/18450 A1 | 5/1998 |
| WO | WO-2004/070009 A2 | 8/2004 |
| WO | WO-2008/130137 A1 | 10/2008 |
| WO | WO-2011/006510 A1 | 1/2011 |
| WO | WO-2015/183876 A1 | 12/2015 |
| WO | WO-2016/191556 A1 | 12/2016 |
| WO | WO-2017/155948 A1 | 9/2017 |
| WO | WO-2020/055929 A1 | 3/2020 |

OTHER PUBLICATIONS

Jonah et al (Biochimica et Biophysica Acta, 401, 1975, 336-348) (Year: 1975).*
Citrin et al (The Oncologist, 2010, 15, 360-371). (Year: 2010).*
Mann et al (The University of Texas MD Anderson Cancer Center UT Health Graduate School of Biomedical Sciences Dissertations and Theses, Open Access, 158, 2011). (Year: 2011).*
Abra, R. M. and Hunt, C.A., Liposome disposition in vivo, III. Dose and vesicle-size effects, Biochimica et biophysica acta, 666:493-503, (1981).
Berbee, M. et al., gamma-Tocotrienol ameliorates intestinal radiation injury and reduces vascular oxidative stress after total-body irradiation by an HMG-CoA reductase-dependent mechanism, Radiat Res, 171:596-605, (2009).
Cao, X. et al., Irradiation induces bone injury by damaging bone marrow microenvironment for stem cells, Proc Natl Acad Sci USA. 108:1609-1614, (2011).
Cho, O. et al., Prognostic Value of Severe Lymphopenia During Pelvic Concurrent Chemoradiotherapy in Cervical Cancer, Anticancer Res, 36:3541-3547, (2016).
Chow, C.K. and Draper, H.H., Isolation of gamma-tocotrienol dimers from Hevea latex, Biochemistry, 9:445-450, (1970).
Chowdhary, R.K. et al., Drug release characteristics of lipid based benzoporphyrin derivative, J Pharm Pharm Sci, 6:13-19, (2003).
Citrin, D. et al., Radioprotectors and Mitigators of Radiation-Induced Normal Tissue Injury, The Oncologist, 15:360-371, (2010).
Cucinotta, F.A. et al., How safe is safe enough? Radiation risk for a human mission to Mars, PloS one, 8:074988, (2013).
Cucinotta, F.A., Space radiation risks for astronauts on multiple International Space Station missions, PloS one, 9:e96099, (2014).
Danhier, F., To exploit the tumor microenvironment: Since the EPR effect fails in the clinic, what is the future of nanomedicine?, Journal of controlled release : official journal of the Controlled Release Society, 244:108-121, (2016).
Davis, T.A. et al., Subcutaneous administration of genistein prior to lethal irradiation supports multilineage, hematopoietic progenitor cell recovery and survival, International journal of radiation biology,83:141-151 (2007).
Dawson, L.A. and Sharpe, M.B., Image-guided radiotherapy: rationale, benefits, and limitations, The Lancet. Oncology, 7:848-858, (2006).
Fetterly, G.J. and Straubinger, R.M., Pharmacokinetics of paclitaxel-containing liposomes in rats, AAPS PharmSci, 5:E32, (2003).
Gabizon, A. et al., Pharmacokinetics of pegylated liposomal Doxorubicin: review of animal and human studies, Clin Pharmacokinet, 42:419-436, (2003).
Galli, F. et al., The effect of alpha- and gamma-tocopherol and their carboxyethyl hydroxychroman metabolites on prostate cancer cell proliferation, Arch Biochem Biophys, 423:97-102 (2004).
Ghosh, S.P. et al., Gamma-tocotrienol, atocol antioxidant as a potent radioprotector, International journal of radiation biology, 85:598-606, (2009).
Gould, M.N. et al., A comparison of tocopherol and tocotrienol for the chemoprevention of chemically induced rat mammary tumors, Am J Clin Nutr, 53:1068S-1070S, (1991).
Guthrie, N. et al., Inhibition of proliferation of estrogen receptor-negative MDA-MB-435 and -positive MCF-7 human breast cancer cells by palm oil tocotrienols and tamoxifen, alone and in combination, J Nutr, 127:544S-548S, (1997).
Jaffray, D.A., Image-guided radiotherapy: from current concept to future perspectives, Nature reviews, Clinical oncology, 9:688-699, (2012).
Jordan, B.R., The Hiroshima/Nagasaki Survivor Studies: Discrepancies Between Results and General Perception, Genetics, 203:1505-1512, (2016).
Kumar, K.S. et al., Preferential radiation sensitization of prostate cancer in nude mice by nutraceutical antioxidant gamma-tocotrienol, Life Science, 78:2099-2104, (2006).
Liu, D. et al., Liposome clearance from blood: different animal species have different mechanisms, Biochimica et biophysica acta, 1240:277-284, (1995).
Liu, L.T. et al., The Prognostic Value of Treatment-Related Lymphopenia in Nasopharyngeal Carcinoma Patients, Cancer Res Treat, 50:19-29, (2018).
Loening, A.M. and Gambhir, S.S., Amide: a free software tool for multimodality medical image analysis, Molecular imaging, 2:131-137, (2003).
MacManus, M. et al., Radiotherapy-associated neutropenia and thrombocytopenia: analysis of risk factors and development of a predictive model, Blood, 89:2303-2310, (1997).
Moding, E.J. et al., Strategies for optimizing the response of cancer and normal tissues to radiation, Nature reviews, Drug discovery, 12:526-542, (2013).

(56) References Cited

OTHER PUBLICATIONS

Murry, D.J. and Blaney, S.M., Clinical pharmacology of encapsulated sustained-release cytarabine, Ann Pharmacother, 34:1173-1178 (2000).
Nelp, W.B. et al., Distribution of the erythron and the RES in the bone marrow organ, Journal of nuclear medicine: official publication, Society of Nuclear Medicine, 8:430-436, (1967).
Nelp, W.B. et al., Long-term effects of local irradiation of the marrow on erythron and red cell function, Blood, 36:617-622, (1970).
Parker, C. et al., Alpha emitter radium-223 and survival in metastatic prostate cancer, The New England Journal of Medicine, 369:213-223, (2013).
Pathak, R. et al., The Vitamin E Analog Gamma-Tocotrienol (GT3) Suppresses Radiation-Induced Cytogenetic Damage, Pharm Res, 33:2117-2125, (2016).
Preston, D.L. et al., Effect of recent changes in atomic bomb survivor dosimetry on cancer mortality risk estimates, Radiat Res, 162:377-389, (2004).
Ray, S. et al., Mobilization of progenitor cells into peripheral blood by gamma-tocotrienol: a promising radiation countermeasure, Int Immunopharmacol, 15:557-564, (2013).
Singh, V.K. et al., A review of radiation countermeasures focusing on injury-specific medicinals and regulatory approval status: part II. Countermeasures for limited indications, internalized radionuclides, emesis, late effects, and agents demonstrating efficacy in large animals with or without FDA IND status, International Journal of Radiation Biology, 93:870-884, (2017).
Singh, V.K. et al., Medical countermeasures for unwanted CBRN exposures: part II radiological and nuclear threats with review of recent countermeasure patents, Expert Opin Ther Pat, 26:1399-1408, (2016).
Sou, K. et al., Bone marrow-targeted liposomal carriers, Expert opinion on drug delivery, 8:317-328, (2011).
Srivastava, J.K. and Gupta, S., Tocotrienol-rich fraction of palm oil induces cell cycle arrest and apoptosis selectively in human prostate cancer cells, Biochemical and biophysical research communications, 346:447-453, (2006).
Strosberg, J. et al., Phase 3 Trial of (177)Lu-Dotatate for Midgut Neuroendocrine Tumors, The New England Journal of Medicine, 376:125-135, (2017).
Wada,S. et al., Tumor suppressive effects of tocotrienol in vivo and in vitro, Cancer Letter, 229:181-191, (2005).
Yu, W. et al., Induction of apoptosis in human breast cancer cells by tocopherols and tocotrienols,. Nutr Cancer, 33:26-32, (1999).
Zhang, J.A. et al., Development and characterization of a novel Cremophor EL free liposome-based paclitaxel (LEP-ETU) formulation, Eur J Pharm Biopharm, 59:177-187, (2005).
Al-Jamal, W.T. and Kostarelos, K., Liposomes: From a Clinically Established Drug Delivery System to a Nanoparticle Platform for Theranostic Nanomedicine, Accounts of Chemical Research. 44(10):1094-1104 (2011).
Awasthi, V. D. et al., Neutral and Anionic Liposome-Encapsulated Hemoglobin: Effect of Postinserted Poly(ethylene glycol)-distearoylphosphatidylethanolamine on Distribution and Circulation Kinetics, The Journal of Pharmacology and Experiemental Therapeutics, 309(1):241-248 (2004).
Brahmamdam, P. et al., Targeted Delivery of siRNA to Cell Death Proteins in Sepsis, Shock, 32(2):131-139 (2009).
Chang, H.I and Yeh, M.K., Clinical development of liposome-based drugs: formulation, characterization, and therapeutic efficacy, International Journal of Nanomedicine, 7:49-60 (2012).
Dawidczyk, C.M. et al., State-of-the-art in design rules for drug delivery platforms: Lessons learned from FDA-approved nanomedicines, Journal of Controlled Release, 187:133-144 (2014).
Herrera-Carrillo, E. and Berkhout, B., Bone Marrow Gene therapy for HIV/AIDS, Viruses, 7(7):3910-3936 (2015), ISSN 1999-4915.
International Search Report, PCT/US2017/021092 (Bone Marrow-, Reticuloendothelial System-, and/or Lymph Node-Targeted Radiolabeled Liposomes and Methods of Their Diagnostic and Therapeutic Use, filed Mar. 7, 2017), issued by ISA/European Patent Office, 5 pages, dated May 31, 2017.
Khawar, I.A. et al., Improving drug delivery to solid tumors: Priming the tumor microenvironment, Journal of Controlled Release, 201:78-89 (2015).
Kouvaris, J.R. et al., Amifostine: The First Selective-Target and Broad-Spectrum Radioprotector, The Oncologist, 12(6):738-747 (2007).
Lee, S. et al., Copper-64 labeled liposomes for imaging bone marrow, Nuclear Medicine and Biology 43:781-787 (2016).
Luk, B.T. et al., Lipid- and Polymer-Based Nanostructures for Cancer Theranostics, Theranostics, 2(12):1117-1126 (2012).
Mabro, M. et al., A Risk-Benefit Assessment of Amifostine in Cytoprotection, Drug Safety, 21(5):367-387 (1999).
Porter, C.J. et al., The polyoxyethylene/polyoxypropylene block co-polymer poloxamer-407 selectively redirects intravenously injected microspheres to sinusoidal endothelial cells of rabbit bone marrow, FEBS Letters, 305(1):62-69 (1992).
Pradeep, S. et al., Erythropoietin Stimulates Tumor Growth via EphB4, Cancer Cell, 28(5):610-622 (2015).
Puhalla, S. et al., Hematopoietic growth factors: Personalization of Risks and Benefits, Molecular Oncology 6(2):237-241 (2012).
Schettini, D. A. et al., Improved targeting of antimony to the bone marrow of dogs using liposomes of reduced size, International Journal of Pharmaceutics, 315:140-147 (2006).
Sou, K. et al., Bone marrow-targeted liposomal carriers, Expert Opinion on Drug Delivery, 8(3):317-328 (2011).
Sou, K. et al., Selective uptake of surface-modified phospholipid vesicles by bone marrow macrophages in vivo, Biomaterials, 28:2655-2666 (2007).
Tardi, P. et al., Passive and semi-active targeting of bone marrow and leukemia cells using anionic low cholesterol liposomes, Jounral of Drug Targeting, 24(9):797-804 (2016).
Written Opinion, PCT/US2017/021092 (Bone Marrow-, Reticuloendothelial System-, and/or Lymph Node-Targeted Radiolabeled Liposomes and Methods of Their Diagnostic and Therapeutic Use, filed Mar. 7, 2017), issued by ISA/European Patent Office, 10 pages, dated May 31, 2017.
Ahl, P.L. et. al., Enhancement of the in vivo circulation of lifetime of L-α-distearoylphosphatidylcholine liposomes: importance of liposomal aggregation versus complement opsonization, Biochimica et Biophysica Acta, 1329:370-382, (1997).
Moribe, K et. al., Estimation of Surface State of Poly(ethylene glycol)-Coated Liposomes Using an Aqueous Two-Phase Partitioning Technique, Chem. Pharm. Bull. 45(10):1683-1687, (1997).

\* cited by examiner

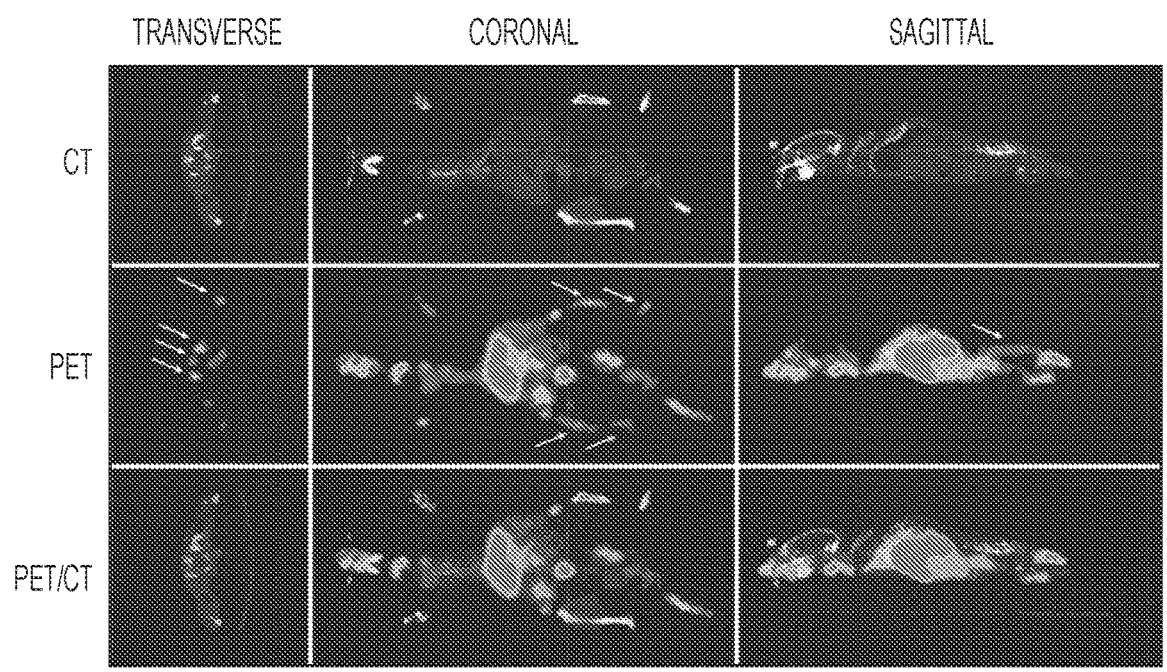
FIG. 4A
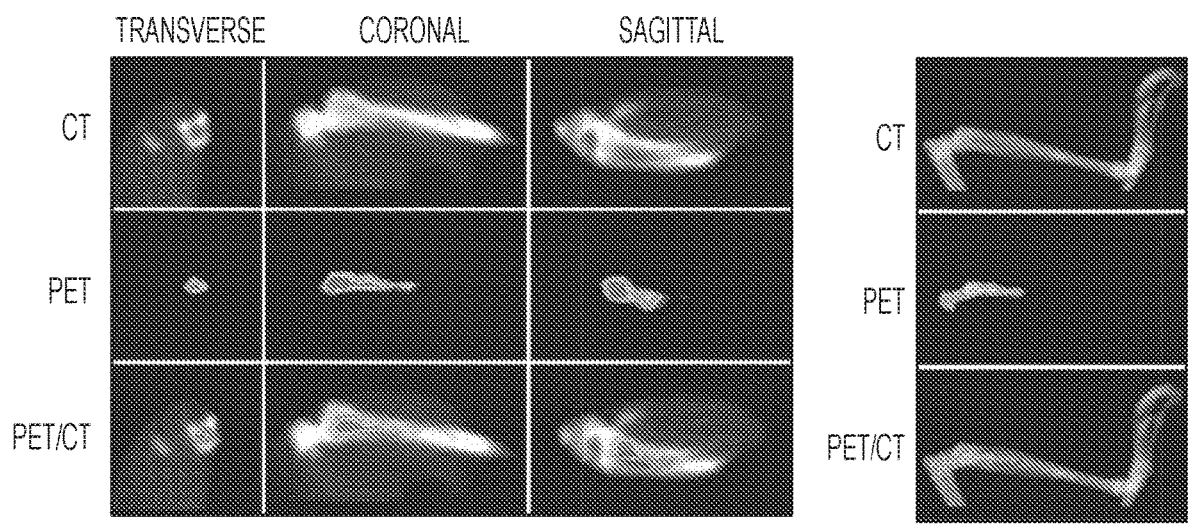
FIG. 4B                    FIG. 4C

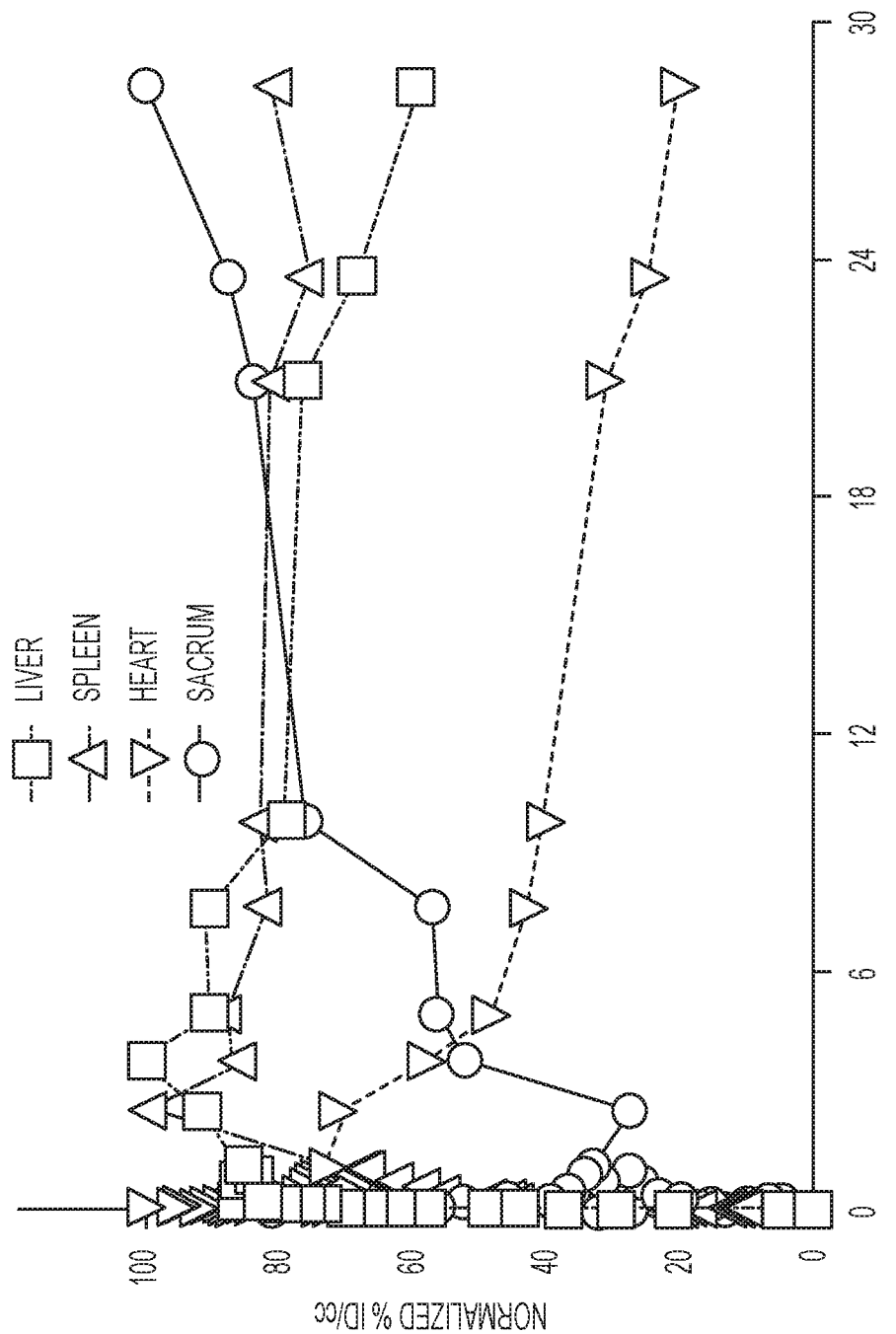

LYMPH NODE TARGETING LIPOSOME

BONE MARROW TARGETING LIPOSOME

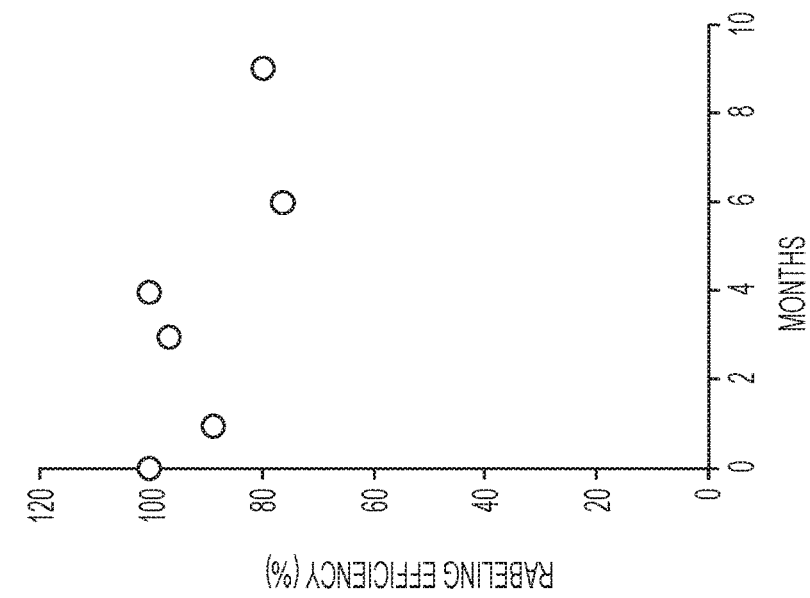
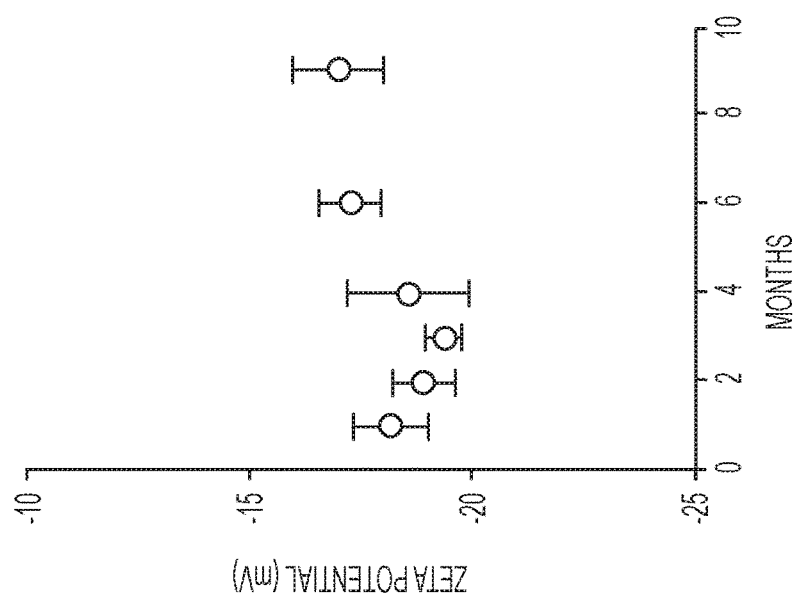
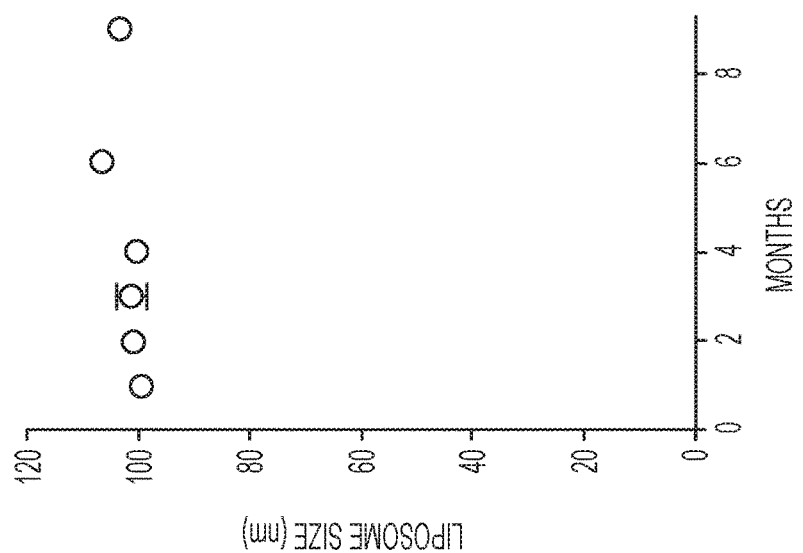

1,2-DIOLEOYL-sn-GLYCERO-3-PHOSPHOETHANOLAMINE (DOPE)

1,2-DIOLEOYL-3-TRIMETHYLAMMONIUM-PROPANE (DOTAP)

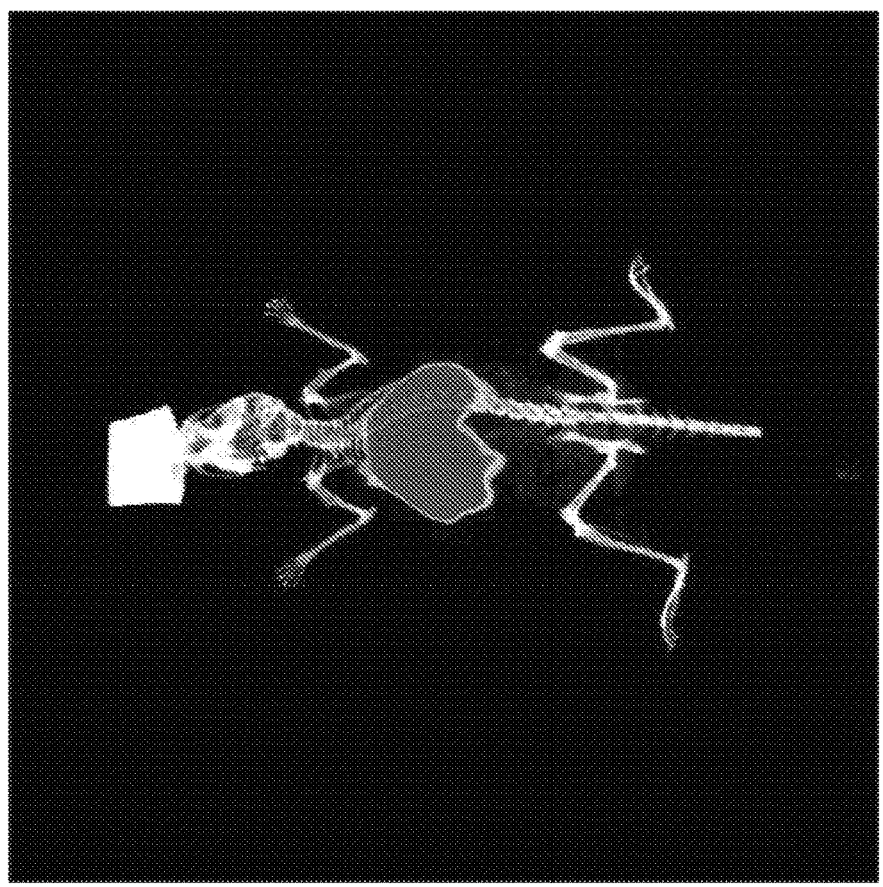
FIG. 22B POSITIVELY CHARGE LIPOSOME w/ 1% PEG
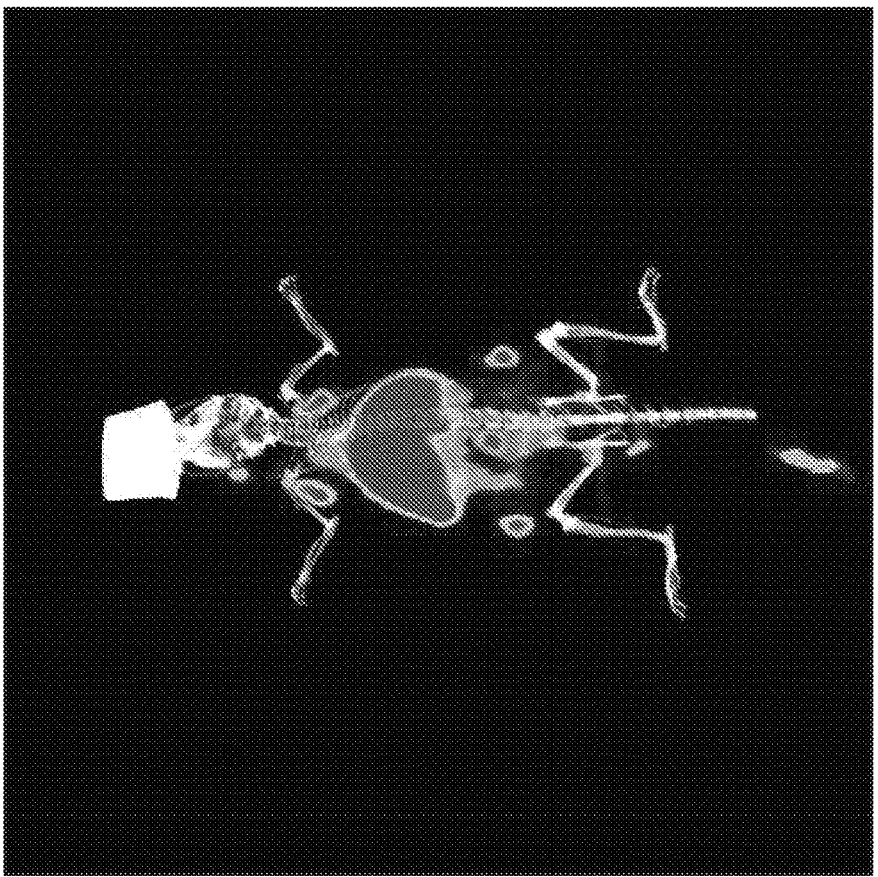
FIG. 22A NEGATIVELY CHARGE LIPOSOME w/ 1% PEG

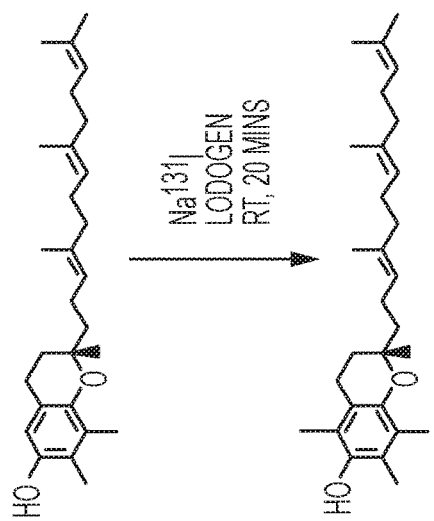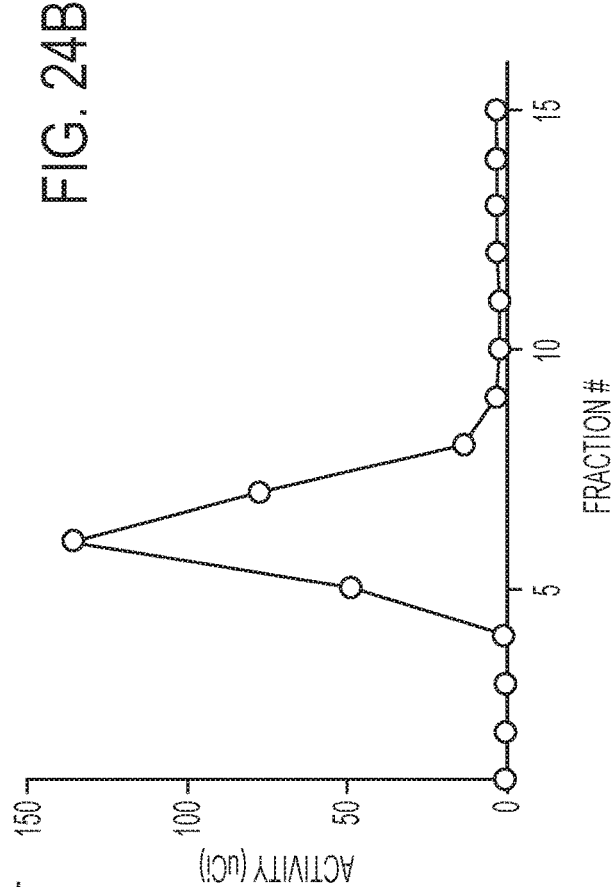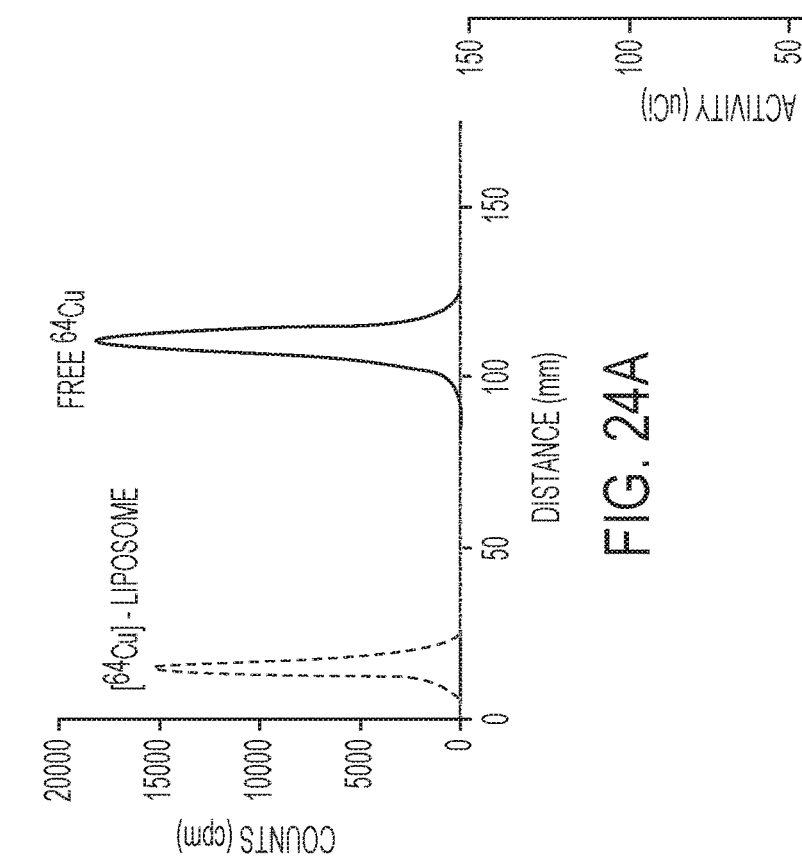
FIG. 24B
FIG. 24C
FIG. 24A

BONE MARROW-, RETICULOENDOTHELIAL SYSTEM-, AND/OR LYMPH NODE-TARGETED RADIOLABELED LIPOSOMES AND METHODS OF THEIR DIAGNOSTIC AND THERAPEUTIC USE

CROSS-REFERENCE TO RELATED APPLICATION

This application claims the benefit of U.S. Application Ser. No. 62/304,814 filed on Mar. 7, 2016, the disclosure of which is hereby incorporated by reference in its entirety.

GOVERNMENT SUPPORT

This invention was made with government support under grant number CA086438 awarded by National Institutes of Health (NIH). The government has certain rights in the invention.

FIELD OF THE INVENTION

This invention relates generally to radiolabeled liposomes for image guided drug delivery to target tissue, e.g., bone marrow, the reticuloendothelial system, and/or lymph nodes. In particular embodiments, the invention relates to PET-traceable liposomal nanocarriers for imaging tissue, e.g., bone marrow, lymph nodes, and other organs of the reticuloendothelial system and preferential delivery of drugs/agents to target tissue in healthy or tumor bearing animals (e.g., humans).

BACKGROUND

The reticuloendothelial system is a network of cells and tissues found in the body, for example, in the spleen, liver, lungs, bone marrow and lymph nodes. The reticuloendothelial cells of the spleen possess the ability to dispose of disintegrated erythrocytes. The reticuloendothelial cells located in the blood cavities of the liver are called Kupffer cells. These cells, together with the cells of the general connective tissue and bone marrow, are capable of transforming into bile pigment the hemoglobin released by disintegrated erythrocytes.

Bone marrow is a soft cellular component found inside bones and comprises hematopoietic and stromal stem cells in adipocyte-rich and highly-vascularized environments. Bone marrow components are responsible for several important functions including maintenance of hematopoiesis, immune balance, bone integrity, energy metabolism, etc. Accordingly, bone marrow plays a critical role in the survival and maintenance of the body.

The dynamic and proliferative nature of the bone marrow makes it highly sensitive to chemotherapeutic agents, radiation, and other drugs. Therefore, a common side effect of treating cancer patients with drugs or radiation is bone marrow depletion or bone marrow suppression (BMS). BMS results from destruction of resident and circulating hematopoietic stem cells (HSCs) and differentiated daughter cells, including radiation sensitive lymphocytes. This can lead to potentially lethal complications such as anemia, neutropenia, and thrombocytopenia. BMS can cause treatment delays, additional hospitalizations, and severely limit aggressive interventions that can potentially eradicate the disease.

A major challenge in using radioprotective agents in radiation therapy settings is the unintentional delivery of the radioprotectant to the tumor. This can result in decreased overall efficacy of the treatment protocol and reduced effect in abrogating the tumor. To this end, selective and adequate drug delivery via systemic administration to human bone marrow has been shown to stimulate specific marrow elements optimally and provide radioprotection during radiotherapy. However, these methods require drugs to be administered in high concentrations in order to deliver pharmacologically relevant doses to marrow. Further, because there is often a short time window of optimal pharmacologic effects, dosing must be frequently repeated. This method also often leads to increased drug delivery to the non-target tissues including tumor tissue and can lead to unfavorable consequences.

As described above, targeted drug delivery to the bone marrow is challenging because high concentrations or repeated administrations are needed to ensure maintenance of cytoprotective concentrations of drugs are in the marrow during the procedures. This is especially true for molecules with short blood half-lives such as Amifostine® that is used for reducing bone marrow suppression (BMS) during radiation therapy and chemotherapy (Mabro, M., S. Faivre, and E. Raymond, *A risk-benefit assessment of amifostine in cytoprotection*. Drug Saf, 1999. 21(5): p. 367-87; Kouvaris, J. R., V. E. Kouloulias, and L. J. Vlahos, *Amifostine: the first selective-target and broad-spectrum radioprotector*. Oncologist, 2007. 12(6): p. 738-47). However, improving biological half-life is not a viable solution on its own, as this can potentially lead to increased delivery to the tumor sites and thus reduce overall efficacy of the treatment (chemo- or radiotherapy) protocol (Puhalla, S., S. Bhattacharya, and N. E. Davidson, *Hematopoietic growth factors: personalization of risks and benefits*. Mol Oncol, 2012. 6(2): p. 237-41).

Liposomal nanocarriers have been shown to modify the pharmacokinetic and delivery behavior of tested/approved drugs for tumors without the need for rediscovering new class of pharmacological agents. Liposomes are closed artificial spherical vesicles made of a lipid bilayer that mimic cell membrane and can be synthesized in a range of sizes from 50 nm to 1000 nm. For biological applications, such as drug delivery, the optimal size ranges from 50 nm to 500 nm and can be employed for packaging and delivery of different types of molecules, including small organics, peptides, RNA, DNA, diagnostic- and therapeutic agents (Luk, B. T., R. H. Fang, and L. Zhang, *Lipid- and polymer-based nanostructures for cancer theranostics*. Theranostics, 2012. 2(12): p. 1117-26; Al-Jamal, W. T. and K. Kostarelos, *Liposomes: from a clinically established drug delivery system to a nanoparticle platform for theranostic nanomedicine*. Acc Chem Res, 2011. 44(10): p. 1094-104).

Liposomal nanocarriers have been developed to mitigate side effects, enhance delivery, and reduce non-target toxicity based on either active or passive targeting mechanisms. An example of a liposomal nanocarrier is the FDA approved drug, Doxil®, the trade name of the liposomal encapsulated topoisomerase inhibitor Doxorubicin, which is used in treatment of certain breast cancers and pediatric cancers (Chang, H. I. and M. K. Yeh, *Clinical development of liposome-based drugs: formulation, characterization, and therapeutic efficacy*. Int J Nanomedicine, 2012. 7: p. 49-60, Porter, C. J., et al., *The polyoxyethylene/polyoxypropylene block co-polymer poloxamer-407 selectively redirects intravenously injected microspheres to sinusoidal endothelial cells of rabbit bone marrow*. FEBS letters, 1992. 305(1): p. 62-69) and has the ability to target tumors due to long circulation time and enhanced permeability and retention (EPR) effect (Dawidczyk, C. M., et al., *State-of-the-art in design rules for drug delivery platforms: lessons learned from FDA-approved nanomedicines*. J Control Release, 2014. 187: p. 133-44; Khawar, I. A., J. H. Kim, and H. J. Kuh, *Improving drug delivery to solid tumors: Priming the tumor microenvironment*. J Control Release, 2015. 201C: p. 78-89).

Sou et al. synthesized bone marrow targeting liposomes with negatively charged surface with phospholipid and cholesterol based liposomes. Sou et al. reported that liposomes containing DPPC, cholesterol, PEG, and N-(3-carboxy-1-exopropyl)-1,5-dihexadecy ester (SA-lipid) targets bone marrow. SA-lipid was intended to be the active component, and 10 mole % of SA-lipid in the liposome was used to target bone marrow. Moreover, Sou et al. synthesized 250 nm size liposomes and modulated PEG concentration to observe the effect on the bone marrow uptake. They found high uptake of negatively charged liposomes into bone marrow with as low as 0.6% of PEG content. However, this system lacks image-guided drug delivery and does not show minimal accumulation in the tumor Allen et al. tested uptake of liposomes into macrophage in vitro with various composition and size and found that size of liposome is inversely correlated to uptake; i.e. as liposome size decreases, the uptake by macrophages increases. However, these experiments were performed in vitro and do not demonstrate that the liposomes can target the bone marrow while minimizing tumor uptake.

Current methods for imaging mass of bone marrow include Tc-sulfur colloid (SPECT), MRI, CT, and PET. However, these methods are not quantitation or high-resolution which may limit tracking and quantification of delivery. In case of PET, FLT has been reported on marrow imaging tool but it images proliferating marrow not quiescent marrow.

Further, current techniques for administering radiation requires stringent control of radiation delivery to diseased tissue while avoiding normal tissue; however, it is challenging to achieve radiation dosing of normal tissue below 25% of the radiation dosed to the tumor. Although these low levels may be achievable using collimators, a significant dose of radiation to normal tissue is still administered.

Radioprotectant drugs may be administered to limit damage caused by exposure of normal tissue to radiation. However, current radioprotectants cause illness and blood pressure problems, are hard to solubilize, are toxic outside out of the bone marrow, and have only a short window of effectiveness post administration (e.g., 1 hour or less).

Thus, there remains a need for formulations that can selectively target bone marrow and reticuloendothelial system, while minimizing delivery to the tumor, in order to deliver drugs such as radioprotectants (e.g., Amifostine®, e.g., N-acetylcysteine, e.g., GT3) or growth factors (e.g., EPO, GCSF, etc.) that can prevent BMS or aid recovery post radiation therapy. New formulations, methods, and strategies are needed to improve targeted and selective drug delivery to bone marrow while minimizing the tumor uptake of the therapeutic agent. Further, there remains a need to map and quantify formulations that are selectively delivered to the bone marrow and reticuloendothelial system. Further, there remains a need to map and quantify formulations that are selectively delivered to the bone marrow and reticuloendothelial system. Further, there remains a need for physiologic targeting substances to lymph nodes (e.g., via systemic delivery), e.g., drugs, vaccines, adjuvants, and antibodies, and for the ability to selectively eliminate cell clones expressing antigens to viral agents (e.g., HIV).

SUMMARY OF INVENTION

Described herein are liposome-based nanocarriers that selectively target bone marrow, minimize tumor delivery, and maintain high drug concentrations in bone marrow when compared to conventional systemic delivery. The liposome-based nanocarriers also selectively target lymph nodes and other reticuloendothelial system organs (e.g., spleen, e.g., liver). It is found that, in certain embodiments, a negatively-charged nanocarrier provides performance advantages.

Also described herein are methods of imaging and mapping the bone marrow and/or other reticuloendothelial system organs using the described liposome-based nanocarriers. These methods provide high resolution non-invasive and quantitative imaging via PET, which offers advantages over conventional imaging/tracking methods. Furthermore, in certain embodiments, the liposome-based carriers are used to stabilize and deliver radioprotectant/free radical scavenger drugs to the bone marrow, thereby protecting the bone marrow from subsequent radiation exposure, thereby limiting the adverse impact of radiation exposure on the individual. There are a wide range of scenarios for which such radiation protection is useful, e.g., protection from radiation delivered as part of cancer therapy, radiation from weapons, radiation from materials at a nuclear power plant or nuclear waste site, natural radiation in outer space (e.g., for astronauts), and the like.

In one aspect, the invention is directed to a liposome-based nanocarrier comprising: a lipid; and an organic polymer (e.g., the organic polymer associated, e.g., attached covalently or non-covalently to a moiety of the lipid, e.g., associated by other forces, e.g., van der Waals forces) (e.g., wherein the organic polymer comprises polyethylene glycol, e.g., wherein the organic polymer comprises dextran), wherein the liposome-based nanocarrier has a surface having a negative charge (e.g., a negative zeta potential) due to the lipid.

In certain embodiments, the lipid comprises a member selected from the group consisting of 1,2-dioleoyl-sn-glycero-3-phosphoethanolamine-N-(succinyl) (succinyl PE), 1,2-distearoyl-sn-glycero-3-phosphocholine (DSPC), cholesterol, 1,2-distearoyl-sn-glycero-3-phosphoethanolamine (DSPE), and 1,2-dipalmitoyl-sn-glycero-3-phosphoethanolamine-N-(succinyl) (succinyl-DPPE). In certain embodiments, the lipid is labeled (e.g., associated, e.g., attached covalently or non-covalently to a moiety of the surface) with an isotope and chelator.

In certain embodiments, the isotope comprises a member selected from the group consisting of $^{64}$Cu, $^{66/68}$Ga, $^{86}$Y, $^{111}$In, $^{67}$Ga, $^{124/131}$I, and $^{177}$Lu. In certain embodiments, the chelator comprises a member selected from the group consisting of 1,4,7,10-tetraazacyclododecane-1,4,7,10-tetraacetic acid (DOTA) and 1,4,7-triazacyclononane-1,4,7-trisacetic acid (NOTA). In certain embodiments, the chelator comprises a member selected from the group consisting of DOTA-Bn-DSPE and NOTA-Bn-DSPE.

In certain embodiments, the organic polymer comprises polyethylene glycol (PEG).

In certain embodiments, the nanocarrier comprises 1,2-distearoyl-sn-glycero-3-phosphoethanolamine-N-methoxy (polyethylene glycol) (mPEG-DSPE).

In certain embodiments, the concentration of PEG is from about 0.5 wt. % to about 10 wt. %. In certain embodiments, the concentration of PEG is from 0.75 wt. % to about 1.25 wt. % (e.g., about 1 wt. %). In certain embodiments, the concentration of PEG is from about 6 wt. % to about 8 wt. % (e.g., about 7 wt. %). In certain embodiments, the liposome-based nanocarrier is at least 3 mole % lipid (e.g., at least 5 mole % lipid, e.g., at least 10 mole % lipid, e.g., at least 15 mole % lipid) (e.g., wherein the lipid is succinyl DPPE).

In certain embodiments, the liposome-based nanocarrier comprises an associated drug (e.g., wherein the associated drug is encapsulated inside of the liposome, incorporated into lipid layers, or covalently attached to the lipid on the surface of liposome). In certain embodiments, the associated drug comprises a member selected from the group consisting of: an free radical scavenger (e.g., GT3); a radioprotectant (e.g., Amifostine, N-acetylcysteine, gamma-tocotrienol, Genistein), a growth factor (e.g., erythropoietin, granulocyte colony-stimulating factor, RNAi therapeutics (e.g., GTI-2040 (ribonucleotide reductase), SPC2996 (Bcl-2), LY2181308 (survivin), e.g., immunosuppressors (e.g., Tacrolimus, mTOR inhibitors, corticosteroids, antibiotics, epinephrine analogs, RNAi against Bim and PUMA)), a bisphosphonate (e.g., alendronate, ibandronate, risedronic acid, zoledonic acid), a selective estrogen receptor modulator (e.g., raloxifene), a parathyroid hormone modulator (e.g., teriparatide), a biological (e.g., denosumab), and a chemotherapeutic drug (e.g., any of the chemotherapeutic drugs listed in Table 4).

In certain embodiments, the liposome-based nanocarrier has an average diameter in a range from 30 nm to 300 nm. In certain embodiments, the liposome-based nanocarrier has an average diameter in a range from 50 nm to 200 nm. In certain embodiments, the liposome-based nanocarrier has an average diameter in a range from about 80 nm to 150 nm. In certain embodiments, the liposome-based nanocarrier has an average diameter that is about 90 nm. In certain embodiments, the liposome-based nanocarrier has an average diameter that is about 140 nm.

In certain embodiments, the liposome-based nanocarrier further comprises one or more of (i), (ii), and (iii), as follows: (i) from 3 to 20 wt. % (e.g., about 10 wt. %) succinyl DPPE; (ii) from 0.5 to 2 wt. % (e.g., about 1 wt. %) PEG (e.g., for bone marrow targeting); and (iii) from 5 to 9 wt. % (e.g., about 7 wt. %, e.g., 7±1.5 wt. %) PEG (e.g., for lymph node targeting).

In certain embodiments, the negative charge of the surface of the liposome-based nanocarrier has a magnitude from 15 mV to 25 mV.

In another aspect, the invention is directed to a method for imaging a subject (e.g., a human, e.g., a patient), the method comprising: administering to the subject a liposome-based nanocarrier, wherein the lipid is labeled (e.g., associated, e.g., attached covalently or non-covalently to a moiety of the surface) with an isotope and a chelator (e.g., wherein the isotope does not dissociate from a chelator (e.g., DOTA-Bn-DSPE, NOTA-Bn-DSPE) at room temperature for 24 hours).

In certain embodiments, the method further comprises obtaining and displaying a positron emission tomography (PET) and/or Positron emission tomography-computed tomography (PET/CT) image of at least one tissue of the subject comprising the liposome-based nanocarrier.

In certain embodiments, the method further comprises quantitatively measuring (e.g., by a processor of a computing device) a distribution of the liposome-based nanocarrier in at least one tissue of the subject.

In certain embodiments, the method comprises quantitatively measuring the distribution of the liposome-based nanocarrier in an organ of the reticuloendothelial system.

In certain embodiments, the organ comprises a member selected from the group consisting of liver, spleen, and bone marrow.

In certain embodiments, the method comprises determining (e.g., by a processor of a computing device) a concentration and/or total amount of delivered radiolabeled drug in the tissue based on a positron emission tomography (PET) or Positron Emission Tomography-Computed Tomography (PET/CT) image of the tissue.

In certain embodiments, the method comprises quantitatively measuring the distribution of the liposome-based nanocarrier in one or more lymph nodes (e.g., wherein the concentration and total amount of delivered radiolabeled drug in the tissue is measured from a positron emission tomography (PET) and/or Positron emission tomography-computed tomography (PET/CT) image).

In certain embodiments, the administered liposome-based nanocarrier demonstrates selective targeting of bone marrow of the subject such that concentration of the liposome-based nanocarrier in bone marrow is at least 3 fold greater than the concentration of the liposome-based nanocarrier in any of the tumor tissue (e.g., at least 5 fold, e.g., at least 8 fold) at a given time following administration of the liposome-based nanocarrier, wherein the given time is at least 1 hour, at least 4 hours, at least 8 hours, at least 16 hours, at least 20 hours, at least 24 hours following administration.

In certain embodiments, the method comprises capturing and displaying a sequence of PET images in real time.

In another aspect, the invention is directed to a method of treating a subject, the method comprising administering the liposome-based nanocarrier to the subject suffering from or susceptible to a disease and/or condition. In certain embodiments, the disease and/or condition comprises a member selected from the group consisting of bone marrow suppression (BMS), myelodysplastic syndrome (MDS), acute myeloid leukemia (AML), chronic myeloid leukemia (CML), sepsis, graft-versus-host-disease (GVHD), bone metastasis, and osteoporosis. In certain embodiments, the disease and/or condition comprises exposure to radiation (e.g., radiation delivered as part of cancer therapy, radiation from weapons, radiation from materials at a nuclear power plant or nuclear waste site, or natural radiation in outer space).

In certain embodiments, the method further comprises after administering the liposome-based nanocarrier, administering a chemotherapeutic and/or radiation therapy.

In certain embodiments, the administered liposome-based nanocarrier demonstrates selective targeting of bone marrow of the subject such that the concentration of the liposome-based nanocarrier in bone marrow is at least 3 fold greater than the concentration of the liposome-based nanocarrier in any of the tumor tissue (e.g., at least 3 fold, e.g., at least 5 fold, e.g., at least 8 fold) at a given time following administration of the liposome-based nanocarrier, wherein the given time is at least 1 hour, (e.g., at least 4 hours, at least 16 hours, at least 20 hours, at least 24) hours following administration.

In another aspect, the invention is directed to a method of monitoring a patient, the method comprising administering the liposome-based nanocarrier to a patient suffering from or susceptible to a disease and/or condition; and investigating a quantity of drug delivered to at least one tissue of the patient.

In another aspect, the invention is directed to a method of imaging an organ of the reticuloendothelial system in a subject (e.g., animal, e.g., human), the method comprising:

detecting radiation from the liposome-based nanocarrier, the subject having been administered the liposome-based nanocarrier.

In certain embodiments, the radiation is detected via an external PET imaging system.

In certain embodiments, the organ comprises a member selected from the group consisting of active bone marrow, liver, and spleen.

In certain embodiments, the method comprises displaying an image corresponding to the detected radiation, the image visually distinguishing active bone marrow from other tissue and, optionally, quantifying the concentration of drug and/or liposome-based nanocarrier.

In another aspect, the invention is directed to a liposome-based nanocarrier comprising: a lipid; and an organic polymer (e.g., the organic polymer associated, e.g., attached covalently or non-covalently to a moiety of the lipid, e.g., associated by other forces, e.g., van der Waals forces) (e.g., wherein the organic polymer comprises polyethylene glycol, e.g., wherein the organic polymer comprises dextran), wherein the liposome-based nanocarrier has a surface having a negative charge (e.g., a negative zeta potential) due to the lipid, for use in a method of treating a disease and/or condition in a subject, wherein the treating comprises delivering the composition to the subject.

In another aspect, the invention is directed to a liposome-based nanocarrier comprising: a lipid; and an organic polymer (e.g., the organic polymer associated, e.g., attached covalently or non-covalently to a moiety of the lipid, e.g., associated by other forces, e.g., van der Waals forces) (e.g., wherein the organic polymer comprises polyethylene glycol, e.g., wherein the organic polymer comprises dextran), wherein the liposome-based nanocarrier has a surface having a negative charge (e.g., a negative zeta potential) due to the lipid, for use in a method of monitoring of a disease and/or condition in a subject, wherein the monitoring comprises delivering the composition to the subject.

In another aspect, the invention is directed to a liposome-based nanocarrier comprising: a lipid; and an organic polymer (e.g., the organic polymer associated, e.g., attached covalently or non-covalently to a moiety of the lipid, e.g., associated by other forces, e.g., van der Waals forces) (e.g., wherein the organic polymer comprises polyethylene glycol, e.g., wherein the organic polymer comprises dextran), wherein the liposome-based nanocarrier has a surface having a negative charge (e.g., a negative zeta potential) due to the lipid, for use in (a) a method of treating a disease and/or condition in a subject or (b) in a method of monitoring of a disease and/or condition in a subject, wherein the monitoring comprises delivering the composition to the subject.

In another aspect, the invention is directed to a liposome-based nanocarrier comprising: a lipid; and an organic polymer (e.g., the organic polymer associated, e.g., attached covalently or non-covalently to a moiety of the lipid, e.g., associated by other forces, e.g., van der Waals forces) (e.g., wherein the organic polymer comprises polyethylene glycol, e.g., wherein the organic polymer comprises dextran), wherein the liposome-based nanocarrier has a surface having a negative charge (e.g., a negative zeta potential) due to the lipid, for use in therapy.

In another aspect, the invention is directed to a liposome-based nanocarrier comprising: a lipid; and an organic polymer (e.g., the organic polymer associated, e.g., attached covalently or non-covalently to a moiety of the lipid, e.g., associated by other forces, e.g., van der Waals forces) (e.g., wherein the organic polymer comprises polyethylene glycol, e.g., wherein the organic polymer comprises dextran), wherein the liposome-based nanocarrier has a surface having a negative charge (e.g., a negative zeta potential) due to the lipid, for use in monitoring a disease or condition.

In certain embodiments, the lipid comprises a member selected from the group consisting of 1,2-dioleoyl-sn-glycero-3-phosphoethanolamine-N-(succinyl) (succinyl PE), 1,2-distearoyl-sn-glycero-3-phosphocholine (DSPC), cholesterol, 1,2-distearoyl-sn-glycero-3-phosphoethanolamine (DSPE), and 1,2-dipalmitoyl-sn-glycero-3-phosphoethanolamine-N-(succinyl) (succinyl-DPPE). In certain embodiments, the lipid is labeled (e.g., associated, e.g., attached covalently or non-covalently to a moiety of the surface) with an isotope and chelator.

In certain embodiments, the isotope comprises a member selected from the group consisting of $^{64}$Cu, $^{66/68}$Ga, $^{86}$Y, $^{111}$In, $^{67}$Ga, $^{124/131}$I, and $^{177}$Lu. In certain embodiments, the chelator comprises a member selected from the group consisting of 1,4,7,10-tetraazacyclododecane-1,4,7,10-tetraacetic acid (DOTA) and 1,4,7-triazacyclononane-1,4,7-trisacetic acid (NOTA). In certain embodiments, the chelator comprises a member selected from the group consisting of DOTA-Bn-DSPE and NOTA-Bn-DSPE.

In certain embodiments, the organic polymer comprises polyethylene glycol (PEG).

In certain embodiments, the nanocarrier comprises 1,2-distearoyl-sn-glycero-3-phosphoethanolamine-N-methoxy (polyethylene glycol) (mPEG-DSPE).

In certain embodiments, the concentration of PEG is from about 0.5 wt. % to about 10 wt. %. In certain embodiments, the concentration of PEG is from 0.75 wt. % to about 1.25 wt. % (e.g., about 1 wt. %). In certain embodiments, the concentration of PEG is from about 6 wt. % to about 8 wt. % (e.g., about 7 wt. %). In certain embodiments, the liposome-based nanocarrier is at least 3 mole % lipid.

In certain embodiments, the liposome-based nanocarrier comprises an associated drug (e.g., wherein the associated drug is encapsulated inside of the liposome, incorporated into lipid layers, or covalently attached to the lipid on the surface of liposome). In certain embodiments, the associated drug comprises a member selected from the group consisting of: an free radical scavenger (e.g., GT3); a radioprotectant (e.g., Amifostine, N-acetylcysteine, gamma-tocotrienol, Genistein), a growth factor (e.g., erythropoietin, granulocyte colony-stimulating factor, RNAi therapeutics (e.g., GTI-2040 (ribonucleotide reductase), SPC2996 (Bcl-2), LY2181308 (survivin), e.g., immunosuppressors (e.g., Tacrolimus, mTOR inhibitors, corticosteroids, antibiotics, epinephrine analogs, RNAi against Bim and PUMA)), a bisphosphonate (e.g., alendronate, ibandronate, risedronic acid, zoledonic acid), a selective estrogen receptor modulator (e.g., raloxifene), a parathyroid hormone modulator (e.g., teriparatide), a biological (e.g., denosumab), and a chemotherapeutic drug (e.g., any of the chemotherapeutic drugs listed in Table 4).

In certain embodiments, the liposome-based nanocarrier has an average diameter in a range from 30 nm to 300 nm. In certain embodiments, the liposome-based nanocarrier has an average diameter in a range from 50 nm to 200 nm. In certain embodiments, the liposome-based nanocarrier has an average diameter in a range from about 80 nm to 150 nm. In certain embodiments, the liposome-based nanocarrier has an average diameter that is about 90 nm. In certain embodiments, the liposome-based nanocarrier has an average diameter that is about 140 nm.

In certain embodiments, the liposome-based nanocarrier comprises one or more of (i), (ii), and (iii), as follows: (i) from 3 to 20 wt. % (e.g., about 10 wt. %) succinyl DPPE;

(ii) from 0.5 to 2 wt. % (e.g., about 1 wt. %) PEG (e.g., for bone marrow targeting); and (iii) from 5 to 9 wt. % (e.g., about 7 wt. %) PEG (e.g., for lymph node targeting).

In certain embodiments, the negative charge of the surface of the liposome-based nanocarrier has a magnitude from 15 mV to 25 mV.

In certain embodiments, the treating and/or monitoring further comprises: administering to the subject a liposome-based nanocarrier, wherein the lipid is labeled (e.g., associated, e.g., attached covalently or non-covalently to a moiety of the surface) with an isotope and a chelator (e.g., wherein the isotope does not dissociate from a chelator (e.g., DOTA-Bn-DSPE, NOTA-Bn-DSPE) at room temperature for 24 hours). In certain embodiments, the treating and/or monitoring further comprises obtaining and displaying a positron emission tomography (PET) and/or Positron emission tomography-computed tomography (PET/CT) image of at least one tissue of the subject comprising the liposome-based nanocarrier. In certain embodiments, the treating and/or monitoring further comprises quantitatively measuring (e.g., by a processor of a computing device) a distribution of the liposome-based nanocarrier in at least one tissue of the subject. In certain embodiments, the treating and/or monitoring further comprises quantitatively measuring the distribution of the liposome-based nanocarrier in an organ of the reticuloendothelial system.

In certain embodiments, the organ comprises a member selected from the group consisting of liver, spleen, and bone marrow.

In certain embodiments, the treating and/or monitoring further comprises determining (e.g., by a processor of a computing device) a concentration and/or total amount of delivered radiolabeled drug in the tissue based on a positron emission tomography (PET) or Positron Emission Tomography-Computed Tomography (PET/CT) image of the tissue. In certain embodiments, the treating and/or monitoring further comprises quantitatively measuring the distribution of the liposome-based nanocarrier in one or more lymph nodes (e.g., wherein the concentration and total amount of delivered radiolabeled drug in the tissue is measured from a positron emission tomography (PET) and/or Positron emission tomography-computed tomography (PET/CT) image).

In certain embodiments, the administered liposome-based nanocarrier demonstrates selective targeting of bone marrow of the subject such that concentration of the liposome-based nanocarrier in bone marrow is at least 3 fold greater than the concentration of the liposome-based nanocarrier in any of the tumor tissue (e.g., at least 5 fold, e.g., at least 8 fold) at a given time following administration of the liposome-based nanocarrier, wherein the given time is at least 1 hour, at least 4 hours, at least 8 hours, at least 16 hours, at least 20 hours, at least 24 hours following administration.

In certain embodiments, the treating and/or monitoring further comprises capturing and displaying a sequence of PET images in real time.

In certain embodiments, the disease and/or condition comprises a member selected from the group consisting of bone marrow suppression (BMS), myelodysplastic syndrome (MDS), acute myeloid leukemia (AML), chronic myeloid leukemia (CML), sepsis, graft-versus-host-disease (GVHD), bone metastasis, and osteoporosis. In certain embodiments, the disease and/or condition comprises exposure to radiation (e.g., radiation delivered as part of cancer therapy, radiation from weapons, radiation from materials at a nuclear power plant or nuclear waste site, or natural radiation in outer space).

In certain embodiments, the treating and/or monitoring further comprises after administering the liposome-based nanocarrier, administering a chemotherapeutic and/or radiation therapy.

In certain embodiments, the administered liposome-based nanocarrier demonstrates selective targeting of bone marrow of the subject such that the concentration of the liposome-based nanocarrier in bone marrow is at least 3 fold greater than the concentration of the liposome-based nanocarrier in any of the tumor tissue (e.g., at least 3 fold, e.g., at least 5 fold, e.g., at least 8 fold) at a given time following administration of the liposome-based nanocarrier, wherein the given time is at least 1 hour, following administration.

In certain embodiments, the treating and/or monitoring further comprises administering the liposome-based nanocarrier to a patient suffering from or susceptible to a disease and/or condition; and investigating a quantity of drug delivered to at least one tissue of the patient.

In certain embodiments, wherein the imaging and/or monitoring comprises monitoring an organ of the reticuloendothelial system in a subject (e.g., animal, e.g., human), and wherein the imaging and/or monitoring comprises detecting radiation from the liposome-based nanocarrier, the subject having been administered the liposome-based nanocarrier.

In certain embodiments, wherein the radiation is detected via an external PET imaging system.

In certain embodiments, the organ comprises a member selected from the group consisting of active bone marrow, liver, and spleen.

In certain embodiments, the imaging and/or monitoring further comprises displaying an image corresponding to the detected radiation, the image visually distinguishing active bone marrow from other tissue and, optionally, quantifying the concentration of drug and/or liposome-based nanocarrier.

Elements of embodiments involving one aspect of the invention (e.g., methods) can be applied in embodiments involving other aspects of the invention (e.g., compositions), and vice versa.

DEFINITIONS

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

"Biocompatible": The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable.

"Biodegradable": As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis. In some embodiments, biodegradable polymeric materials break down into their component polymers. In some embodiments, breakdown of biodegradable materials (including, for example, biodegradable polymeric materials) includes hydrolysis of ester bonds. In some embodiments, breakdown of materials (including, for example, biodegradable polymeric materials) includes cleavage of urethane linkages.

"Biomolecule": As used herein, "biomolecule" refers to bioactive, diagnostic, and prophylactic molecules. Biomolecules that can be used in the present invention include, but are not limited to, synthetic, recombinant or isolated peptides and proteins such as antibodies and antigens, receptor ligands, enzymes, and adhesion peptides; nucleotides and polynucleic acids such as DNA and antisense nucleic acid molecule; activated sugars and polysaccharides; bacteria; viruses; and chemical drugs such as antibiotics, antiinflammatories, and antifungal agents.

"Carrier": As used herein, "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Free radical scavenger": As used herein "free radical scavenger" refers to a drug that removes the ionization induced by radiation in tissues (e.g., human tissues).

"Radiolabel": As used herein, "radiolabel" refers to a moiety comprising a radioactive isotope of at least one element. Exemplary suitable radiolabels include but are not limited to those described herein. In some embodiments, a radiolabel is one used in positron emission tomography (PET). In some embodiments, a radiolabel is one used in single-photon emission computed tomography (SPECT). In some embodiments, radioisotopes comprise $^{99m}$Tc, $^{111}$In, $^{64}$Cu, $^{67}$Ga, $^{68}$Ga, $^{186}$Re, $^{188}$Re, $^{153}$Sm, $^{177}$Lu, $^{67}$Cu, $^{123}$I, $^{124}$I, $^{125}$I, $^{131}$I, $^{11}$C, $^{13}$N, $^{15}$O, $^{18}$F, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{105}$Rh, $^{111}$Ag, $^{89}$Zr, $^{225}$Ac, and $^{192}$Ir.

"Subject": As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

"Small molecule": As used herein, the term "small molecule" can refer to a non-polymeric molecule, for example, or a species less than 5000 Da.

"Therapeutic agent": As used herein, the phrase "therapeutic agent" refers to any agent that has a therapeutic effect and/or elicits a desired biological and/or pharmacological effect, when administered to a subject.

"Therapeutic index": As used herein, the phrase "therapeutic index" refers to a concentration in target tissue in relationship to normal tissues in the region. For example, "therapeutic index" refers to a concentration in the bone marrow compared to a concentration in the surrounding soft tissue (e.g., muscle).

"Treatment": As used herein, the term "treatment" (also "treat" or "treating") refers to any administration of a substance that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Drawings are presented herein for illustration purposes, not for limitation.

BRIEF DESCRIPTION OF DRAWINGS

The foregoing and other objects, aspects, features, and advantages of the present disclosure will become more apparent and better understood by referring to the following description taken in conduction with the accompanying drawings, in which:

FIG. 2A shows that $^{64}$Cu was incubated in pH 5.5 acetate buffer at 50° C. and analyzed by instant thin layer chromatography (ITLC). Left panel shows 100% incorporation of $^{64}$Cu into liposomes.

FIG. 2B shows that the size distribution of liposome does not change after chelation of $^{64}$Cu.

FIG. 2C shows that $^{64}$Cu labeled liposomes were incubated in 50% FCS for 2, 4, 8, and 24 h. ITLC was used to determine the stability of $^{64}$Cu on the liposomes. $^{64}$Cu was not released from liposomes up to 24 h.

FIG. 3A, left panel shows the exemplary 90 nm diameter liposome distribution at 4 h and 24 h after injection. FIG. 3A, right panel shows the exemplary 140 nm diameter liposome distribution at 4 h and 24 h after injection.

FIG. 3B shows that the blood clearance of liposome was measured by collecting blood from mice after $^{64}$Cu labeled liposomes were injected through i.v. Both 90 nm and 140 nm liposomes show similar clearance from blood and half-life of blood clearance of liposomes are 4.6±1.9 h and 140 nm is 4.2±0.8 h respectively.

FIGS. 4A-4C shows representative PET/CT images of mice administered with an exemplary 90 nm $^{64}$Cu-labeled liposome-based nanocarrier.

FIG. 4A shows representative whole body images (slice) showing CT, PET/CT fusion and PET images of mice.

FIG. 4B shows a magnified image depicting CT, PET/CT fusion and PET images of tibia of the same mice.

FIG. 4C shows volume-rendered images showing CT, PET/CT fusion and PET images of tibia demonstrate that accumulation of liposome-based nanocarriers is specific to bone marrow.

FIGS. 6A-6B show time activity curves of $^{64}$Cu labeled liposome after tail vein injection and compartment model analysis.

FIG. 6A shows a normalized time activity curve constructed from a region of interest (ROI) drawn around heart, liver, spleen, and sacrum from the image of 1 h dynamic PET scanning combined with static PET images of 2.5, 3.7, 5, 7.5, 10, 20, 24, and 28 h. Motion artifact, partial volume effect, attenuation, scattering correction have not been applied for driving these parameters.

FIG. 6B shows a time activity curve of blood was fitted with 2-compartment model.

FIG. 10A shows SDS page of ovalbumin labeling to the surface of lymph node targeting liposomes. Marker, ovalbumin, and DIBO conjugated ovalbumin was loaded on lanes 1-3. After conjugated DIBO-oval with azido-labeled liposome-based nanocarriers for 1 hour, 2 hours, and 3 hours, the samples were loaded on lanes 4-6.

FIGS. 10B and 10C show that liposome-based nanocarriers labeled with ovalbumin have a larger diameter that non-labeled liposome-based nanocarriers (e.g., 143 nm and 131 nm in diameter, respectively).

FIGS. 19A-19C show that BMT liposome stability has been tested as a kit formulation. Size, zeta potential, and $^{64}$Cu labeling efficiency remain stable for 9 months. Liposome sizes (FIG. 19A), zeta potential at pH 7.4 (FIG. 19B), and labeling efficiency (FIG. 19C) were measured for 1, 2, 3, 4, 6, and 9 months.

FIG. 20A shows a chemical structure of 1,2-dioleoyl-3-trimethylammonium-propane (DOTAP).

FIG. 20B shows a chemical structure of 1,2-dioleoyl-sn-glycero-3-phosphoethanolamine (DOPE).

FIG. 20C shows zeta potential at pH 7.4 for positively charged liposomes have different ratios of DOPE:DOTAP. DOPE:DOTAP=3:1 was chosen as its zeta potential at pH 7.4 is 14.8 mV and its absolute value is similar to BMT liposomes having a zeta potential at pH 7.4 of −18.8 mV.

FIGS. 22A and 22B show $^{64}$CU PET/CT images of lymph node targeting of liposomes with negative (FIG. 22A) and positive charge (FIG. 22B) with 1% PEG.

FIGS. 24A-24C show $^{64}$Cu and $^{[124/131]}$I labeling of GT3 containing BMT liposomes. GT3 containing BMT liposomes were labeled with both $^{64}$Cu and $^{131}$I to monitor its pharmacokinetics.

FIG. 24A shows that GT3 does not interfere labeling of $^{64}$Cu to BMT liposome.

FIG. 24B shows that $^{131}$I was labeled using sodium iodide with iodogen in mild condition.

FIG. 24C shows that $^{131}$I labeled liposomes were separated using PD-10 size exclusion column.

FIG. 27A shows a coronal image of CT, PET, and PET/CT images.

FIG. 27B shows a maximum intensity projection (MIP) which contains 3D information.

DETAILED DESCRIPTION

Figure 1A:
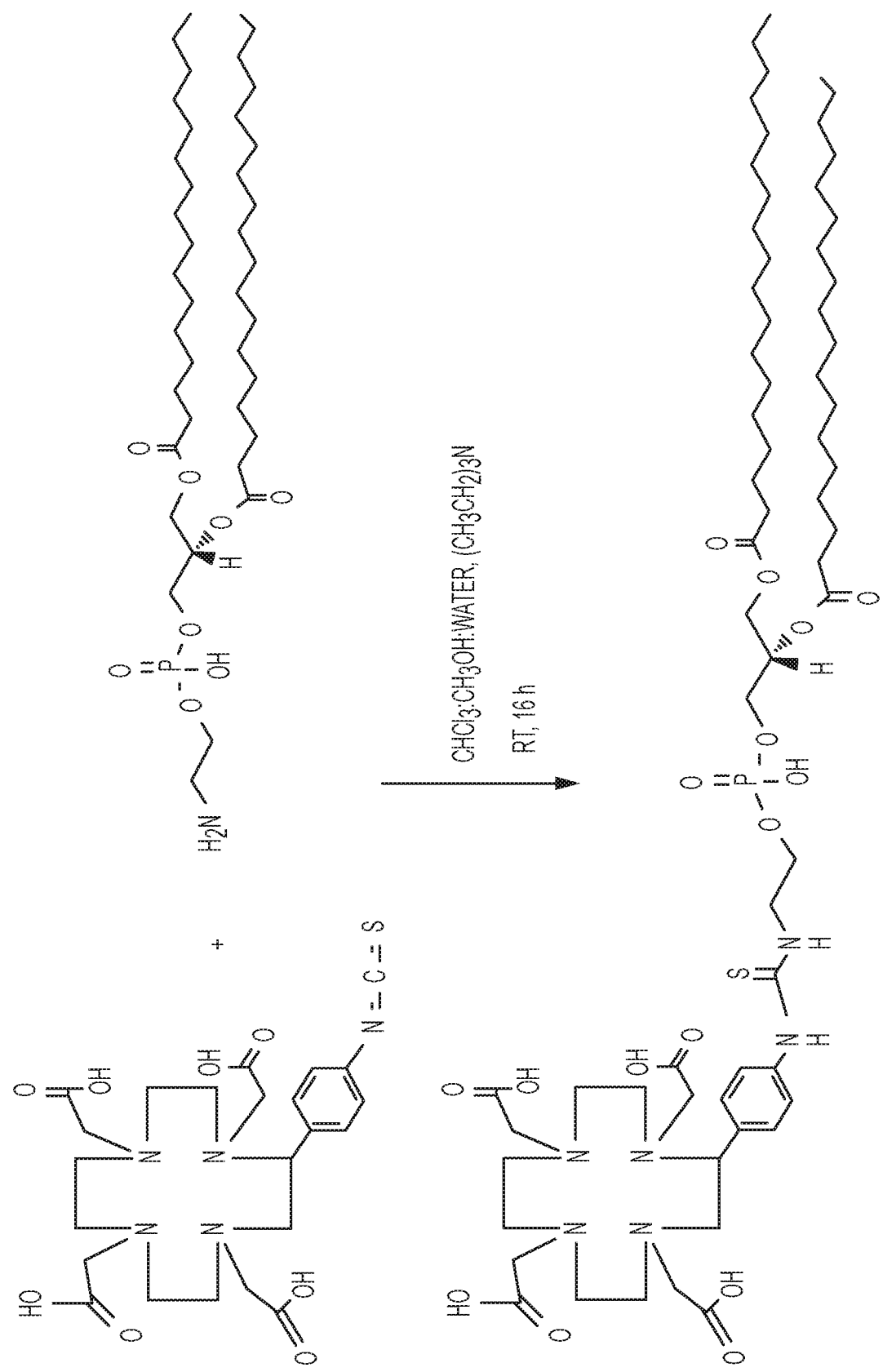
FIG. 1A shows the synthetic scheme of DSPE-Bn-DOTA to chelate $^{64}$Cu or $^{177}$Lu, for example. Chloroform, methanol, and water mixture was used as solvent and triethyleneimine was used as a base.

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Described herein are liposome-based nanocarriers that selectively target bone marrow and/or lymph nodes, minimize tumor delivery, and maintain high drug concentrations (e.g., Amifostine or other radioprotectants) in bone marrow and/or lymph nodes when compared to conventional systemic delivery. For high resolution non-invasive imaging, DOTA-labeled or other chelator (e.g., NOTA-labeled) lipid was labeled with a PET isotope (e.g., $^{64}$Cu) to follow the pharmacokinetics of liposomes in vivo and to quantitatively determine the liposomal distribution in different organs. Liposomal formulations were prepared with a composition comprising succinyl PE, DSPC, cholesterol, and mPEG-DSPE, were 90 nm and 140 nm in diameter, and were doped with DSPE-Bn-DOTA for stable $^{64}$Cu incorporation into liposomes. PET imaging and biodistribution of $^{64}$Cu labeled liposomes showed that the accumulation in bone marrow was as high as 15.18% ID/g for 90 nm liposomes and 7.01% ID/g for 140 nm liposomes. The liposome formulations targeted bone marrow with high efficiency and avoided high accumulation in tumor xenografts (e.g., an 8.5-fold targeted delivery to marrow over tumor).

As described herein, liposomal nanocarriers were developed and characterized as a stable PET labeled liposomal delivery system and enhance the delivery of drugs to the reticuloendothelial system (RES), particularly bone marrow while reducing the dose delivered to the tumor.

Bone marrow targeting liposomes were developed that can be radiolabeled with $^{64}$Cu (e.g., or other radiolabels) for positron emission topography (PET) imaging guided drug delivery and quantification. Sizes, surface charges, and poly(ethylene) glycol (PEG) contents influenced the targeting efficiency. In certain embodiments, biodistribution and imaging data showed that 10% succinyl DPPE, 1% PEG, and 90 nm diameter size liposomes targeted the bone marrow with high efficiency. This accumulation was 8.5 fold higher than what was observed in PC9 tumor xenografts. Dynamic PET scanning and derived pharmacokinetic parameters were also performed to understand the dynamic behavior of liposomes in vivo. In certain embodiments, the platform described herein can be used for delivering radioprotectants to marrow. In other embodiments, image guided liposomal delivery systems can aid in reducing the harmful side effects commonly associated with radiation therapy.

In certain embodiments, bone marrow phagocytic activity, especially "fixed" macrophages, are supporting elements for hematopoietic bone marrow; quantitatively there is a close association under usual conditions. In certain embodiments, the present disclosure provides a liposomal drug that can image the extent of active bone marrow in mammals (e.g., humans, animals, etc.)

In certain embodiments, the concentration of bone marrow targeted liposomes can be measured quantitatively, using know physics of imaging with standard external PET imaging equipment. Based on the known concentration of drug in each liposome and the measured amount of liposome injected, the concentration and total amount of radiolabeled drug can be measured for delivery to organs.

Using quantitative external PET imaging, the present disclosure also provides that a fraction of the radiolabeled liposome carrier targets lymph nodes, for example, in the drainage bed of a tumor in man. Based on the known concentration of drug in each liposome and the measured amount of liposome injected, the concentration and total amount of radiolabeled drug can be measured for delivery to one or more lymph nodes. Drugs or entities contained in the liposomes and/or functionalized on the liposomes can include, but are not limited to, the following: chemotherapeutic drugs, antigens, adjuvants, etc. PET imaging can be performed with standard equipment in man (PET/CT), and amount of delivered drug can be computed for individual lymph nodes. Corrections can be applied for partial volume effect, by established techniques.

Selective delivery of pharmaceutical agents to bone marrow can selectively protect, modify, and/or destroy the resident bone marrow resident cells. As described above, current approaches to eradicate bone marrow before stem cell transplantation involves radiating the whole body with high doses of radiation. The side effects of total body radiation include damage to intestinal mucosa, salivary, glands and other complications. The liposome-based nanocarriers described herein can selectively deliver chemo- or radio-toxic drugs to marrow, leading to significant depletion of immune cells only in these select areas of the body.

The selective delivery of agents (e.g., bone factors) to bone marrow also promotes bone regeneration, prevention of osteoporosis, faster healing of bone fractures, and/or gene therapy for HIV/AIDS (Viruses. 2015 Jul. 17; 7(7):3910-36). Myelodysplastic syndrome (MDS), where there is reduction in production of red blood cells due to genetic predisposition or previous chemical/radiation exposure can also benefit from selective delivery of the described liposome-based nanocarriers.

Growth factors, such as EPO, are commonly administered to cancer patients undergoing chemo- and radiotherapy to boost red blood counts. However, EPO was shown to promote tumor growth by activating EphB4 receptors (Erythropoietin Stimulates Tumor Growth via EphB4. Cancer Cell. 2015 Nov. 9; 28(5):610-22). Thus, selective delivery of growth factors to marrow while evading tumor tissue can reduce side effects of growth factor treatment to cancer patients.

As described herein, physiologic targeting to bone marrow and fixed macrophages in the liver and spleen are needed to protect subjects from radiation of sensitive cells, to enhance therapeutic index (TI) of drugs which interfere with metastasis to bone marrow, spleen and liver, to optimize delivery of marrow stimulating drugs, such as granulocyte colony-stimulating factor (GCSF) (also known as neupogan), and erythropoietic cells, and to enhance radiosensitivity of marrow elements as preparation for allogenic bone marrow transplantation (ABT).

Radioprotectant/free radical scavengers (e.g., GT3) can help protect bone marrow from ionizing radiation. However, non-target accumulation, low aqueous solubility, and limited bioavailability (or hard to deliver in high doses) are serious impediment in translating GT3 for routine administration. Bone marrow targeting liposomes that deliver radioprotectants such as GT3 protect bone marrow from radiation by enhanced delivery of free radical scavenging and/or stimulating proliferation and differentiation of hematopoietic system. Additionally, radioprotectants minimize the damage to stem cell niche (including vasculature, adipose matrix) and thereby aid faster recovery from exposure from radiation. Targeting bone marrow using the compositions described herein can widen the window of protection of bone marrow compared to non-targeted administration of radioprotectant/free radical scavengers.

A major dose limiting toxicity for most patients undergoing radiation therapy is the marrow toxicity. Though radiation therapy can be curative, the dose and intensity are limited by unintentional exposure to the marrow (e.g., pelvis in case of urological or gynecological malignancies or ribs for breast and lung cancer patients) due to spillover radiation fields. These spillover fields exist despite vast improvements in radiation delivery technologies due to the proximity of the lesions to bone marrow containing organs. The patients cannot receive too much radiation on the grounds that radiation destroys the bone marrow, and therefore most radiation therapies are not performed with curative intent. By administering the compositions described herein prior to radiation (or, in some cases, chemo) therapy, the bone marrow can be protected, and therefore in suitable cases, high dose radiation can be administered to achieve complete cure. The liposomes also have high accumulation in macrophage phagocytic system including liver and spleen (part of a fixed macrophage system). Therefore the composition can be used for protection of liver and spleen from radiation both from internal and external sources. Additionally patients undergoing palliative treatment with agents such as [$^{153}$Sm]-EDTMP or $^{89}$Sr—SrCl$_2$ have potential to benefit from our radioprotectant loaded BMT liposomes.

EXAMPLES

Liposome Formulation and Characterization 1,4,7,10-tetraazacyclododecane 1,4,7,10-tetraacetic acid (DOTA) was used as a chelator (e.g., for $^{64}$Cu) and distearoyl-phosphatidylethanolamine (DSPE) was used as a lipid to anchor in lipid bilayer. FIG. 1A shows synthesis of the DOTA-Bn-DSPE as starting from p-SCN-Bn-DOTA. Moreover, the solvent used for reaction was chloroform, methanol, and water, all of which are removed during evaporation to make a lipid film.

Macrophages are known to take up liposomes, and the uptake is dependent on the surface charge and PEG content of the liposomes. Macrophages with liposomes move to and accumulate in the bone marrow. The amount of succinyl DPPE content was adjusted to modulate the surface charge on the liposomes. As described herein, negative charge on the liposome surface was achieved by adding 10 mole % of commercially available succinyl DPPE. Liposome size was controlled by the pore size of extrusion membrane and dynamic light scattering was used to measure the properties of the liposomes. To control liposome size, 100 nm and 30 nm pore membranes were used, generating liposomes of 140 nm and 90 nm. The poly dispersity index (PDI) was between 0.038 and 0.096, which indicates liposomes were formed with a uniform and narrow size distribution.

Figure 2A:
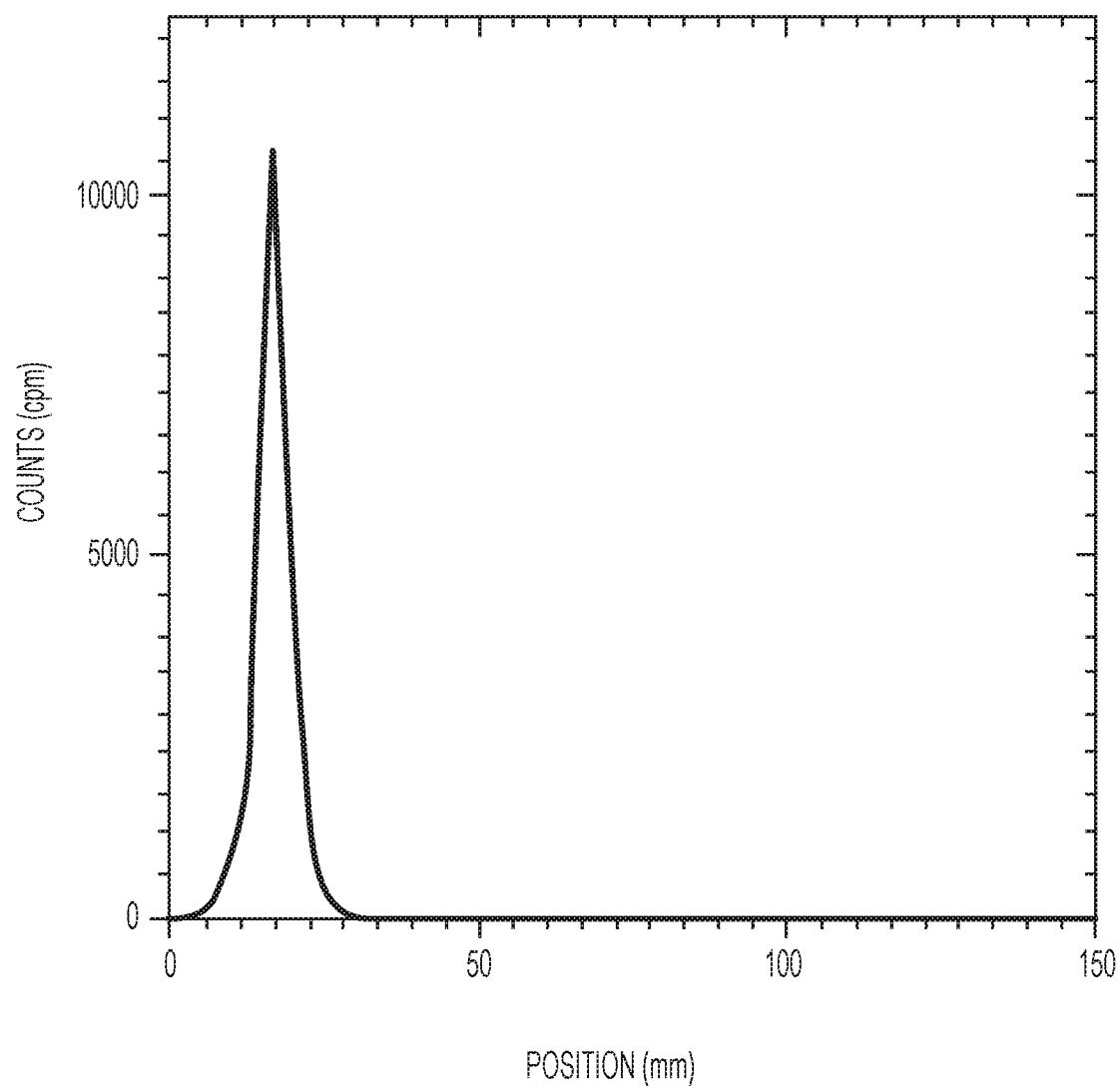
FIGS. 2A-2C show incorporation of $^{64}$Cu on the liposomes doped with DSPE-Bn-DOTA and their stability over time.
Figure 2B:
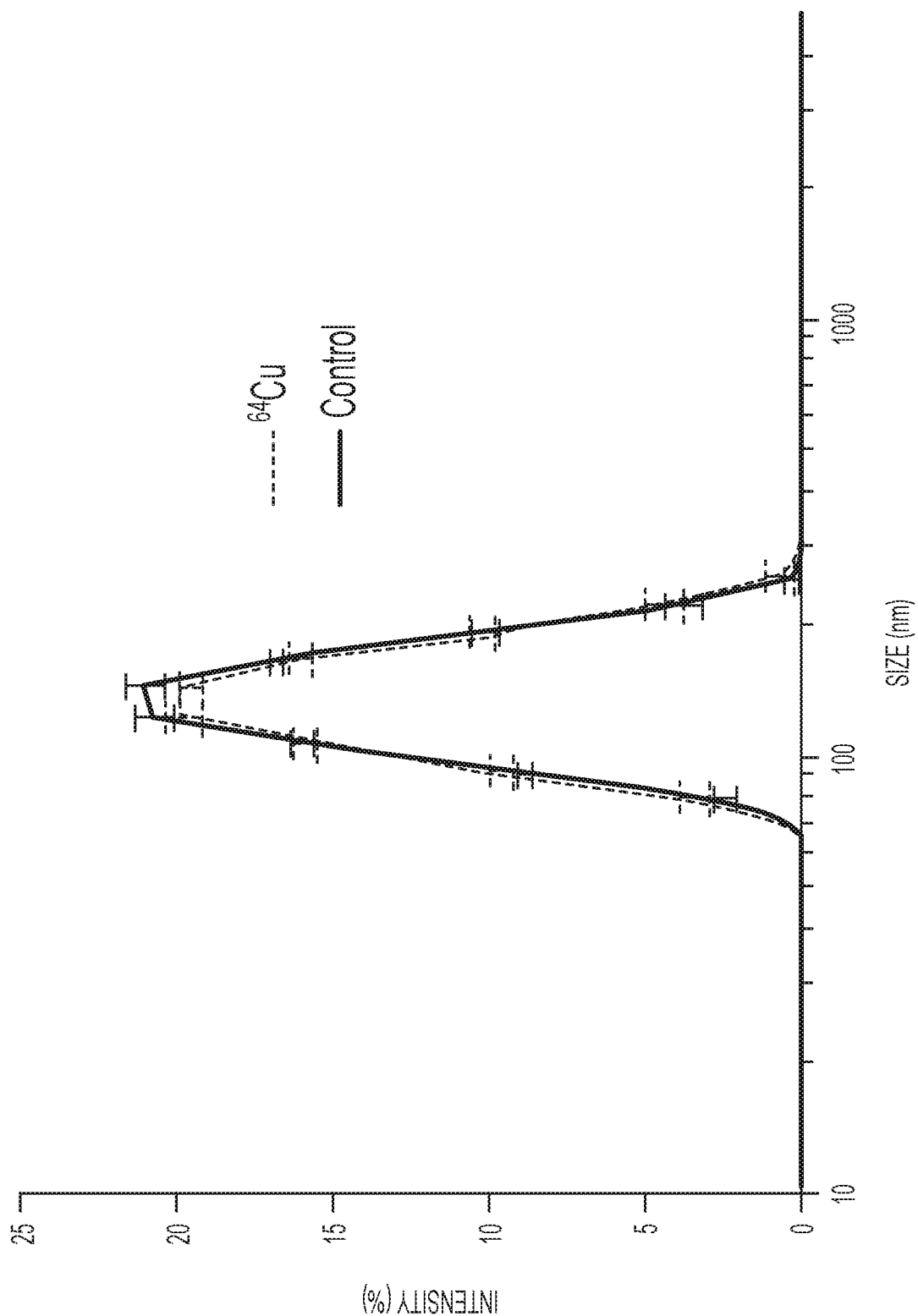
Figure 2C:
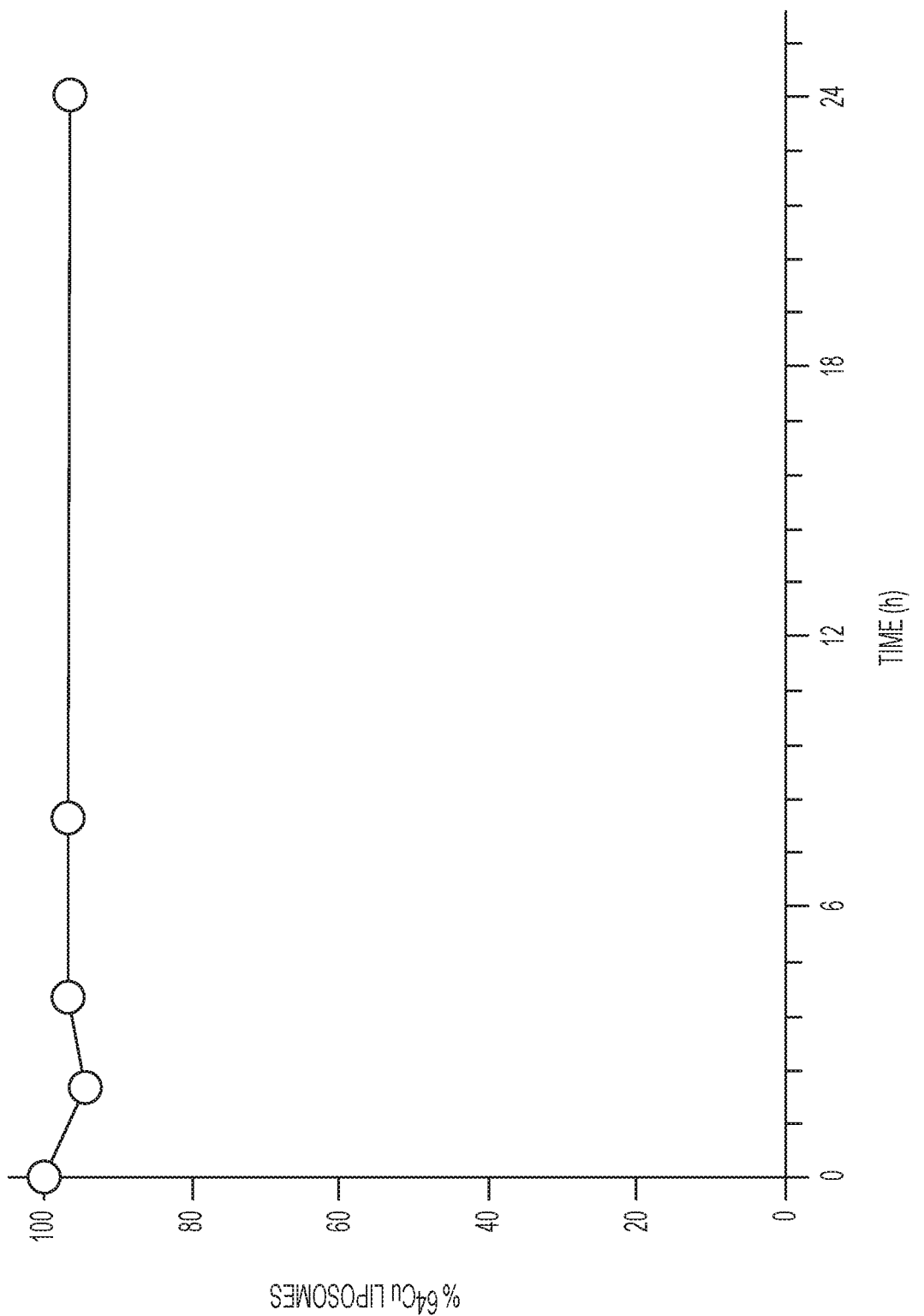

For in vivo experiments, the stability of $^{64}$Cu labeled liposome in serum is shown in FIG. 2C. As shown in FIG. 2C, $^{64}$Cu does not dissociate from DOTA-Bn-DSPE at room temperature for 24 h, indicating that copper labeling of liposomes can be used as a quantitative measurement for liposome accumulation in organs.

Biodistribution and Blood Clearance of Liposomes

The bone marrow targeting efficacy of the liposomes was determined by measuring the biodistribution properties of $^{64}$Cu of major organs including bone marrow, liver, and spleen. Several different liposomes were formulated, characterized, and tested as shown in Table 1. All the liposomes listed show similar size and polydispersity index (PDI), and were stable in size for more than 1 year (data not shown). Liposome #4 was selected due to its negative surface charge and PEG contents, and two different sizes (90 nm and 140 nm) of this liposome were investigated (FIG. 1C). Liposomes that were 90 nm in diameter were selected due to their small size. Liposomes that were 140 nm were chosen to meet a cutoff of 150 nm.

The highest uptake to the bone marrow happened at 24 h after injection with 90 nm size liposomes (15.18±3.69% ID/g). The spleen displayed the highest amount of uptake (34.98±3.16% ID/g). ANOVAs of liposome accumulation to bone marrow was statistically significant with differences between the averages ($p<0.01$), and consecutive multiple comparisons showed that accumulation of 90 nm liposome at 24 h to bone marrow was statistically significant from all the other conditions ($p<0.05$).

Table 1 shows characterization of liposomes of different composition of lipids used for bone marrow targeting.

TABLE 1

| | Composition (input mole ratio) | | | | | | | Zeta Potential |
|---|---|---|---|---|---|---|---|---|
| Lip. # | DSPC | Chol | mPeg-DSPE | Succinyl PE | DSPE-DOTA | Modality | Size (nm) | PDI | (pH = 7.4), mV |
| 1 | 60 | 39 | 0 | 0 | 0.1 | mono | 144.8 | 0.060 | −10.9 |
| 2 | 60 | 39 | 0 | 10 | 0.1 | mono | 154.7 | 0.096 | −32.3 |
| 3 | 60 | 39 | 0.25 | 10 | 0.1 | mono | 143.6 | 0.051 | −29.9 |
| 4 | 60 | 39 | 1 | 10 | 0.1 | mono | 155.0 | 0.060 | −18.8 |
| 5 | 60 | 39 | 2.5 | 10 | 0.1 | mono | 151.3 | 0.057 | −9.5 |
| 6 | 60 | 39 | 1 | 0 | 0.1 | mono | 142.9 | 0.038 | −6.2 |

The liposomes distribution in vivo is influenced by mechanical filtration, membrane fusion, and interaction with serum proteins and their cellular receptors. Specifically, liposome clearance is mostly mediated by a complementary pathway, where liposomes are cleared by the mononuclear phagocyte system (MPS). This complement-mediated pathway is governed by multiple factors, including surface negative charge, cholesterol content, acyl chain saturation and length, and the size of the liposome. When complement binding happens in circulation, liposomes are attached and cleared by the MPS system, especially by Kupffer cells in liver. By modulating the factors governing the complement binding system, the hepatic uptake of liposomes can be lowered and uptake can occur by another MPS system. The result herein support that bone marrow uptake of liposomes is the highest when the liposome has a diameter is at 90 nm and is negatively charged.

Based on these results, liposomes of different size distributions, surface charges, and PEG concentrations were synthesized to identify ideal candidates for drug delivery into the bone marrow. The effect of size on the uptake of liposome in bone marrow can be clearly seen in Table 2 and FIG. 3, which show that 90 nm liposomes show better uptake in comparison to 140 nm liposomes.

Table 2 shows biodistribution of bone marrow targeting liposome labeled with $^{64}Cu$ in mouse. 140 μCi of $^{64}Cu$ labeled liposome was injected via tail vein injection. 9 mice per group were sacrificed at indicated time and major organs were collected and gamma counter was used to measure radioactivity. 9 mice per each group were used and % ID/g was calculated by measuring weight and time corrected measurement of radioactivity.

TABLE 2

| | 90 nm | | 140 nm | |
|---|---|---|---|---|
| | 4 h | 24 h | 4 h | 24 h |
| Blood | 16.59 (±0.95) | 2.17 (±0.46) | 15.19 (±1.82) | 1.56 (±0.42) |
| Heart | 2.79 (±0.43) | 1.22 (±0.14) | 3.07 (±0.20) | 1.06 (±0.20) |
| Lung | 2.83 (±0.30) | 0.87 (±0.15) | 3.52 (±0.40) | 0.85 (±0.16) |
| Liver | 13.87 (±2.81) | 13.78 (±3.16) | 10.12 (±1.62) | 20.11 (±5.16) |
| Spleen | 14.04 (±1.90) | 34.98 (±11.85) | 14.61 (±3.88) | 15.3 (±4.95) |
| Stomach | 0.49 (±0.06) | 0.74 (±0.17) | 1.45 (±0.84) | 0.73 (±0.14) |
| S Intestine | 1.37 (±0.13) | 1.97 (±0.30) | 1.31 (±0.11) | 1.18 (±0.09) |

TABLE 2-continued

|  | 90 nm | | 140 nm | |
| --- | --- | --- | --- | --- |
|  | 4 h | 24 h | 4 h | 24 h |
| L Intestine | 1.21 (±0.19) | 1.4 (±0.19) | 0.89 (±0.14) | 1.2 (±0.20) |
| Kidney | 3.43 (±0.52) | 1.61 (±0.27) | 3.54 (±0.56) | 1.74 (±0.36) |
| Muscle | 0.15 (±0.02) | 0.16 (±0.03) | 0.22 (±0.05) | 0.11 (±0.01) |
| Marrow | 6.5 (±0.72) | 15.18 (±3.69) | 6.86 (±0.77) | 7.01 (±0.92) |

Liposome Accumulate Bone Marrow with Low Tumor Accumulation

Enhanced permeability and retention (EPR) effect refers to how molecules of specific size (nanoparticles or macromolecules) have the tendency to accumulate more in tumor tissue than healthy organs. Without wishing to be bound to theory, the newly formed vessel structure within tumors is leaky, and 30 nm-250 nm particles can escape from the vessel and accumulate in tumor. Antitumor drug Doxil® (liposomal encapsulated Doxorubicin) takes advantage of the EPR effect to deliver higher doses of the drug to the tumor.

Figure 5:
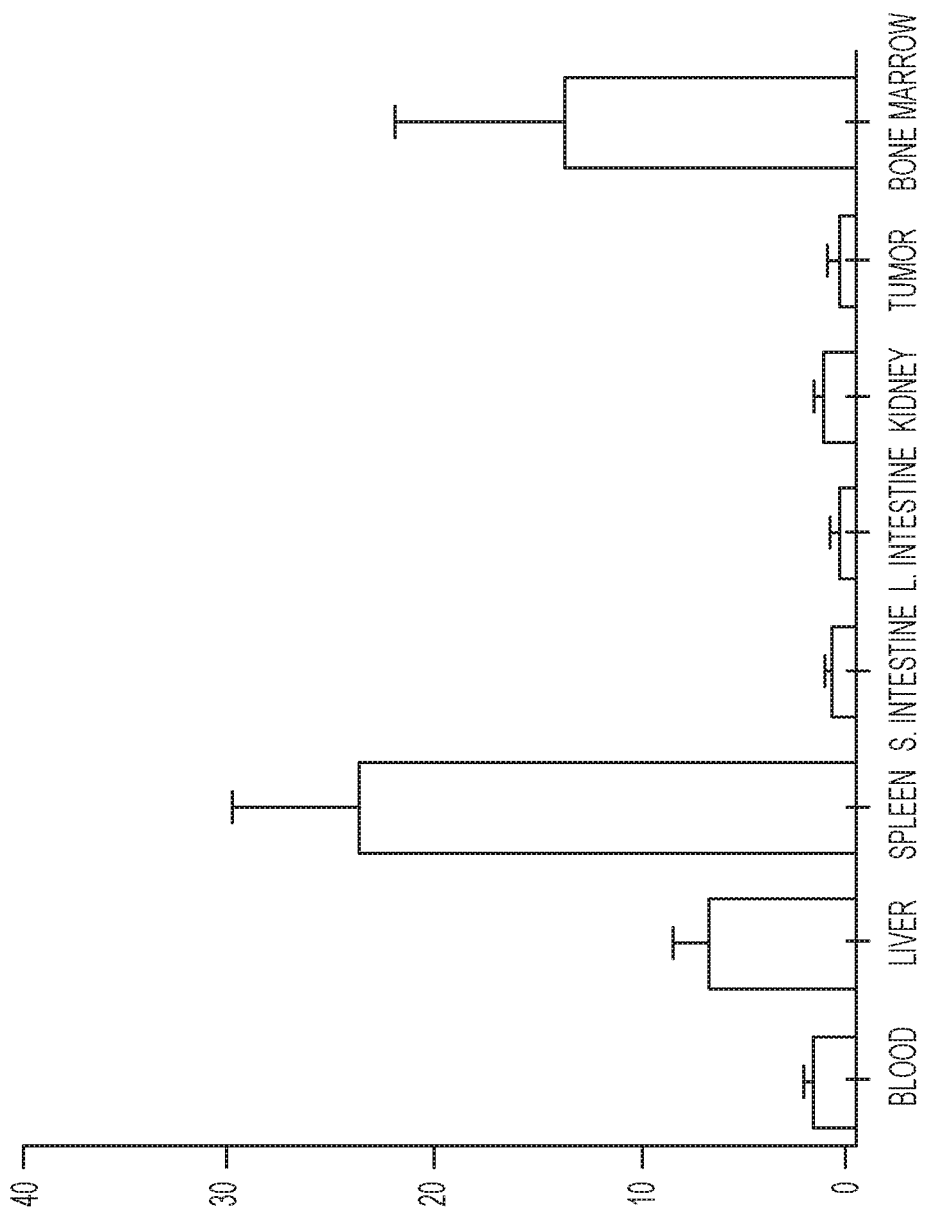
FIG. 5 shows the biodistribution of bone marrow targeting liposome in tumor bearing mice. Bone marrow targeted liposomes are injected into PC9 bearing athymic nude mice at 24 h post administration. There is high bone marrow uptake into bone marrow but low uptake in tumor. The ratio between bone marrow/tumor uptake is 8:5.

As described herein, radioprotectants were selectively targeted to the bone marrow to minimize their delivery to tumor tissue in order to prevent the radioprotectant from reducing the efficacy of radiation treatment on the tumors. Liposome distribution was measured in both the bone marrow and tumor. To evaluate the relative uptake of liposome in tumor and bone marrow, the $^{64}$Cu labeled liposomes were injected into nude mice bearing PC9 (lung tumor) tumor xenografts. As shown in FIG. 5, the 90 nm liposome uptake in PC9 xenografts was about 1.61% ID/g at 24 h post administration in comparison to bone marrow where the accumulation is 13.87% ID/g. The data demonstrates that using this system can achieve a 8.5 fold higher uptake in marrow in comparison to tumor.

Thus, using the liposomal formulation described herein, it is possible to deliver high amounts of radioprotectant to bone marrow without compromising the outcome of radiotherapy of the tumors.

Results

Synthesis of DOTA-Bn-DSPE

Figure 1B:
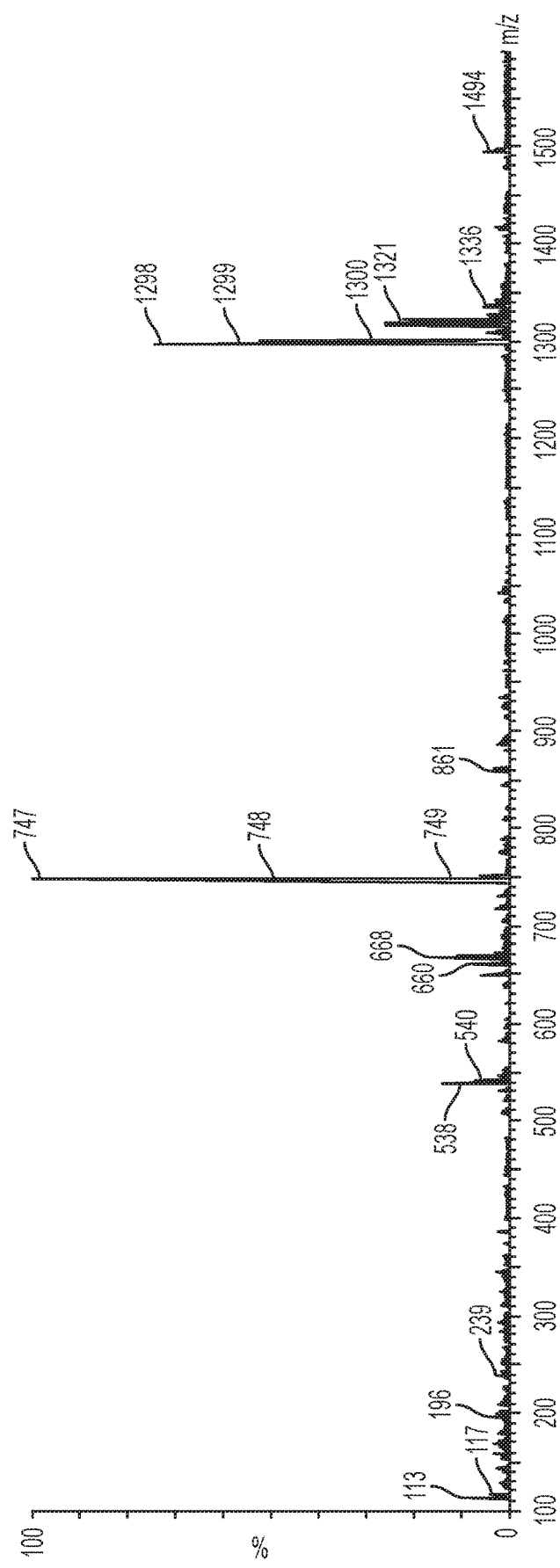
FIG. 1B shows mass spectra of reaction product. DSPE-Bn-DOTA peak appears at 1298 m/z.
Figure 1C:
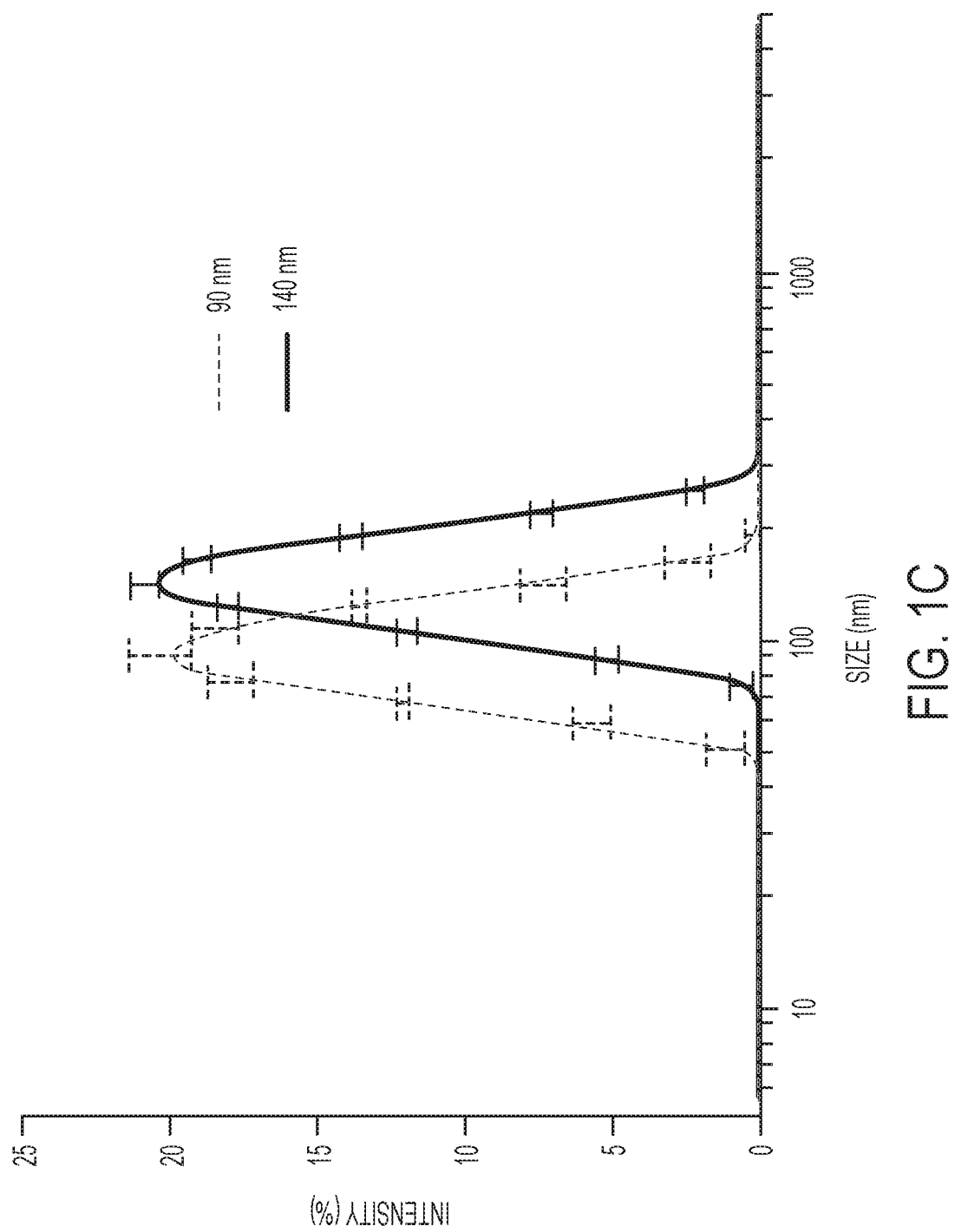
FIG. 1C shows representative size distribution of liposomes observed through dynamic light scattering. For example, 140 nm and 90 nm diameter liposomes are used for the experiments described herein.

DOTA-Bn-DSPE was synthesized by coupling p-SCN-Bn-DOTA and DSPE and identified by mass spectroscopy (FIG. 1). For synthesis, the mole ratio between DSPE and p-SCN-Bn-DOTA was set to 1:2 to ensure all p-SCN-Bn-DOTA was coupled with DSPE. As shown in mass spectrum, [M+H] peak is identified at 1298 m/z and unreacted DSPE peak was identified at 747 m/z. After identifying the main component of the reaction products are p-SCN-Bn-DOTA and DSPE, no further purification step was performed.

Synthesis of DOTA-Bn-DSPE and Succinyl DPPE Containing Liposomes

DOTA-Bn-DSPE and succinyl DPPE comprising liposome were prepared with different concentrations of succinyl DPPE at different sizes (Table 1). Liposomes with 140 nm and 90 nm in diameter were generated with two different pore size membranes using an extrusion method. For example, 140-150 nm diameter liposomes were generated using 100 nm pore size membranes for extrusion, and 90 nm liposomes were generated using 30 nm pore size membranes for extrusion. Both liposomes were predominantly monodisperse and polydispersity indices were 0.038 to 0.096. The zeta potential at pH 7.4 varied from −6.24 mV to −32.37 mV, depending on the liposome composition (Table 1). Higher succinyl DPPE and low PEG DSPE contents contributed to bigger zeta potential and liposome stability. Liposome stability was tested by measuring liposome size. No changes in size distribution were observed for at least 18 months.

$^{64}$Cu and Labeling and Removal of Free $^{64}$Cu $^{64}$Cu labeling to DOTA-Bn-DSPE liposomes was performed at 50° C. for 1 h, at pH 5.5 with shaking. ITLC data shows that the labeling efficiency of $^{64}$Cu is nearly 100%. As shown in FIG. 2B; the size distribution of liposome does not change after $^{64}$Cu incorporation. PD-10 column or PD MiniTrap G-25 column with PBS was used to remove unbound $^{64}$Cu and to adjust the pH of reaction solution from pH 5.5 to pH 7.4.

Serum Stability of $^{64}$Cu Labeled Liposome and Blood Clearance

Figure 3A:
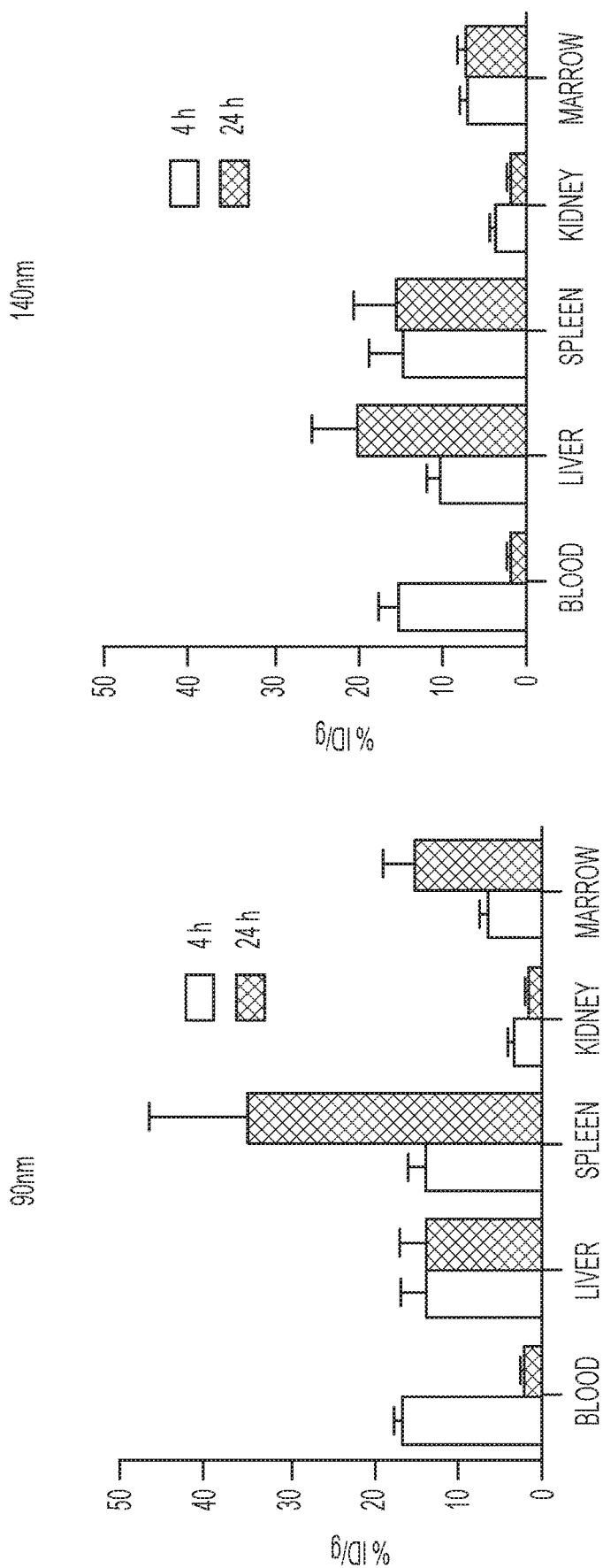
FIGS. 3A-3B show the biodistribution of bone marrow targeting liposomes labeled with $^{64}$Cu and blood clearance of the labeled liposomes.
Figure 3B:
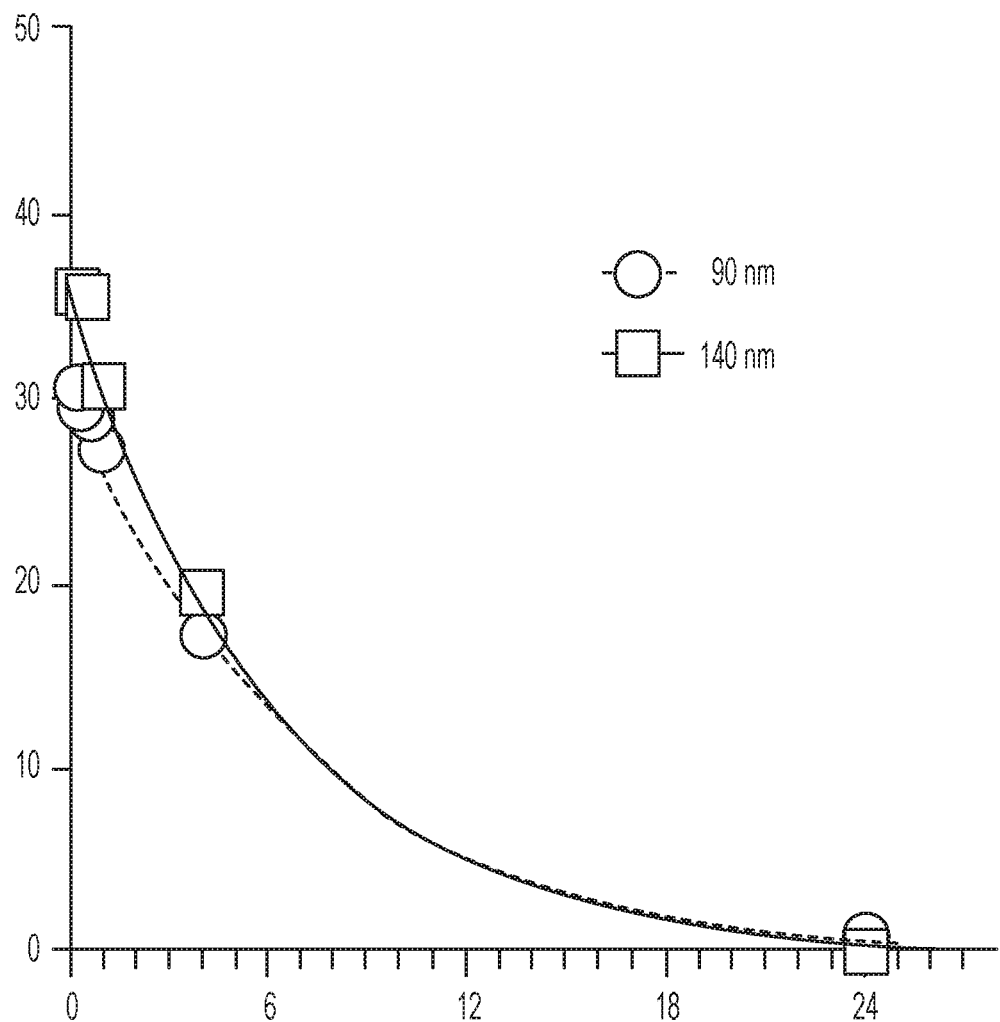

The serum stability of the $^{64}$Cu-DOTA-Bn-DSPE liposomes was measured by incubating the radiolabeled liposome in 50% serum at 37° C. for 24 h. The leaching of copper and/or loss of [$^{64}$Cu]-DOTA-Bn-DSPE from the liposome was measured using ITLC, and the results are summarized in FIGS. 3A-3B. As shown in FIGS. 3A-3B, the $^{64}$Cu labeled liposome is highly stable in the serum for up to 24 h with little loss of radioactivity from the liposome. Blood clearance of liposome was measured by extracting blood from mouse tail at a given time after $^{64}$Cu labeled liposome was injected via the tail vein. The half-life of blood clearance was calculated using one-phase decay of 90 nm was 4.6±1.9 h and 140 nm was 4.2±0.8 h.

Biodistribution of $^{64}$Cu Labeled Liposomes

The ex vivo biodistribution data of $^{64}$Cu labeled liposomes with the sizes of 90 nm and 140 nm at 4 h and 24 h, respectively, are presented in Table 2. This data shows that both liposomes accumulate in the bone marrow. Although both liposomes accumulate in bone marrow with equal efficiency (about 6.5% ID/g at 4 h) at early time points, at 24 h post administration, 90 nm liposomes accumulate preferentially in the bone marrow at a higher concentration compared to the 140 nm liposomes. The corresponding % ID/g values are 15.18±3.69 and 7.01±0.92 for 90 and 140 nm liposomes, respectively. In addition to bone marrow, the other RES organs (e.g., the liver and spleen) show high uptake of the liposomes. However, without having to be bound by theory, the time dependent uptake in liver and spleen appears to be dependent on the size of liposomes. For the 90 nm liposome, the liver uptake remains similar at 4 h and 24 h with % ID/g values of 13.87±2.81 and 13.78±3.16, respectively. The spleen uptake reflects a pattern similar to bone marrow uptake, with increasing accumulation at later time points, or values of 14.04±1.90 and 34.98±11.85 at 4 h and 24 h respectively. The corresponding values observed in the spleen for 140 nm liposomes were 14.61±3.88 and 15.3±4.95, at 4 h and 24 h respectively, indicating early targeting and retention in the spleen. In contrast, the uptake of 140 nm liposomes in liver shows a significant increase at 24 h with % ID/g values being 10.12±1.62 and 20.11±5.16 at 4 h and 24 h, respectively. It is noted that the blood uptake and clearance value for both 90 and 140 nm liposomes is essentially the same. Based on the data herein, the 90 nm liposome is better suited for bone marrow targeting applications.

Static and Dynamic MicroPET Images of Animals Injected with Bone Marrow Targeting Liposomes and Pharmacokinetic Analysis of $^{64}$Cu Labeled Bone Marrow Targeting Liposome The representative biodistribution of $^{64}$Cu-DOTA-Bn-DSPE liposomes 24 h post administration is displayed in FIGS. 4A-4C. FIG. 4A shows the maximum intensity projection image of bone marrow targeting liposomes. As shown in biodistribution data, the strongest signal was in the liver and spleen. Despite relatively high uptake in bone marrow (~15.8% ID/g) the signal appears relatively weak, due to the fact that the mass of bone marrow is very low (typical bone marrow extracted from the femur of 4-6 week old mice is about 3-5 mgs). Low signal in the bone marrow was also due to the partial volume effect from small bone marrow volumes which causes activity spillover to neighboring regions and thereby reducing the observed intensity in the bone marrow. Despite these limitations, the sacrum, spine, the femoral and tibial heads can be clearly delineated from the image.

Figure 6B:
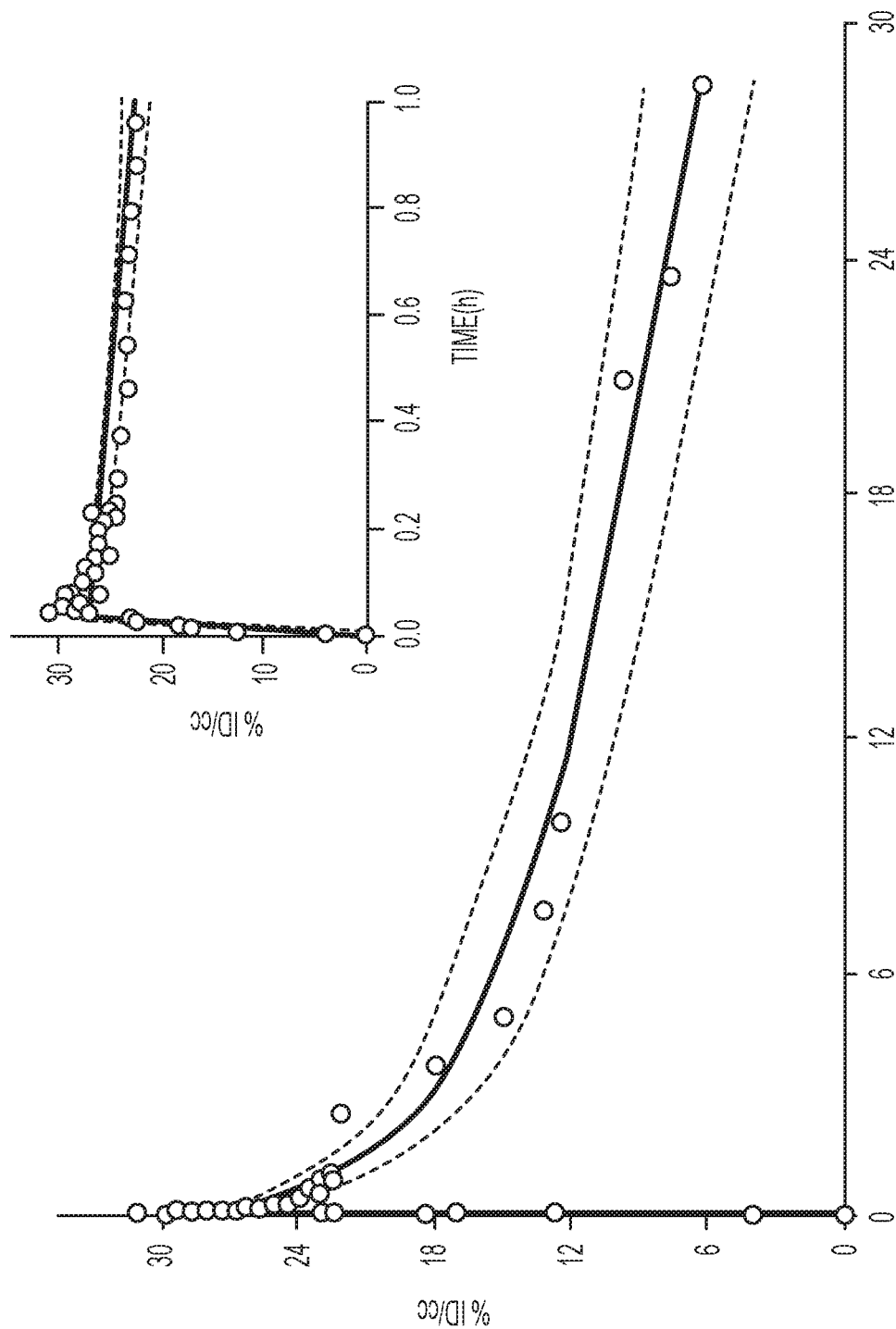

Pharmacokinetic Analysis of $^{64}$Cu Labeled Bone Marrow Targeting 90 nm Liposome Using Dynamic MicroPET Imaging Dynamic microPET imaging set at 1 h was used to evaluate early biodistribution profile of the 90 nm bone marrow targeting liposomes. After tail vein injection, liposomes were rapidly distributed in vascular compartment. As shown in FIG. 6, blood activity reaches its maximum uptake at 200 sec when infusion of liposome finishes. Following this event, the radioactivity in the blood then lowers. Liver uptake of liposomes reached its maximum around 3-4 h, and the activity accumulation in the liver remains similar until 28 h. Spleen uptake of liposome was rapid until 1 h after tail vein injection and slowly increased its activity until 28 h. Spleen uptake did not have a fast uptake, unlike the liver, during infusion but increased its activity at a relatively similar speed. Both liver and spleen uptake of liposome reflected the rapid initial clearance of liposomes from the blood circulation by liver Kupffer cells and splenic macrophages.

Frequent arterial blood sampling is typically used to measure blood concentration and circulation of radioactive material, but arterial blood sampling is invasive and a laborious process with small animals. It is also difficult if the clearance is fast and requires frequent sampling at early time points after injection. Therefore, the time activity curve derived by ROIs of large vascular structure, such as the heart from PET imaging was used to estimate the concentration of radioactivity in the blood. Pharmacokinetics parameters of $^{64}$Cu labeled bone marrow targeting liposome after tail vein injection were derived using a 2-compartment model. The volume of distribution ($V_d$) and elimination rate constant (k) are 3.51 mL and 0.063 h$^{-1}$, respectively, and other pharmacokinetic parameters are summarized in Table 3.

Table 3 shows pharmacokinetic parameters derived from two compartment models of $^{64}$Cu labeled bone marrow targeted liposomes in mice. $k_{12}$=the distribution rate constant from compartment 1 to compartment 2, $k_{21}$=the distribution rate constant from compartment 2 to compartment 1, $V_d$=volume of distribution, k=the elimination rate constant, CL=the clearance of elimination, Q=inter-compartmental clearance, AUC$_\infty$=area under the curve.

TABLE 3

| $k_{21}$ (h$^{-1}$) | $k_{12}$ (h$^{-1}$) | $V_d$ (mL) | k (h$^{-1}$) | CL (mL/h) | Q (% ID/h) | AUC$_\infty$ (h/mL) |
|---|---|---|---|---|---|---|
| 1.96 | 0.52 | 3.51 | 0.063 | 0.22 | 1.83 | 288 |

Delivery of RNAi-Based Therapeutics

Delivery of RNA interference (RNAi) therapeutics to target an organ is a major challenge due to many factors including degradation by serum nucleases, recognition and clearance by immune system, non-specific interaction, and fast blood clearance. This is further complicated by the fact that RNAi has to be delivered intracellularly for achieving a pharmacological effect.

Liposome-based nanocarriers described herein can be used to deliver RNAi therapeutics selectively to immune system organs such as lymph nodes and spleen. In certain embodiments, the RNAi can be packaged inside the liposomal formulation. In certain embodiments, the RNAi can be packaged outside the lipid bilayer. Incorporation of RNAi therapeutic into the liposome can prevent degradation of RNAi by cellular/serum proteins. Preventative degradation increases bioavailability of the therapeutic.

Liposomal formulations have been employed to target tumors or organs. However, no examples of selective delivery of RNAi therapeutics to bone marrow or lymph nodes exist. In certain embodiments, the liposome-based nanocarriers described herein are used for delivery RNAi to the lymph nodes and/or bone marrow with high efficiency. The examples of RNAi drugs that can be used include but are not limited to GTI-2040 (ribonucleotide reductase), SPC2996 (Bcl-2) (ClinicalTrials.gov Identifier: NCT00285103), LY2181308 (survivin), and similar drugs, for treating acute myeloid leukemia (AML) and chronic myeloid leukemia (CML).

The delivery of drugs to marrow and lymph nodes is critical in conditions such as sepsis, where the immune system is hyper-activated and engages in anti-host response. Another potential application includes Graft-versus-Host-Disease (GVHD), where the transplanted immune system (from donor) may cause auto immune disease in the host. Under these conditions, the drug-loaded liposome-based nanocarriers can be used for delivery of immune suppressors such as Tacrolimus, mTOR inhibitors, corticosteroids, antibiotics, epinephrine analogs, RNAi against Bim and PUMA (Shock. 2009 August; 32(2): 131-139.) and the like to spleen, liver, bone marrow and/or lymph nodes.

Moreover, the liposome-based nanocarriers can deliver drugs to prevent occurrence of bone metastasis or osteoporosis. Therapeutics that can be used to treat osteoporosis include but are not limited to bisphosphonates (e.g., alendronate, ibandronate, Risedronic acid, zoledronic acid), selective estrogen receptor modulators (e.g., raloxifene), parathyroid hormone (e.g., teriparatide), and biologicals (e.g., denosumab).

Table 4 shows chemical structures and IUPAC name of exemplary small molecule drugs that can be used to treat osteoporosis.

TABLE 4

| Drug name | Chemical structure | IUPAC name |
|---|---|---|
| Alendronate | 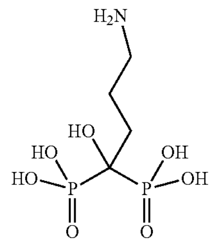 [SMILES: NCCCC(O)(P(=O)(O)O)P(=O)(O)O] | sodium [4-amino-1-hydroxy-1-(hydroxy-oxido-phosphoryl)-butyl]phosphonic acid trihydrate |
| Ibandronate | 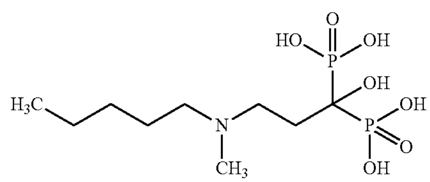 [SMILES: CCCCCN(C)CCC(O)(P(=O)(O)O)P(=O)(O)O] | {1-Hydroxy-3-[methyl(pentyl)amino]propane-1,1-diyl}bis(phosphonic acid) |
| Risedronic acid | 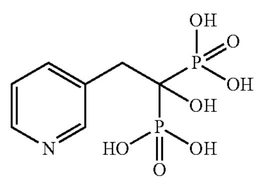 [SMILES: O=P(O)(O)C(O)(Cc1cccnc1)P(=O)(O)O] | (1-hydroxy-1-phosphono-2-pyridin-3-yl-ethyl)phosphonic acid |
| Zoledronic acid | 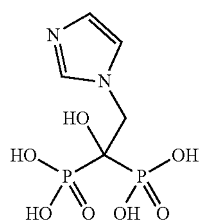 [SMILES: O=P(O)(O)C(O)(Cn1ccnc1)P(=O)(O)O] | [1-hydroxy-2-(1H-imidazol-1-yl)ethane-1,1-diyl]bis(phosphonic acid) |
| Raloxifene | 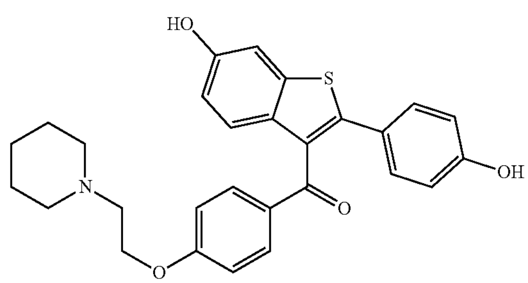 [SMILES: O=C(c1ccc(OCCN2CCCCC2)cc1)c1c(-c2ccc(O)cc2)sc2cc(O)ccc12] | [6-hydroxy-2-(4-hydroxyphenyl)-benzothiophen-3-yl]-[4-[2-(1-methanone |

Liposome-Loaded with Drug for Delivery In Vivo

Figure 11:
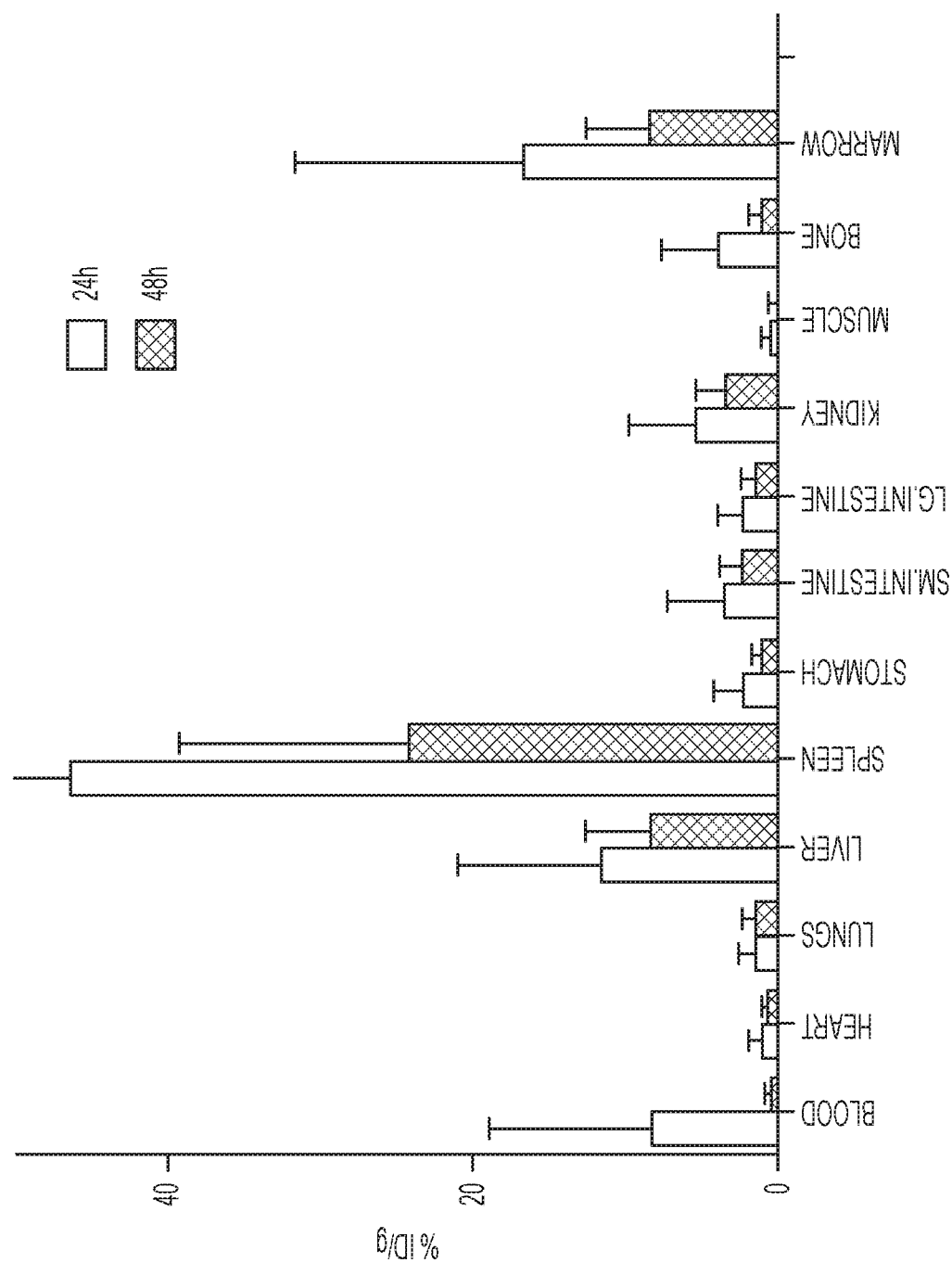
FIG. 11 shows bone marrow accumulation of liposome is 16.6% ID/g at 24 h post injection. Bone marrow accumulation is similar to bone marrow targeting liposome without GT3 incorporation into the liposome.
Figure 12:
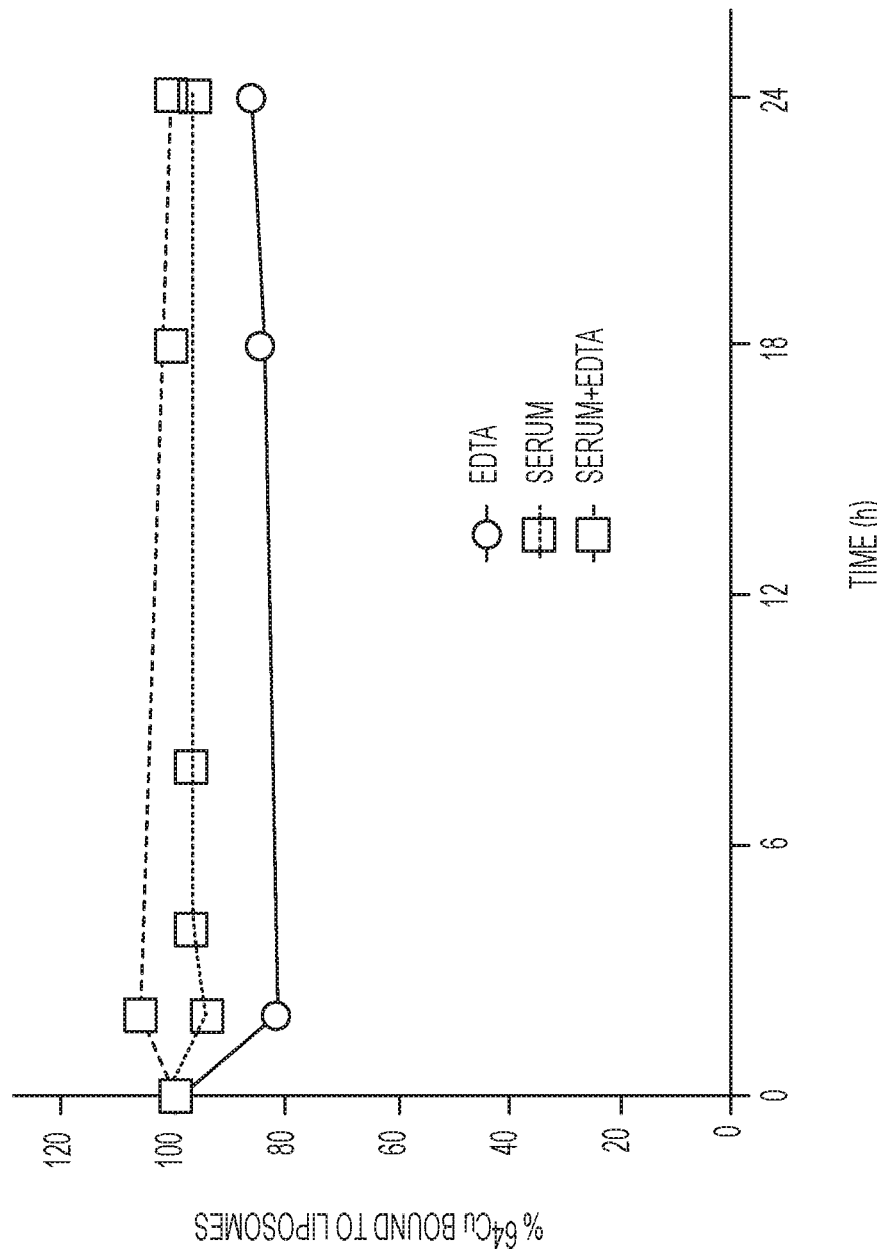
FIG. 12 shows a stability profile of $^{64}$Cu-labeled DOTA-Bn-DSPE liposomes. Synthesis scheme and size distribution of the labeled liposomes are shown in FIGS. 1A, 1C, and 2B, respectively.
Figure 13A:
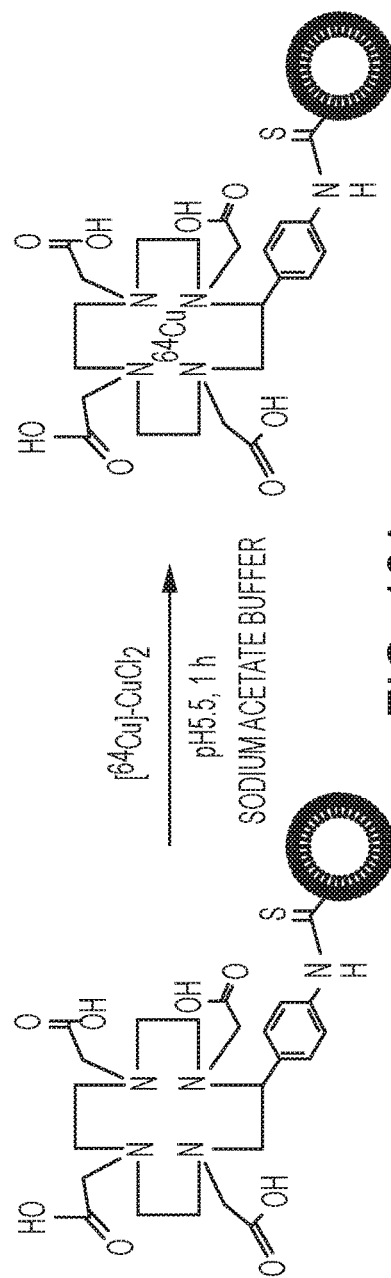
FIGS. 13A and 13B show $^{64}$Cu labeling scheme of liposomes (FIG. 13A) and instant thin layer chromatography (ITLC) characterization (FIG. 13B).
Figure 13B:
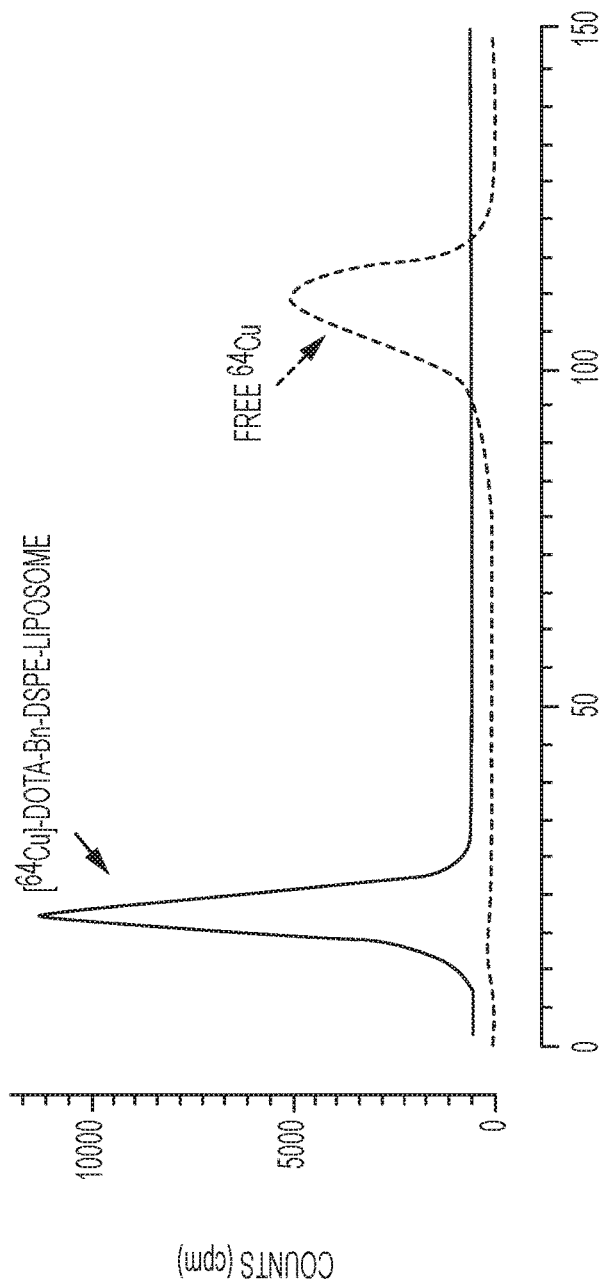
Figure 14A:
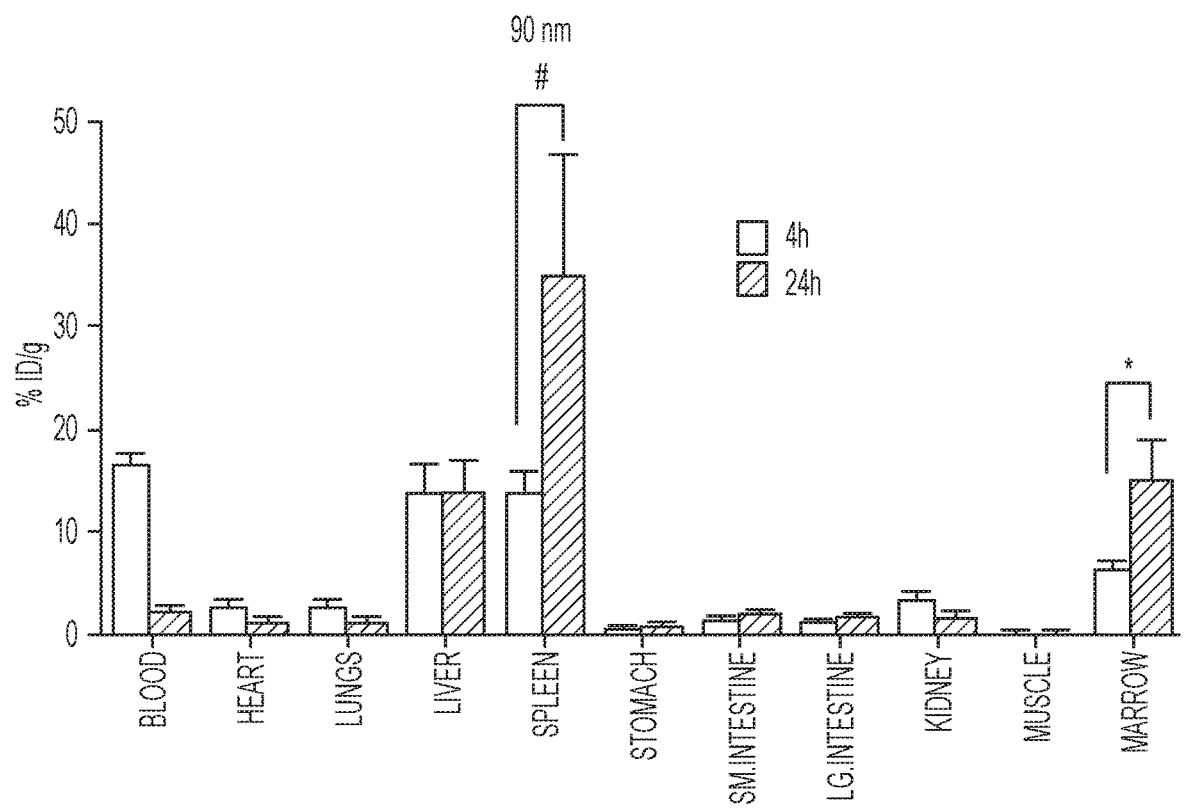
FIGS. 14A and 14B show ex vivo biodistribution data of $^{64}$Cu-labeled 90 nm and 140 nm bone marrow targeting (BMT) liposomes. Biodistribution data in athymic nude mice (n=9) of 90 nm liposomes (FIG. 14A) and 140 nm liposomes (FIG. 14B) at 4 h and 24 post injection. * p<0.5, # statistically insignificant.
Figure 14B:
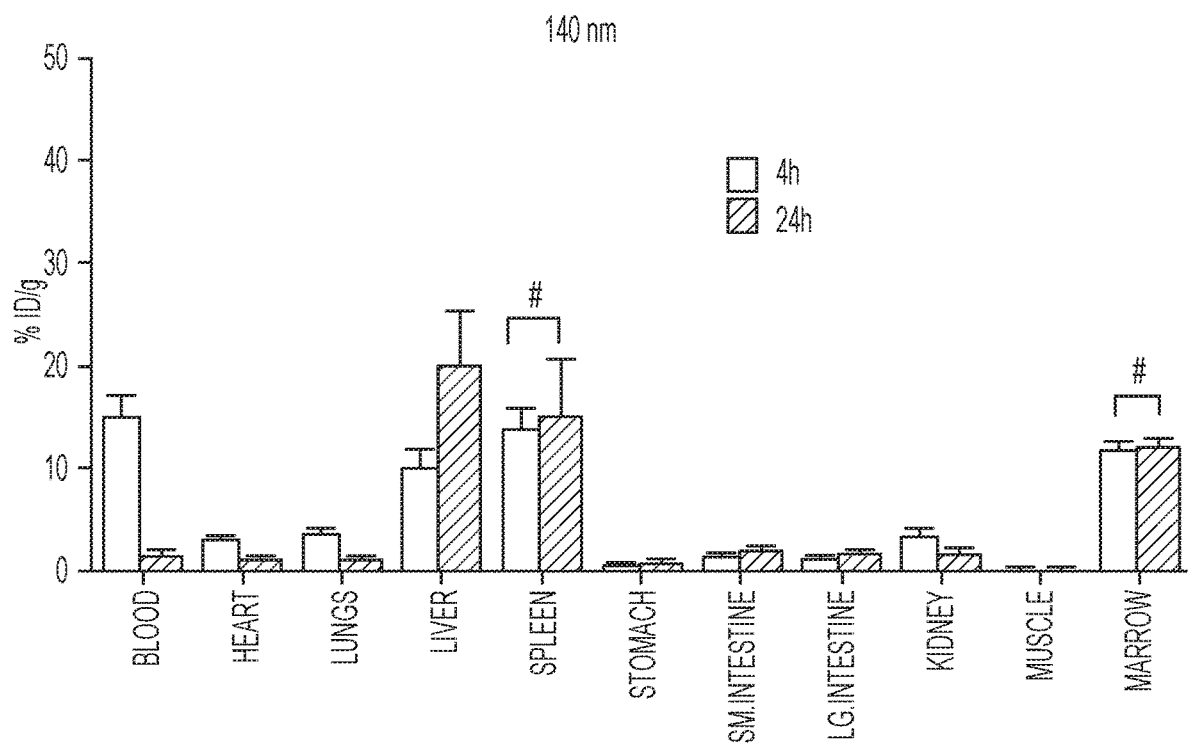
Figure 15:
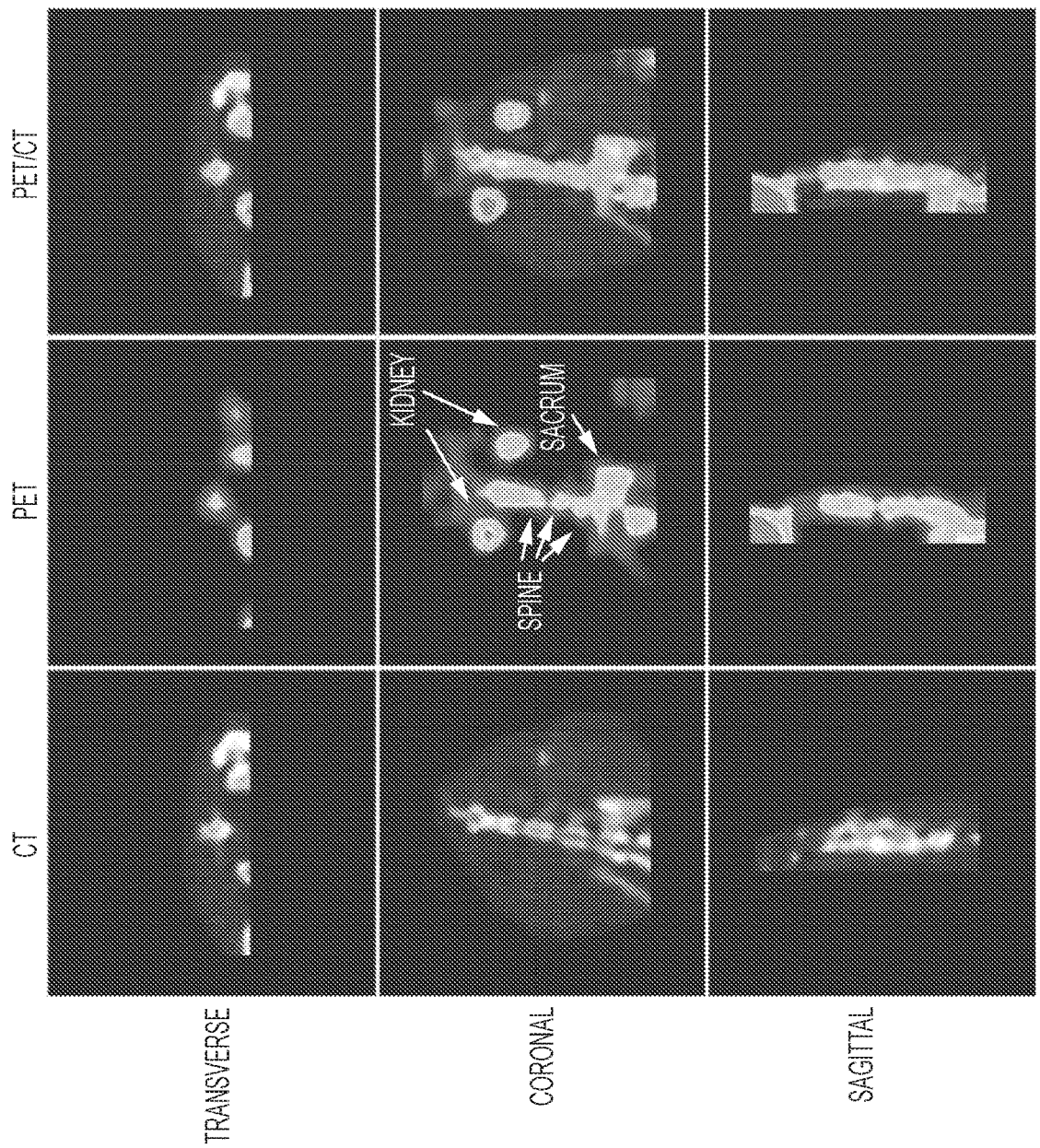
FIG. 15 shows magnified images showing CT, PET/CT fusion, and PET images of spine and sacrum of the same plane (coronal) in a mouse after injection of 140 µCi of $^{64}$Cu-labeled 90 nm liposomes.
Figure 16:
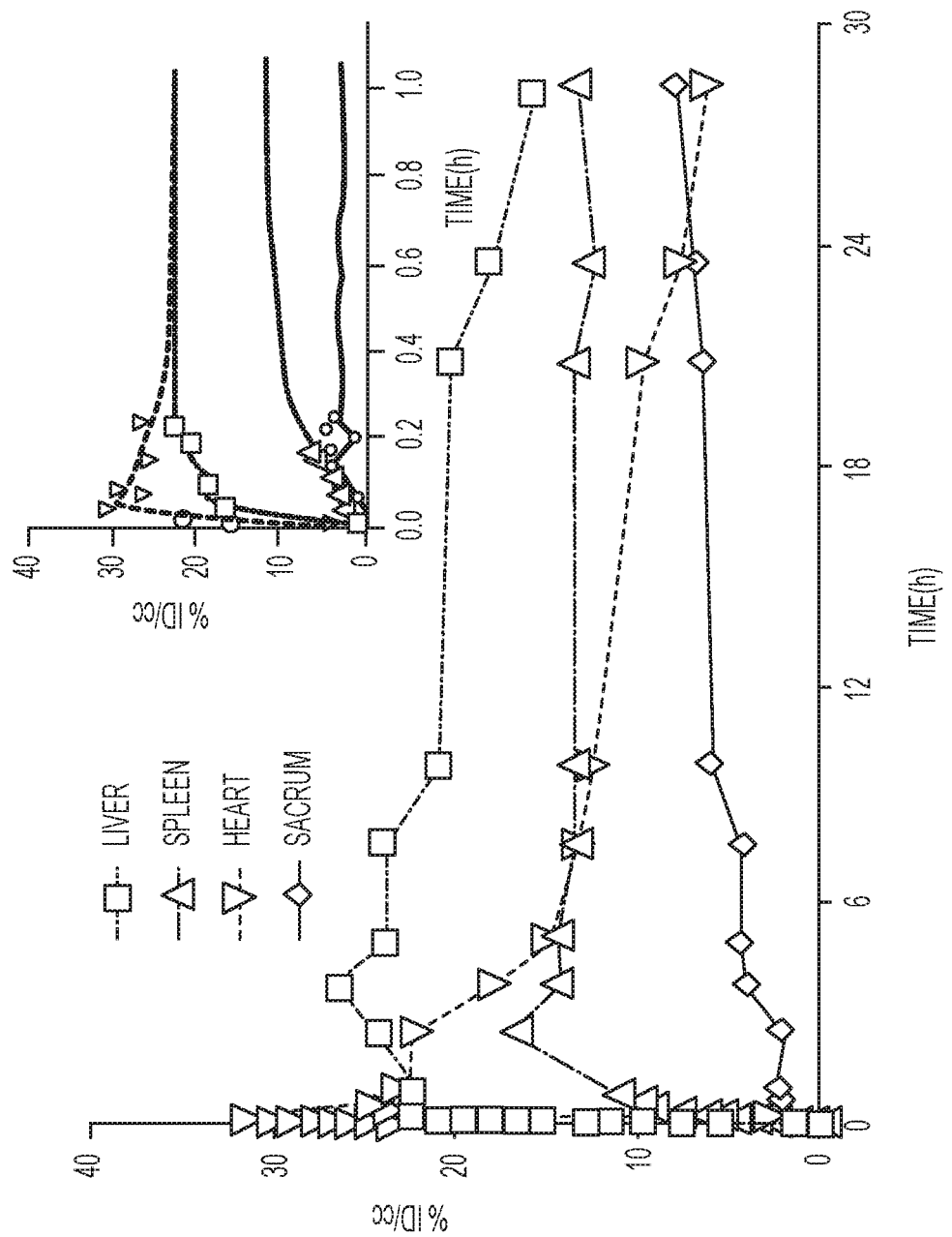
FIG. 16 shows a normalized time activity curve constructed from a region of interest (ROI) drawn around heart, liver, spleen, and sacrum from the image of 1 h dynamic PET scanning combined with static PET images of 2.5, 3.7, 5, 7.5, 10, 20, 24, and 28 h. Motion artifact, partial volume effect, attenuation, scattering correction have not been applied for driving these parameters.
Figure 17:
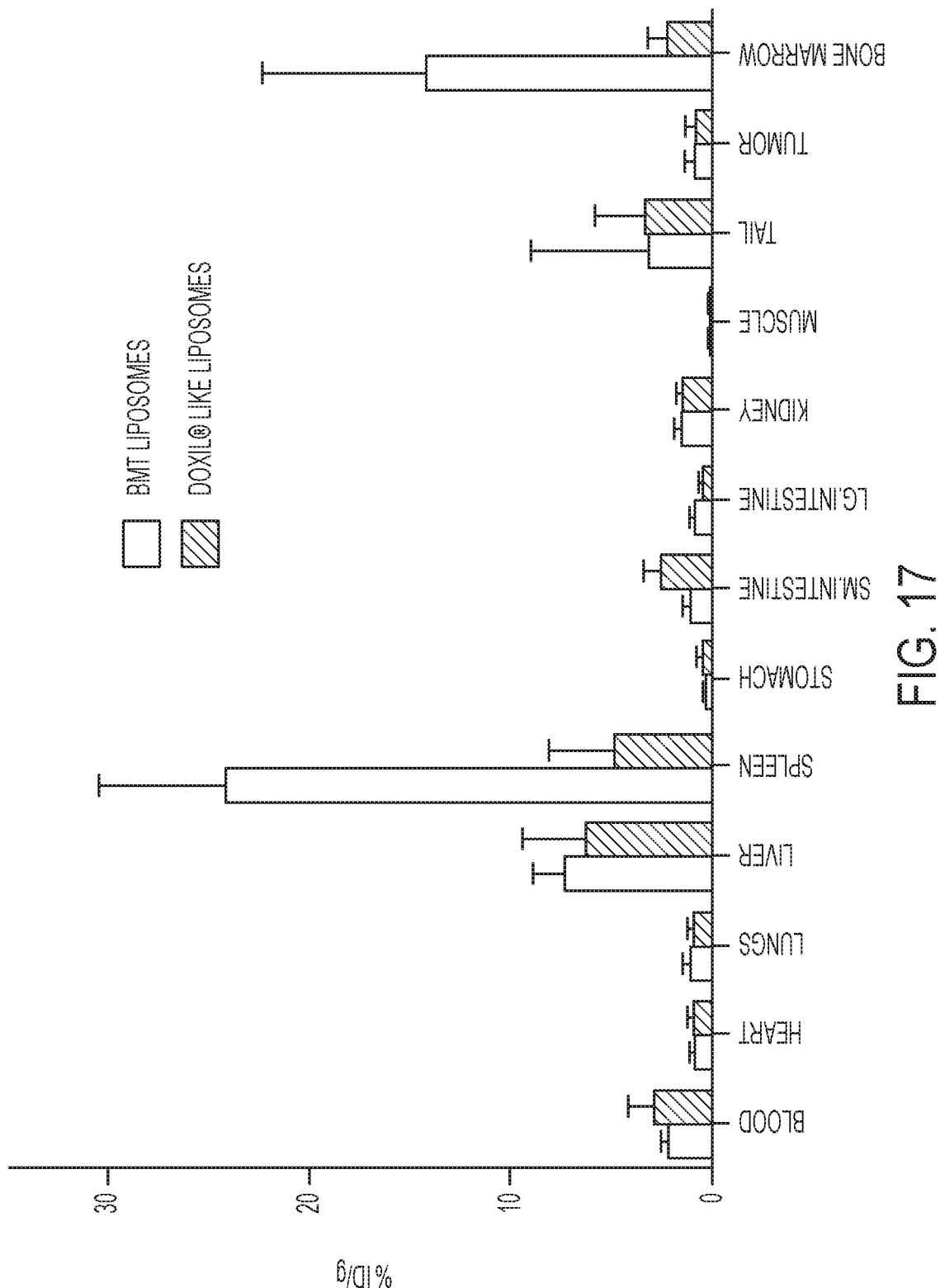
FIG. 17 shows ex vivo biodistribution data of bone BME and Doxil® like liposomes. Biodistribution data of $^{64}$Cu-labeled 90 nm liposomes in PC9 tumor bearing athymic nude mice (n=5) 24 h post i.v. administration. The data presented in FIG. 17 shows that BMT liposomes specifically target bone marrow compared to a liposomal formulation used to deliver drug into tumor, DOXIL. DOXIL is a phosphatidylcholine-based liposome containing doxorubicin for treatment such as ovarian cancer.
Figure 18:
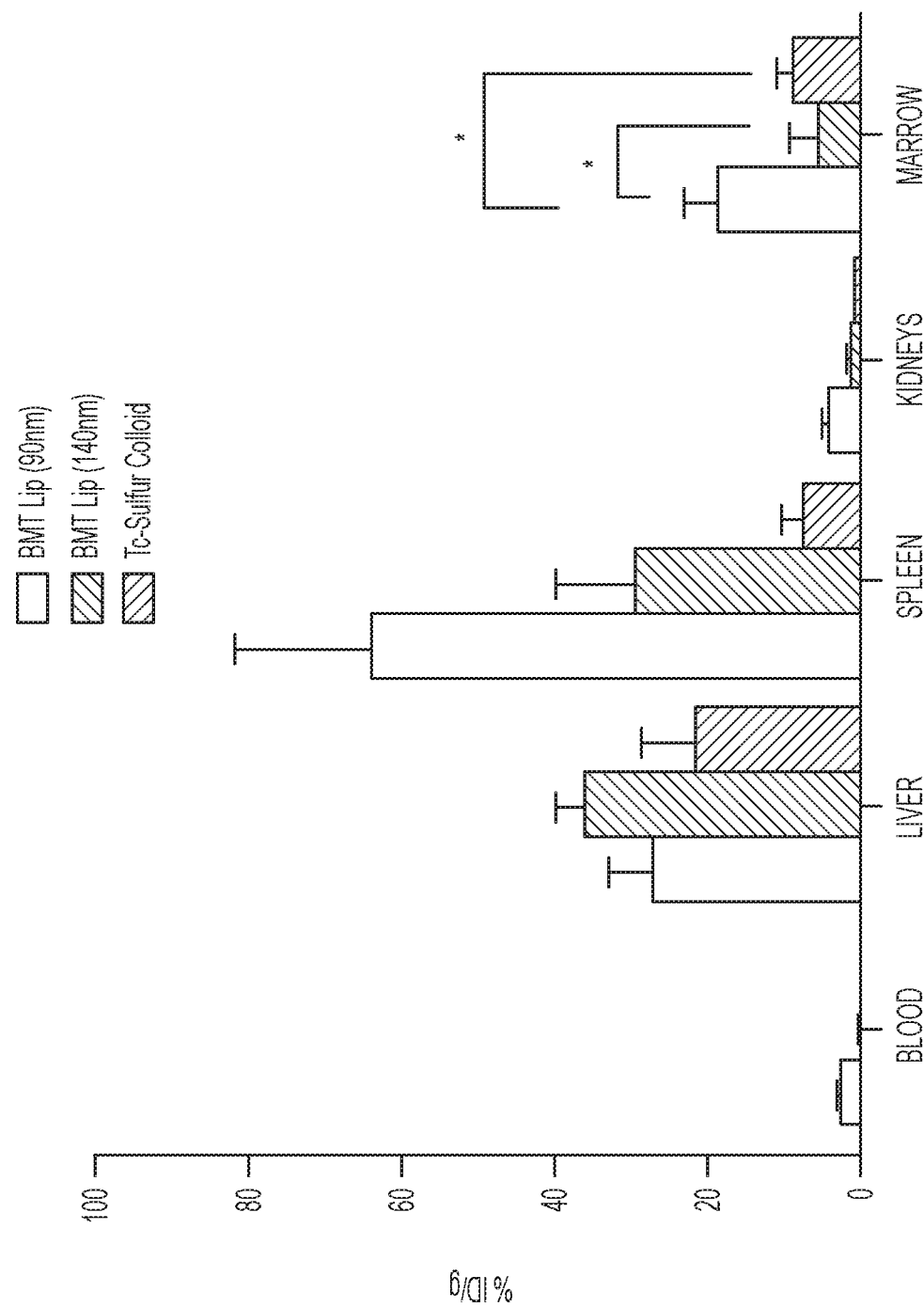
FIG. 18 shows ex vivo biodistribution data of BMT liposomes and $^{99m}$Tc-Sulfur colloid. 90 nm BMT liposomes show higher marrow accumulation than $^{99m}$Tc-Sulfur colloid. * p<0.05

10% (moles/moles) GT3 was added into a lipid mixture and dried to form lipid film and was loaded into the liposome-based nanocarriers described herein. Bone marrow accumulation of liposome is 16.6% ID/g at 24 h post injection and is similar to bone marrow targeting liposome without GT3 incorporation into the liposome. Biodistribution data revealed a concentration of 2.7% ID/g (via $^{131}$I) (or about 54 µM in bone marrow). When $^{64}$Cu is used, biodistribution data revealed that a concentration of 320 µM targeted the bone marrow. (FIG. 11).

In certain embodiments, NAC is loaded into the liposome-based nanocarriers described herein. Data revealed that NAC was rapidly released from the liposome-based nanocarrier. Without taking into account fast release kinetics and only based on encapsulation efficiency and $^{64}$Cu biodistribution data, the concentration of NAC in bone marrow can reach 450 µM or higher.

Targeting Lymph Nodes

To maximize the immune response, an antigen has to be presented to immune cells. In traditional targeting, antigens in combination with adjuvants or particles/carriers coated with adjuvants can be delivered using subcutaneous (s. c.) injections. The limitations of such an approach include that only the lymph nodes (containing immune cells, antigen presenting cells and their B-cell partners) present near the site of injection are targeted. In order to maximize the probability of antigen presentation and subsequent immune response, multiple site targeting needs to be achieved.

Using PET imaging these lymph node targeting liposomes might be useful in identifying tumor infiltrated/metastatic lymph nodes by showing lack of accumulation at these sites indicating presence of tumor mass.

Figure 9:
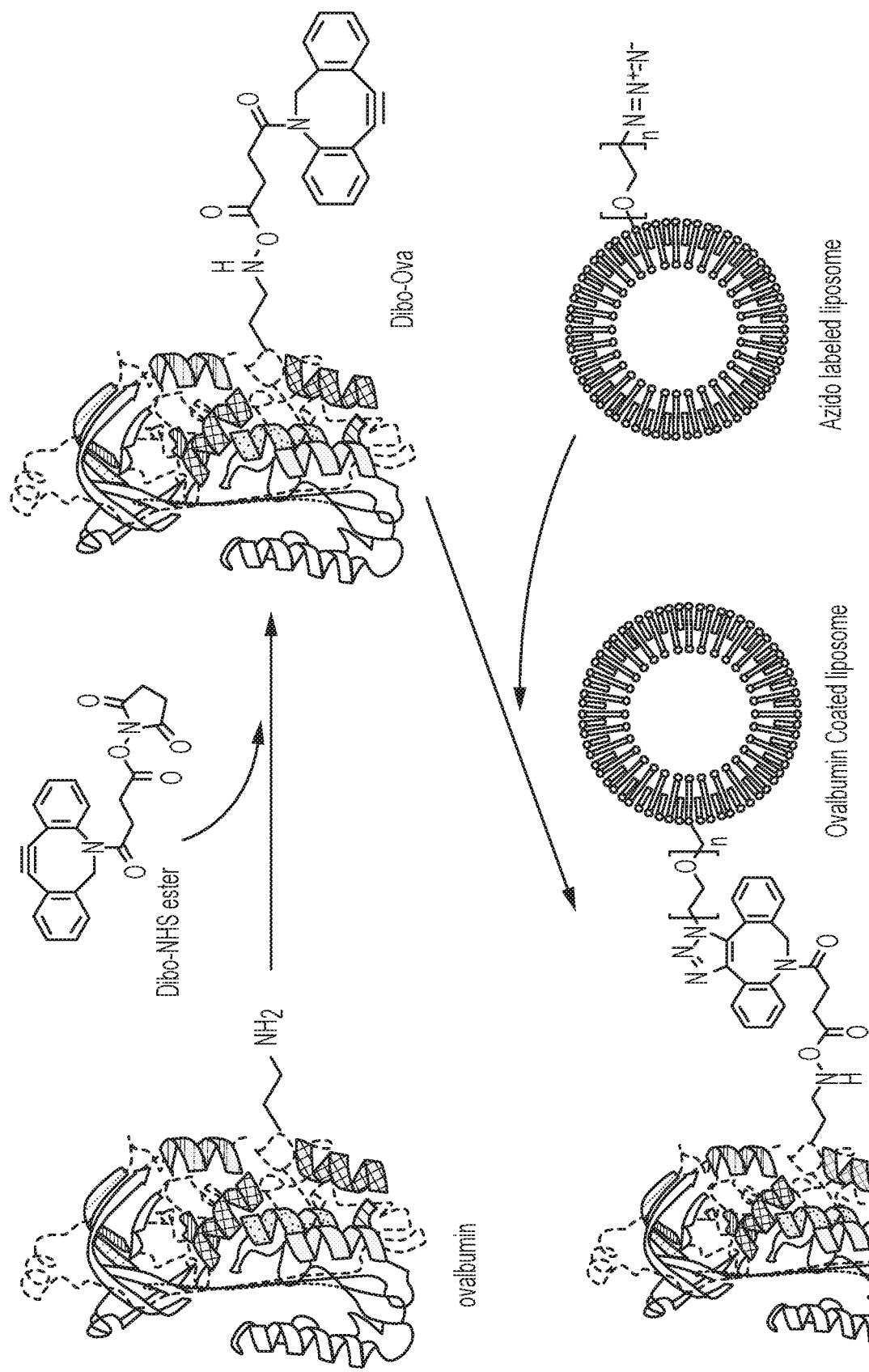
FIG. 9 shows a schematic of the synthesis of ovalbumin-labeled lymph node targeting liposome-based nanocarriers.
Figure 10B:
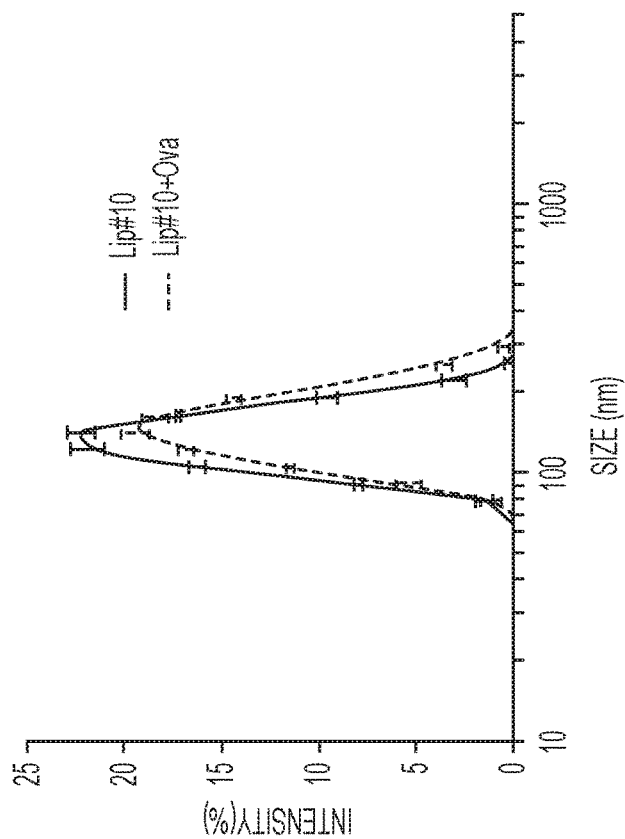
FIGS. 10A-10C show coupling of DIBO-Ova and azido-labeled liposome-based nanocarriers targeting lymph nodes.
Figure 10C:
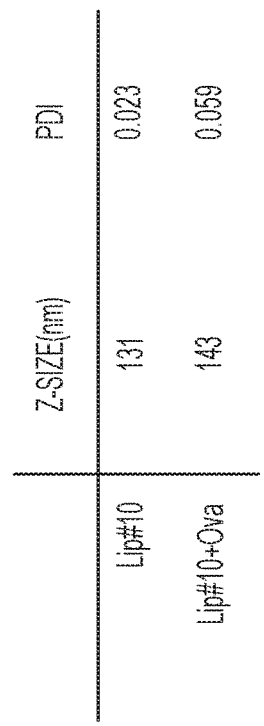
Figure 10A:
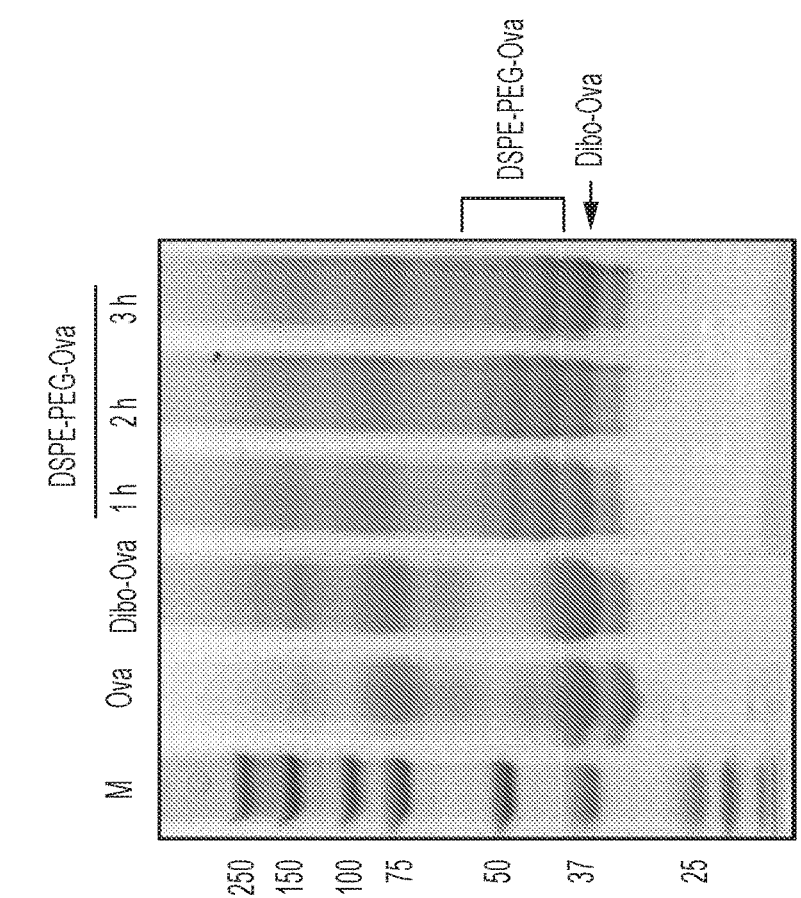

The liposome-based nanocarriers described herein can target major lymph nodes post i.v. administration. The antigen loading/conjugation on the surface of the liposome was achieved using a click chemistry approach to obtain ovalbumin coated liposomes. FIG. 9 shows a schematic of the synthesis of ovalbumin-labeled lymph node targeting liposomes. The surface of liposome was modified to contain an azide (PEG-azide) and the antigen (ovalbumin) was modified with DIBO-NHS ester (Dibenzocyclooctyne-N-hydroxysuccinimidyl ester). The conjugation was achieved by incubating the liposome with DIBO-Ovalbumin at room temperature (RT) for 1 h followed by purification using size exclusion chromatography (FIGS. 10A-10C).

Figure 7:
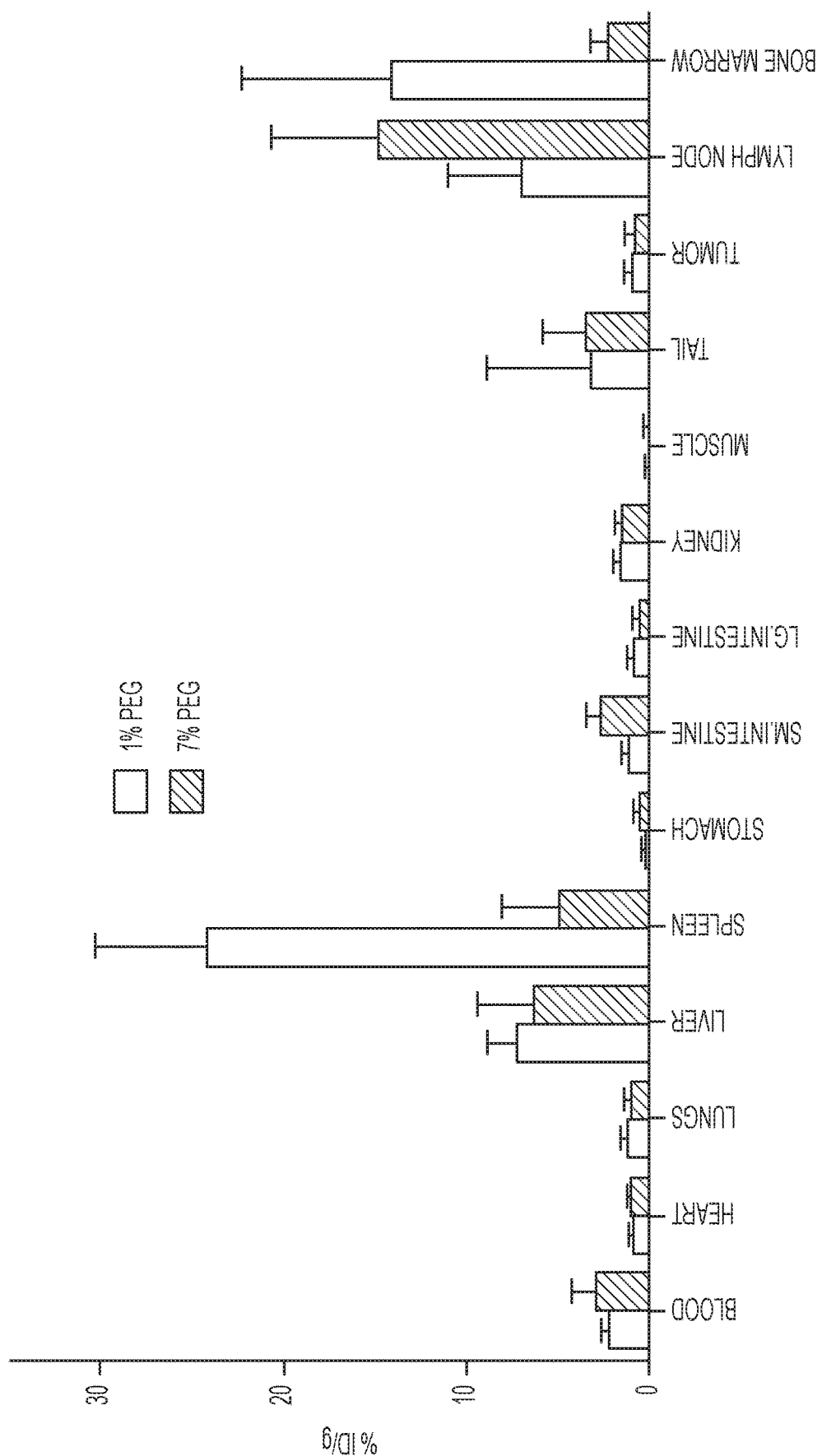
FIG. 7 shows biodistribution of lymph node targeting liposome-based nanocarriers. When PEG contents in the bone marrow increased to 7%, targeting efficiency dramatically changes. Lymph node accumulation increases from 6.9% to 14.9% ID/g and bone marrow accumulation decreased from 14.2% ID/g to 2.4% ID/g.

FIG. 7 shows biodistribution of lymph node targeting liposome-based carriers. When PEG contents in the bone marrow increased to 7%, targeting efficiency dramatically changes. Lymph node accumulation increases from 6.9% ID/g to 14.9% ID/g and bone marrow accumulation decreased from 14.2% ID/g to 2.4% ID/g.

Figure 8B:
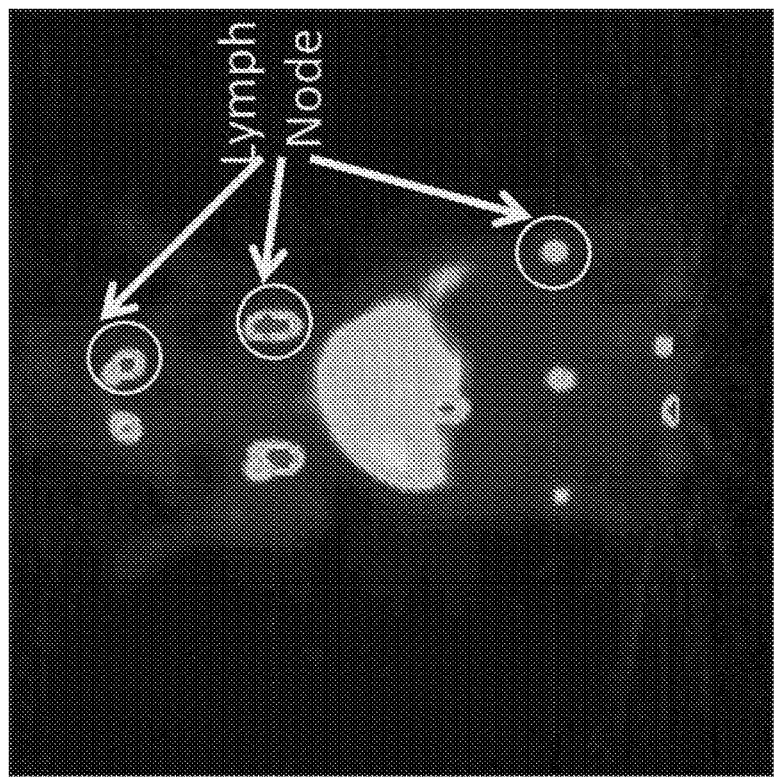
FIGS. 8A and 8B show PET images of accumulation of bone marrow targeting liposomes (FIG. 8A) and lymph node targeting liposomes (FIG. 8B).
Figure 8A:
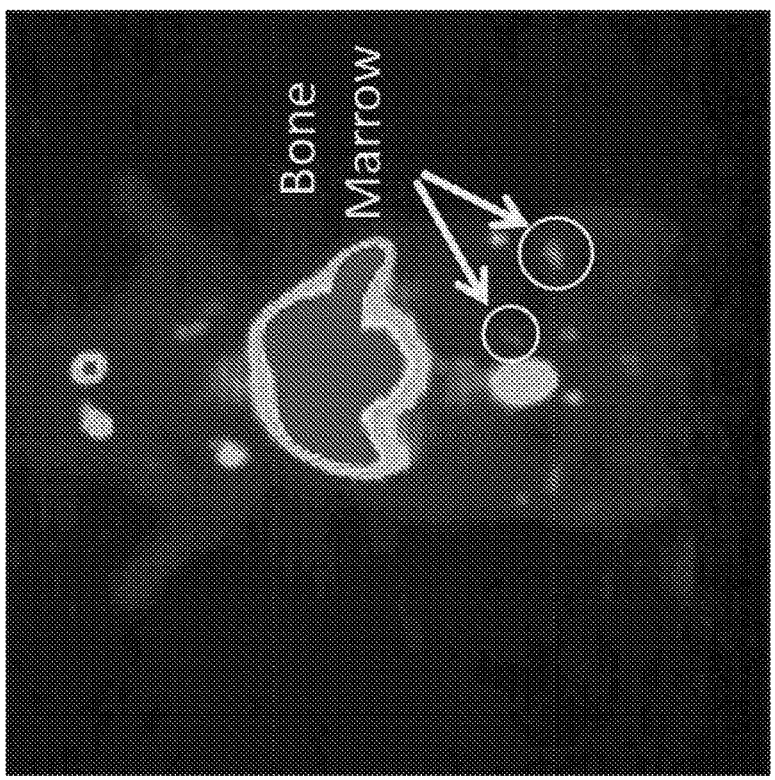

FIGS. 8A and 8B show PET images of the accumulation of bone marrow targeting liposome-based nanocarriers (FIG. 8A) and lymph node targeting liposome-based nanocarriers (FIG. 8B). FIG. 7 shows biodistribution of the lymph node targeting liposomes. The partial volume effect is large in small sized organs such as lymph nodes. Thus, quantification is underestimated for accumulation of the liposome-based nanocarriers in the mouse lymph node, and actual accumulation is even greater.

Materials

All chemicals were used as received without further purification. Chemicals included: 1,2-distearoyl-sn-glycero-3-phosphocholine (DSPC), 1,2-dioctadecanoyl-sn-glycero-3-phosphoethanolamine (DSPE), 1,2-dipalmitoyl-sn-glycero-3-phosphoethanolamine-N-(succinyl) (Succinyl-DPPE), 1,2-distearoyl-sn-glycero-3-phosphoethanolamine-N-[methoxy(polyethylene glycol)-2000] (mPEG2000-DSPE), these, along with Cholesterol, were purchased from Avanti Polar Lipids (Alabaster, Ala.), p-SCN-Bn-DOTA was purchased from Macrocyclics (Dallas, Tex.), N-acetyl cysteine was acquired from Sigma-Aldrich Corporation (St. Louis, Mo.), 5,5'-dithio-bis-(2-nitrobenzoic acid) was purchased from Thermo Fisher Scientific (Waltham, Mass.), $^{64}$Cu was purchased from Washington University in St. Louis (St. Louis, Mo.), where it was produced with the Washington University School of Medicine Cyclotron (model CS-15; Cyclotron Corp.) by the $^{64}$Ni(p,n)$^{64}$Cu reaction, and purified to yield [$^{64}$Cu]—CuCl$_2$.

Activity measurements were made using a CRC-15R Dose Calibrator (Capintec, Ramsey, N.J.). All solvent and components of buffer solutions were analytical grade. PD10 column was purchased from GE Healthcare Life Science (Pittsburgh, Pa.). Athymic male nude mice were purchased from Harlan Laboratories (Indianapolis, Ind.).

Methods

Synthesis of DOTA-Bn-DSPE

12 µmoles of p-SCN-Bn-DOTA was dissolved in 1 mL of chloroform:methanol:water (65:35:8) mixture and 22 µmoles of DSPE was dissolved in 1 mL of chloroform: methanol:water mixture. After mixing two solutions, 48 µmoles of triethylamine was added. The mixture was stirred at 40° C. for 2 h followed by stirring at room temperature for 16 h. The progress of reaction was monitored using silica gel coated TLC plates using in chloroform/methanol/water (65:35:1) as eluant and product formation was confirmed by mass spectroscopy.

Preparation of Liposomes

Liposomes were composed of DSPC and cholesterol in a molar ratio of 6:4. When necessary, the initial lipid mixture was supplemented with 1 or 2.5% mol of mPEG2000-DSPE and/or 10% succinyl-DPPE. Additional 0.1% mol DOTA-Bn-DSPE was added to all lipid composition for subsequent $^{64}$Cu labeling. All the lipids were dissolved in chloroform and the solvent was evaporated under flowing nitrogen gas at 37° C. while ensuring uniform coating of lipids on the round bottomed flask. Residual solvent was removed under vacuum for at least 2 h. Lipid film was hydrated in PBS at 65° C. for 1 h, with three 30 sec sonications in ultrasonic bath at 20 min intervals. The hydrated lipid film underwent 3 cycles of freeze and thaw. The crude lipid dispersion was extruded 11 times through 0.1 µm or 0.03 µm pore size, Whatman® Polycarbonate Membrane Filter using mini extruder system (Avanti Polar Lipids, Alabaster, Ala.) at 65° C. After extrusion, the liposomes were purified using a PD10 column (GE Life sciences, Marlborough, Mass.) to remove unincorporated liposomal lipids and salts.

Characterization of Liposomes

Liposome size distribution and zeta potential at 25° C. in PBS pH 7.4 were determined by Zetasizer Nano-ZS from Malvern Instruments (Malvern, Worcestershire, UK). Liposome stability under serum was determined after liposome was incubated in 50% FCS in PBS for 24 h. Long-term liposome stability at 4° C. was tested for 1 year by analyzing size distribution.

Radioactive Labeling of Liposome with and $^{64}$Cu

[$^{64}$Cu]—CuCl$_2$ (750 µCi in 0.1 N HCl) was added to 750 µL of 20 µM total lipid concentration liposomes, adjusted to pH 5.5 with 0.2 M sodium acetate buffer. The reaction mixture was stirred at 50° C. for 1 h with constant shaking using an Eppendorf ThermoMixer®. Instant thin layer chromatography (ITLC) was performed on an ITLC-SG paper and using 5 mM DTPA solution (pH 5.5) as eluant to monitor the progress of reaction. Then the liposome was purified on a PD-10 column in PBS to separate unchelated 64-Cu and to adjust the pH to 7.4.

Blood Clearance of $^{64}$Cu Liposome $^{64}$Cu labeled liposomes were injected into athymic nude mice via intravenous injection. A sample of the animal's blood was collected after via the tail vein sampling at different time points and radioactivity was determined in a gamma counter and normalized to weight. Half-lives were calculated using one-phase or two-phase decay equations installed in Prism 6.0 (GraphPad Software Inc, La Jolla, Calif.).

Biodistribution of and $^{64}$Cu Liposome

For biodistribution studies about 140 µCi (5.2 MBq) of $^{64}$Cu labeled liposome was administered into athymic nude mice (n=9) via intravenous through tail vein injection. Mice were sacrificed at 4 or 24 h after injection and major organs were collected and placed in an Eppendorf microcentrifuge tube. To collect bone marrow, the femur was dipped into liquid nitrogen and one of the epiphysis was carefully removed and a 60 mL syringe with gauge 30½ needles were inserted into one end of femur. Air was blown and bone marrow was collected in the same tubes for radioactivity counting. Radioactivity of samples was determined without additional treatment or tissue solubilization in a gamma counter (PerkinElmer, Inc., Waltham, Mass.). Data were presented as percent injected dose per gram (% ID/g) of tissue.

MicroPET and PET/CT Imaging

PET imaging of mice administered with $^{64}$Cu labeled liposomes was performed using either on microPET Focus120 small animal PET scanner (Siemens, Knoxville, Tenn.) or Inveon small animal PET/CT scanner (Siemens, Knoxville, Tenn.). 140 µCi (5.2 MBq) of $^{64}$Cu labeled liposome was injected into athymic nude mice via intravenous injection and images were taken either at 4 h or 24 h after injection. Static scans were acquired for 5 mins, 4 h post injection images or for 20 mins, 24 h post injection images. ASIPro (Siemens Medical Solutions, Knoxville, Tenn.) or Amide (5) software were used to visualize the PET data and generate images.

Dynamic MicroPET Imaging of $^{64}$Cu Labeled Liposome Injected Mouse and Analysis 100 μCi (3.7 MBq) of $^{64}$Cu labeled liposome was injected into athymic nude mice via tail vein using catheters. Liposomes were injected at a constant speed over 3 min after data was collected. Images were collected for first 65 min post administration of the tracers and mice were repositioned and imaged again at 2.5, 3.7, 5, 7.5, 10, 20, 24, and 28 h. Regions of Interest (ROIs) of heart, liver, spleen and sacrum were drawn on the images, and then quantified. Pharmacokinetic parameters were derived and calculated after data were fitted on two compartments models using non-linear curve fitting with user-defined equation in Prism 6.0.

Software and Statistics

Prism 6.0 was used for plotting graph, fitting curve, and statistical analysis. ASIPro VM (Siemens Medical Solutions, Knoxville, Tenn.) and Amide was used for PET and PET/CT image analysis.

Institution Research Animal Approval

All animal experiments were approved by the Institutional Animal Care and Use Committee of Memorial Sloan Kettering Cancer Center under protocol 86-02-020.

Stability of Liposomes

FIGS. 19A-19C show BMT liposome stability. Liposome sizes (FIG. 19A), zeta potential at pH 7.4 (FIG. 19B), and labeling efficiency (FIG. 19C) were measured for 1, 2, 3, 4, 6, and 9 months.

Further, the present example demonstrates that the isotope does not dissociate from the chelator at room temperature and has a sufficient shelf life for at least 24 hours.

Positively Charged Liposomes with Different PEG Contents

Figure 20B:
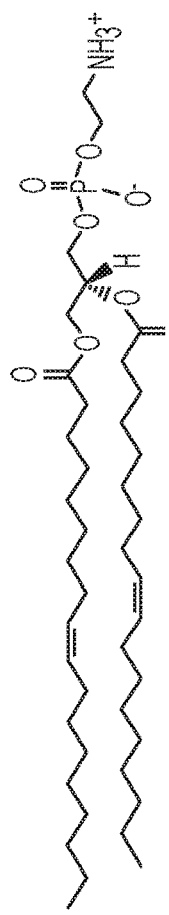
FIGS. 20A-20C show positively charged liposomes with different PEG contents. It was found that BMT liposomes also target lymph nodes. To determine if targeting is liposome formulation specific, positively charged liposomes (FIG. 20A, FIG. 20B) were formulated with different PEG contents.
Figure 20A:
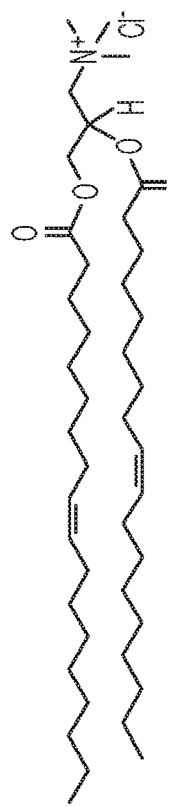

Without wishing to be bound to any theory, it was hypothesized that negative charge and PEG contents may contribute to lymph node targeting. To test this hypothesis, positively charged liposomes containing 1,2-dioleoyl-3-trimethylammonium-propane (DOTAP) and 1,2-dioleoyl-sn-glycero-3-phosphoethanolamine (DOPE) were formulated to deliver DNA or RNA into cells (see Table 5). FIGS. 20A and 20B each show a chemical structure of DOTAP and DOPE.

Table 5 shows the composition ratio (wt. %) of ratio each component (DOPE:DOTAP), where P stands for DOPE and T stands for DOTAP. For example, "P1T3 PEG1" is indicative of a DOPE:DOTAP ratio of 1:3.

TABLE 5

| Name | DOPE:DOTAP ratio | PEG (wt. %) |
|---|---|---|
| P1T3 PEG1 | 1:3 | 1 |
| P1T3 PEG7 | 1:3 | 7 |
| P3T1 PEG1 | 3:1 | 1 |
| P3T1 PEG7 | 3:1 | 7 |

Table 6 shows size (nm), polydispersity index (PDI), zeta potential at pH 7.4 (mV) and $^{64}$Cu labeling of positively charged liposomes with different PEG contents, where P stands for DOPE and T stands for DOTAP. For example, "P1T3 PEG1" is indicative of a DOPE:DOTAP ratio of 1:3.

TABLE 6

| Name | Size (nm) | PDI | Zeta (mV) | 64Cu labeling |
|---|---|---|---|---|
| P1T3 PEG1 | 98 ± 0.4 | 0.07 ± 0.009 | 14.8 ± 0.5 | 40.37 |
| P1T3 PEG7 | 115 ± 1.1 | 0.14 ± 0.012 | 5.5 ± 0.1 | 46.83 |
| P3T1 PEG1 | 106 ± 1.3 | 0.11 ± 0.006 | 4.2 ± 0.3 | — |
| P3T1 PEG7 | 100 ± 0.6 | 0.09 ± 0.005 | 0.8 ± 0.2 | — |

Figure 20C:
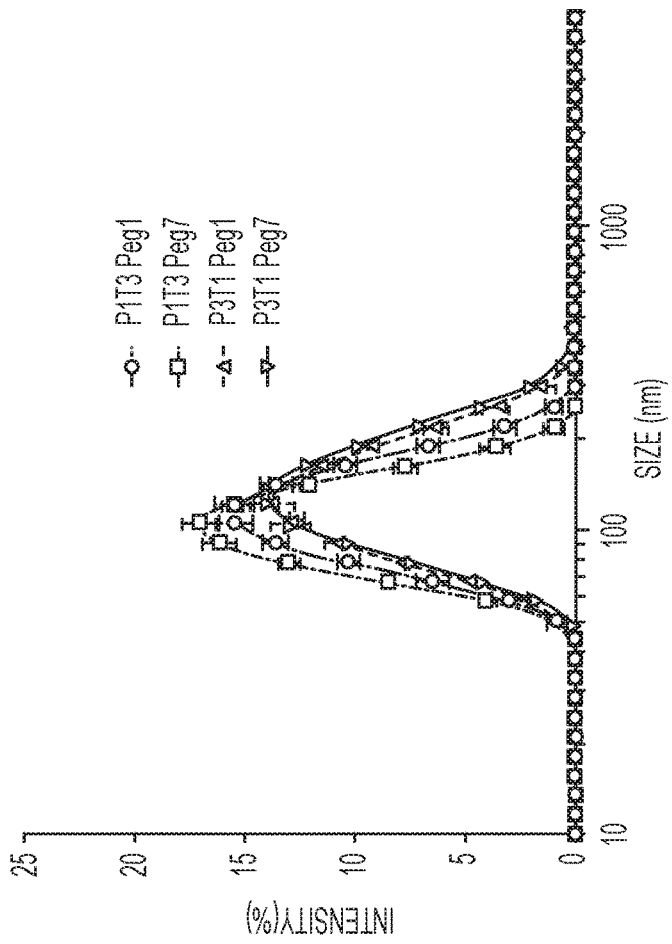

FIG. 20C shows zeta potential at pH 7.4 for positively charged liposomes have different ratios of DOPE:DOTAP. DOPE:DOTAP=3:1 was chosen as its zeta potential at pH 7.4 is 14.8 mV and its absolute value is similar to BMT liposomes having a zeta potential at pH 7.4 of −18.8 mV.

Figure 21:
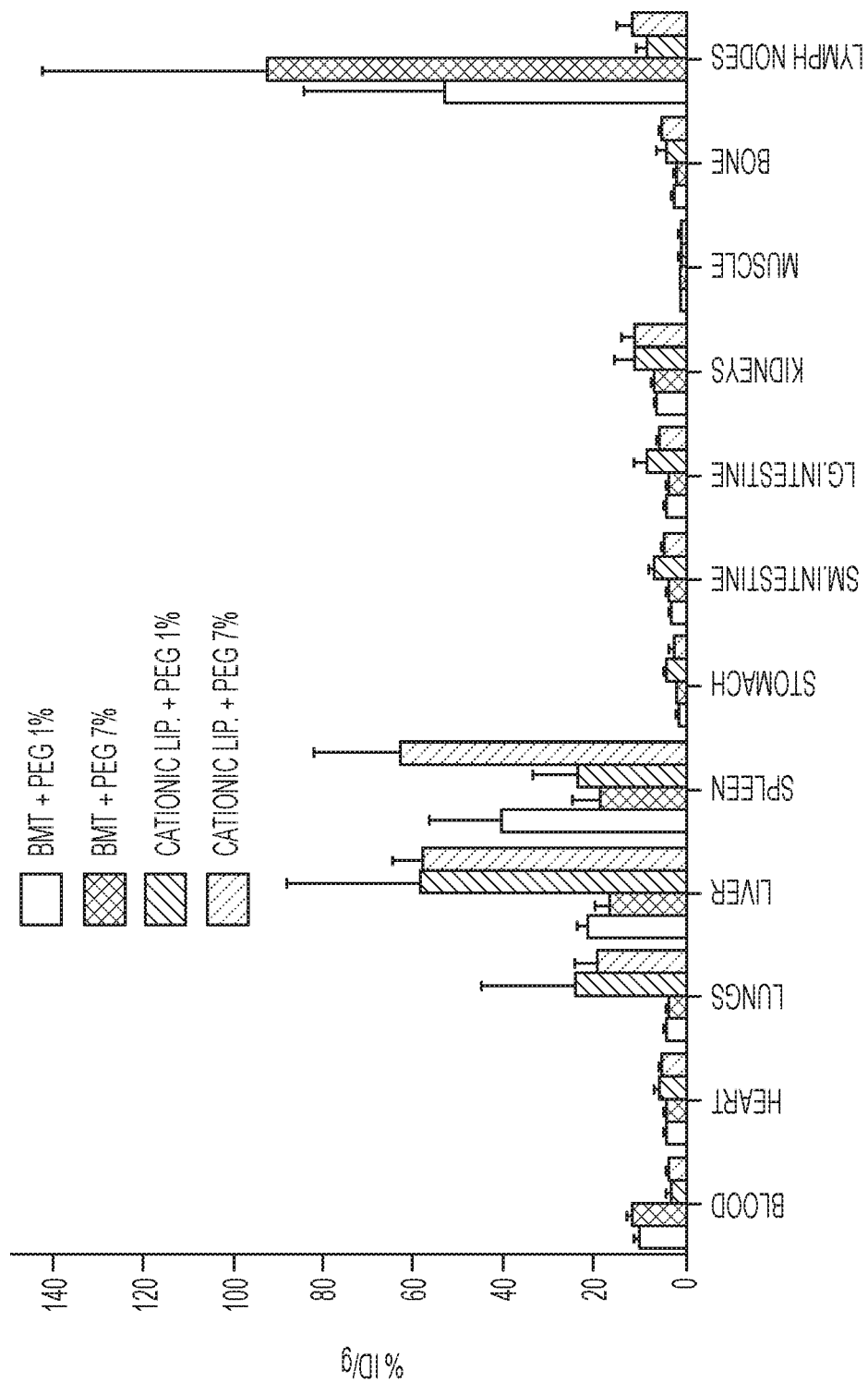
FIG. 21 shows biodistribution of BMT liposomes and positively charged liposomes with different PEG contents. BMT liposomes target the lymph node with 52.9 and 91.8% ID/g at 1 wt. % and 7 wt. % PEG contents while cationic liposomes accumulate in lymph nodes at lower concentrations, 7.8% ID/g and 11.6% ID/g, respectively. BMT liposome formulation with 7 wt. % PEG gives optimal lymph node targeting.
Figure 23B:
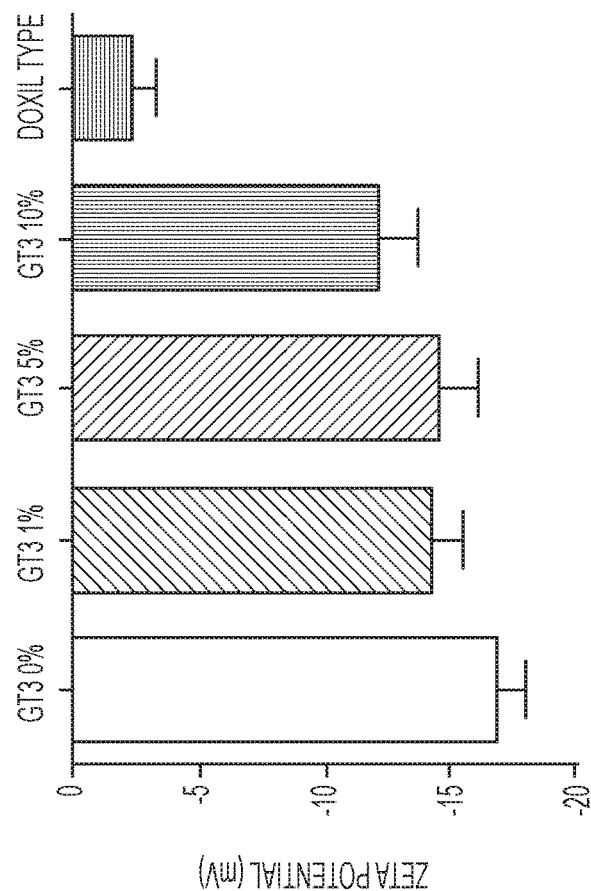
FIGS. 23A and 23B show characterization of radioprotectant GT3 containing BMT liposomes. Size distribution (105±3.5 nm) was similar to BMT liposomes and used the same pore size membrane filter for synthesis (FIG. 23A). Zeta potentials at pH 7.4 are slightly lower than BMT liposomes without GT3 (FIG. 23B).
Figure 23A:
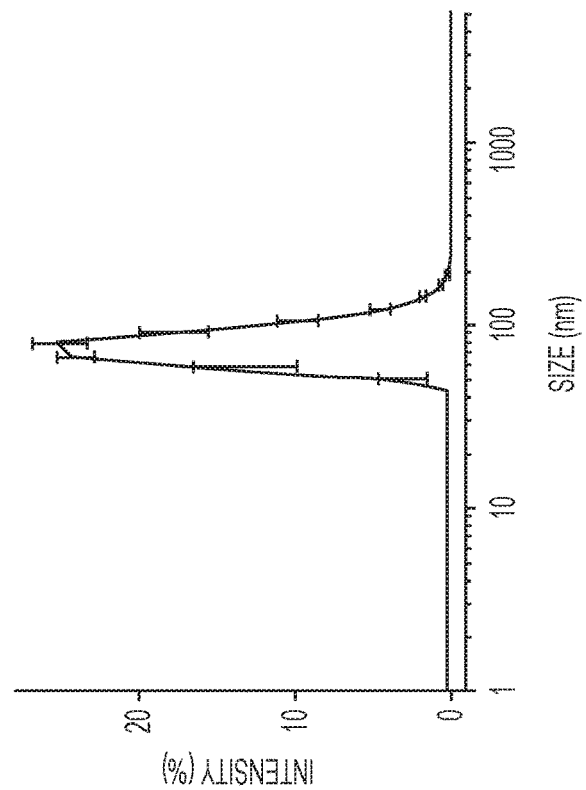
Figure 25:
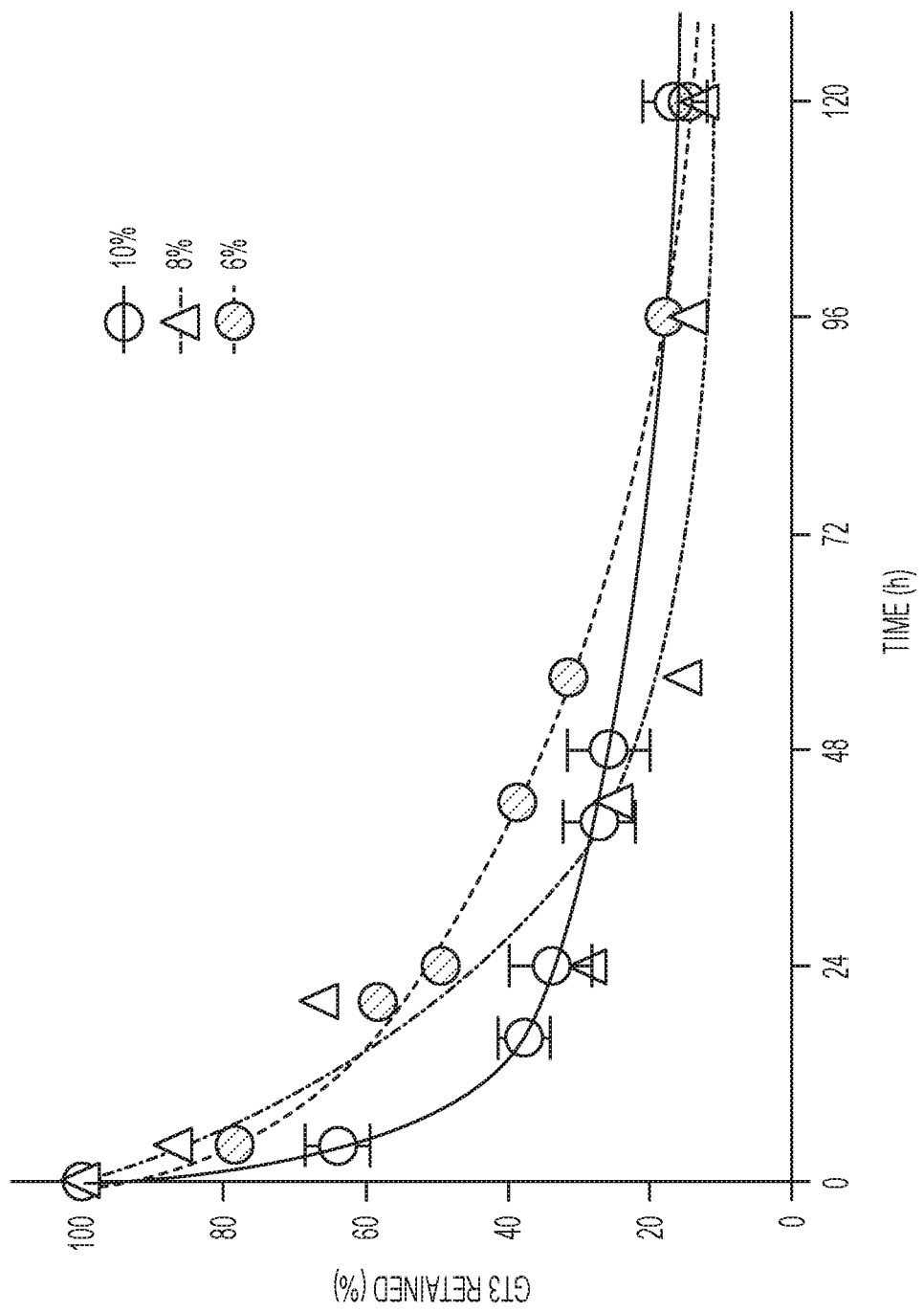
FIG. 25 shows GT3 release from BMT liposomes. 6, 8, and 10 mol % of GT3 were incorporated into BMT liposomes. After $^{131}$I labeling to GT3, GT3 containing BMT liposomes were incubated in 50 k MWCO dialysis bag and radioactivity was counted. The highest GT3 retaining was obtained at 6% GT3 containing liposome at 24 h (or 50% release over 24 hours). Based on the result, 6% GT3 liposome were chosen for further experiments described herein.
Figure 26A:
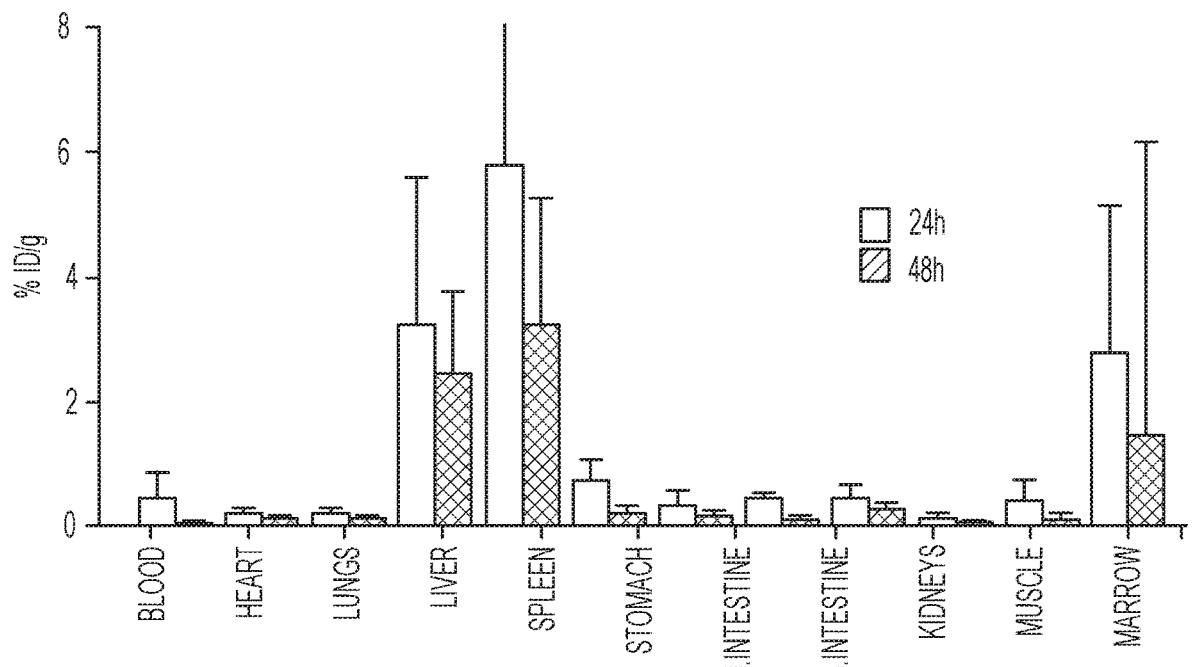
FIGS. 26A and 26B show biodistribution data of GT3 containing liposomes. The biodistribution data shows that GT3 containing liposomes behave similarly to BMT liposomes without GT3.
Figure 26B:
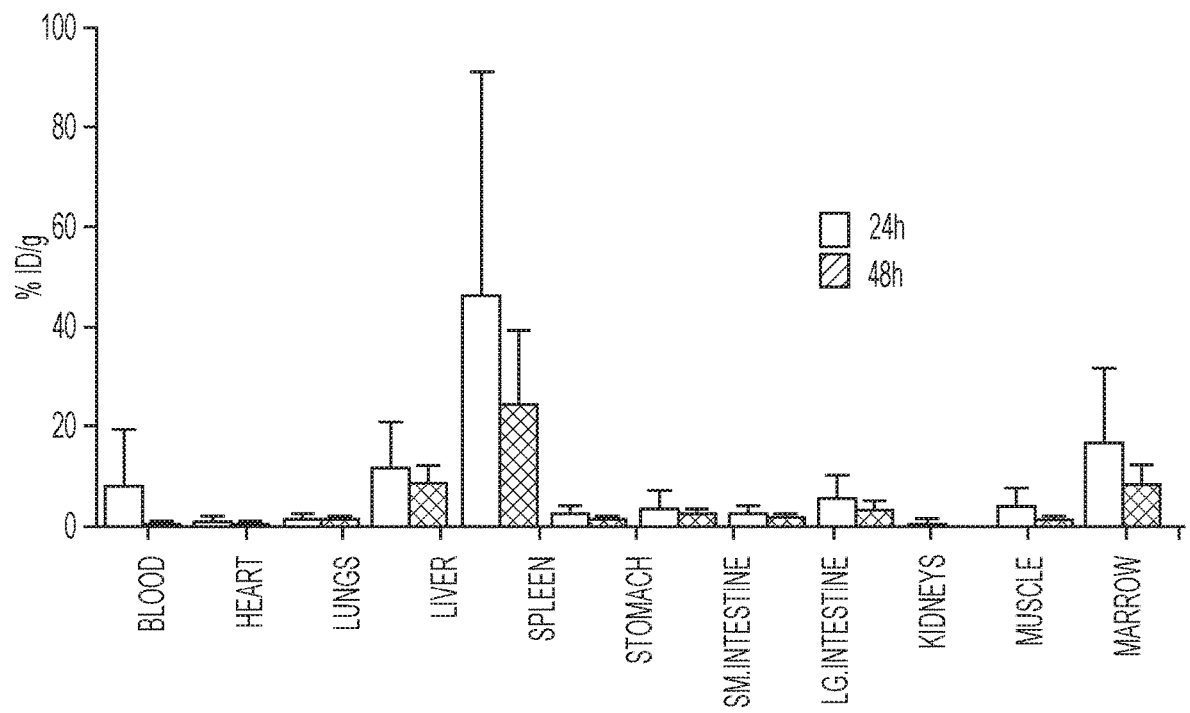
Figure 27B:
FIGS. 27A and 27B show $^{64}$Cu PET/CT images of GT3 containing liposomes at 24 hours.
Figure 27A:
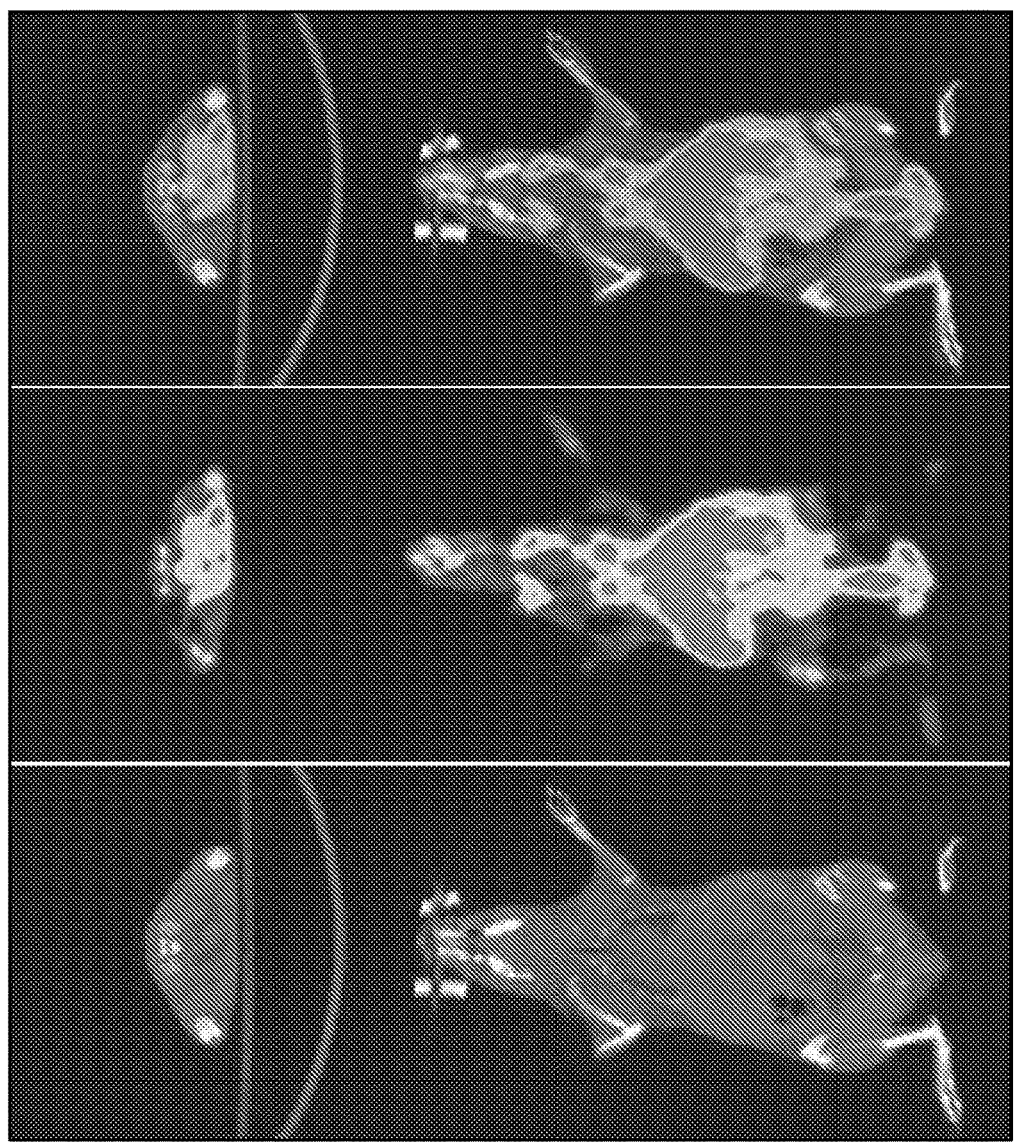

FIG. 21 shows biodistribution of BMT liposomes and positively charged liposomes with different PEG contents. BMT liposomes target the lymph node with 52.9% ID/g and 91.8% ID/g at 1% and 7% PEG contents while cationic liposomes accumulate in lymph nodes at lower concentrations, 7.8% ID/g and 11.6% ID/g, respectively. Accordingly, liposome targeting appears to be influenced by the negative charge of the liposomes.

Blood Cell Counts of GT3 Liposome Treated Mice after Ionizing Radiation

The present example provides how radioprotectant/free radical scavengers, such as GT3, can be delivered via liposomes to bone marrow prior to exposure to radiation.

Figure 28A:
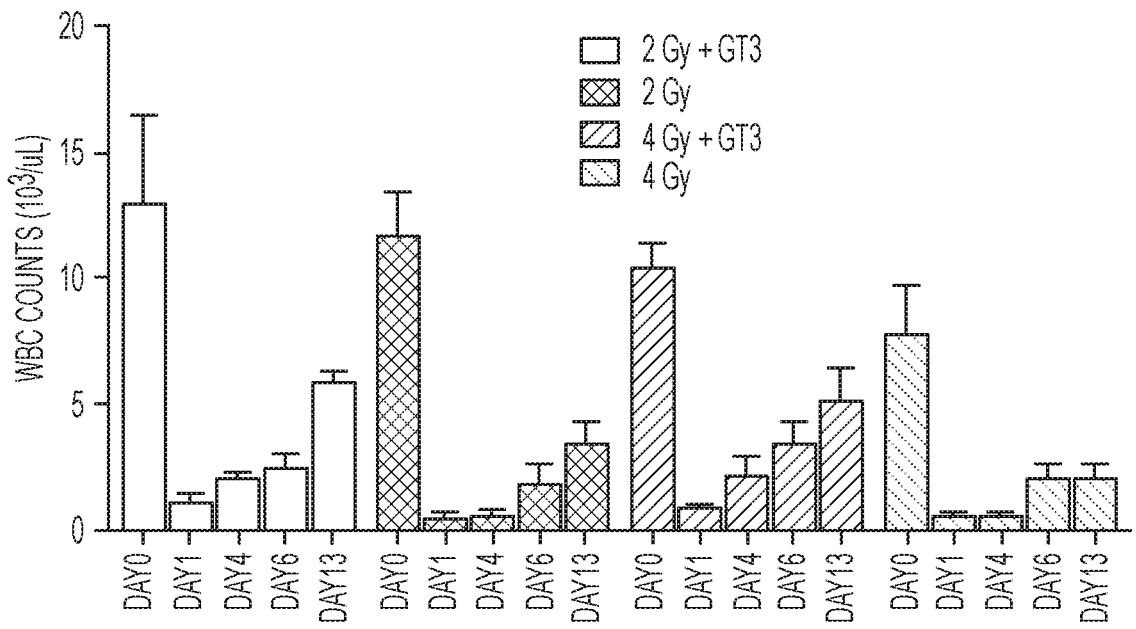
FIGS. 28A and 28B show blood cell counts of GT3 liposome treated mice after ionization radiation. White blood cell (WBC) (FIG. 28A) and lymph (FIG. 28B) counts are shown for mice treated with 2 Gy+GT3 containing liposomes, 2 Gy, 4 Gy+GT3 containing liposomes, and 4 Gy.
Figure 28B:
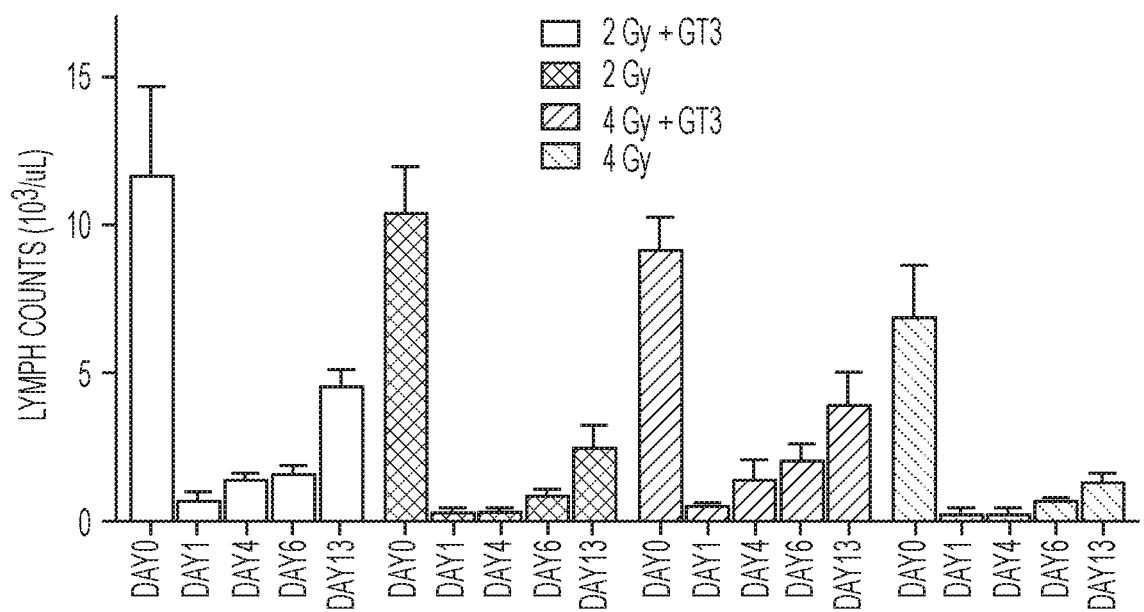
Figure 29:
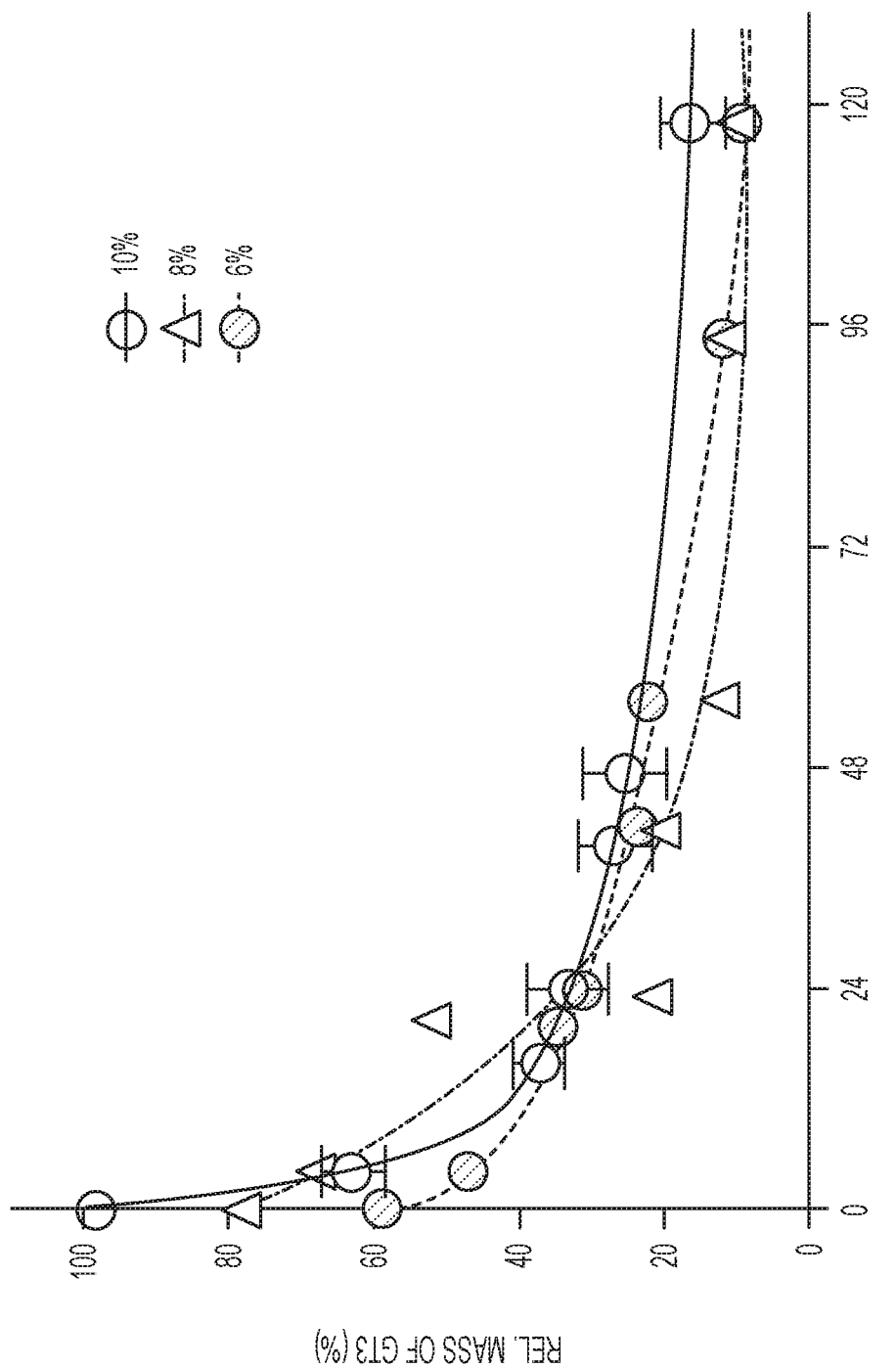
FIG. 29 shows that relative GT3 amounts compared to 10 mol % GT3 liposomes and GT3 contents were similar for 6-10 mol % GT3 liposomes at 24 h post injection.

C57/B6 mice were treated with GT3 containing BMT liposomes with 10 mg/kg GT3 at 24 h prior to 2 and 4 Gy. Blood cells were counted at 0, 1, 4, 6, 13 days after irradiation. As shown in FIGS. 28A and 28B, total white blood counts (WBC) counts recovered faster in GT3 BMT liposome treated group than BMT liposomes without GT3. Lymphocyte recovery is the most significant. Accordingly, after delivery of GT3 containing liposomes and subsequent exposure to 2 or 4 Gy, there was an enhanced rapid recovery effect of lymphocyte and neutrophils. This effect was not seen when GT3 was not targeted to the bone marrow.

What is claimed is:

1. A liposome-based nanocarrier comprising:
    1,2-dipalmitoyl-sn-glycero-3-phosphoethanolamine-N-(succinyl) (succinyl-DPPE);
    an organic polymer comprising polyethylene glycol (PEG), wherein the concentration of PEG is from about 0.5 wt. % to about 10 wt. % of the liposome-based nanocarrier; and
    an associated drug selected from the group consisting of a free radical scavenger or a radioprotectant,
    wherein the liposome-based nanocarrier has a surface having a negative charge due to succinyl-DPPE, and
    wherein the liposome-based nanocarrier selectively targets bone marrow or lymph nodes.

2. The liposome-based nanocarrier of claim 1, wherein the liposome-based nanocarrier comprises a member selected from the group consisting of 1,2-dioleoyl-sn-glycero-3-phosphoethanolamine-N-(succinyl) (succinyl PE), 1,2-distearoyl-sn-glycero-3-phosphocholine (DSPC), cholesterol, and 1,2-distearoyl-sn-glycero-3-phosphoethanolamine (DSPE).

3. The liposome-based nanocarrier of claim 1, wherein the liposome-based nanocarrier comprises a lipid labeled with an isotope and chelator.

4. The liposome-based nanocarrier of claim 3, wherein isotope comprises a member selected from the group consisting of $^{64}$Cu, $^{66}$Ga, $^{86}$Y, $^{111}$In, $^{67}$Ga, $^{68}$Ga, $^{124/131}$I, and $^{177}$Lu.

5. The liposome-based nanocarrier of claim 3, wherein the chelator comprises a member selected from the group consisting of 1,4,7,10-tetraazacyclododecane-1,4,7,10-tetraacetic acid (DOTA) and 1,4,7-triazacyclononane-1,4,7-trisacetic acid (NOTA).

6. The liposome-based nanocarrier of claim 3, wherein the chelator comprises a member selected from the group consisting of DOTA-Bn-DSPE and NOTA-Bn-DSPE.

7. The liposome-based nanocarrier of claim 1, wherein the liposome-based nanocarrier comprises 1,2-distearoyl-sn-glycero-3-phosphoethanolamine-N-methoxy(polyethylene glycol) (mPEG-DSPE).

8. The liposome-based nanocarrier of claim 1, wherein the liposome-based nanocarrier is at least 3 mole % lipid.

9. The liposome-based nanocarrier of claim 1, wherein the liposome-based nanocarrier has an average diameter in a range from 30 nm to 300 nm.

10. The liposome-based nanocarrier of claim 1, wherein the liposome-based nanocarrier is from one or more of (i), (ii), and (iii), as follows:
(i) from 3 to 20 wt. % succinyl DPPE;
(ii) from 0.5 to 2 wt. % PEG; and
(iii) from 5 to 9 wt. % PEG.

11. The liposome-based nanocarrier of claim 1, wherein the negative charge of the surface of the liposome-based nanocarrier is from −15 mV to −25 mV.

12. A method for imaging a subject the method comprising:
administering to the subject a liposome-based nanocarrier of claim 1, wherein the liposome-based nanocarrier comprises a lipid labeled with an isotope and a chelator.

13. The method of claim 12, further comprising obtaining and displaying a positron emission tomography (PET) and/or Positron emission tomography—computed tomography (PET/CT) image of at least one tissue of the subject comprising the liposome-based nanocarrier.

14. The method of claim 12, further comprising quantitatively measuring a distribution of the liposome-based nanocarrier in at least one tissue of the subject.

15. The method of claim 14, the method comprising quantitatively measuring the distribution of the liposome-based nanocarrier in an organ of the reticuloendothelial system.

16. The method of claim 15, wherein the organ comprises a member selected from the group consisting of liver, spleen, and bone marrow.

17. The method of claim 15, comprising determining a concentration and/or total amount of delivered radiolabeled drug in the tissue based on a positron emission tomography (PET) or Positron Emission Tomography—Computed Tomography (PET/CT) image of the tissue.

18. The method of claim 14, the method comprising quantitatively measuring the distribution of the liposome-based nanocarrier in one or more lymph nodes.

19. The method of claim 12, wherein the administered liposome-based nanocarrier demonstrates selective targeting of bone marrow of the subject such that concentration of the liposome-based nanocarrier in bone marrow is at least 3 fold greater than the concentration of the liposome-based nanocarrier in any of the tumor tissue at a given time following administration of the liposome-based nanocarrier, wherein the given time is at least 1 hour following administration.

20. The method of claim 12, further comprising capturing and displaying a sequence of PET images in real time.

21. A method of treating a subject, the method comprising administering the liposome-based nanocarrier of claim 1 to the subject suffering from or susceptible to a disease and/or condition.

22. The method of claim 21, wherein the disease and/or condition comprises a member selected from the group consisting of bone marrow suppression (BMS), myelodysplastic syndrome (MDS), acute myeloid leukemia (AML), chronic myeloid leukemia (CML), sepsis, graft-versus-host-disease (GVHD), bone metastasis, and osteoporosis.

23. The method of claim 21, wherein the disease and/or condition comprises exposure to radiation.

24. The method of claim 22, the method further comprising after administering the liposome-based nanocarrier, administering a chemotherapeutic and/or radiation therapy.

25. The method of claim 21, wherein the administered liposome-based nanocarrier demonstrates selective targeting of bone marrow of the subject such that the concentration of the liposome-based nanocarrier in bone marrow is at least 3 fold greater than the concentration of the liposome-based nanocarrier in any of the tumor tissue at a given time following administration of the liposome-based nanocarrier,
wherein the given time is at least 1 hour, following administration.

26. A method of monitoring a patient, the method comprising
administering the liposome-based nanocarrier of claim 1 to a patient suffering from or susceptible to a disease and/or condition; and
investigating a quantity of drug delivered to at least one tissue of the patient.

27. A method of imaging an organ of the reticuloendothelial system in a subject, the method comprising:
detecting radiation from the liposome-based nanocarrier of claim 1, the subject having been administered the liposome-based nanocarrier.

28. The method of claim 27, wherein the radiation is detected via an external PET imaging system.

29. The method of claim 27, wherein the organ comprises a member selected from the group consisting of active bone marrow, liver, and spleen.

30. The method of claim 27, the method further comprising displaying an image corresponding to the detected radiation, the image visually distinguishing active bone marrow from other tissue and, optionally, quantifying the concentration of drug and/or liposome based nanocarrier.

31. The liposome-based nanocarrier of claim 1, wherein the liposome-based nanocarrier has an average diameter in a range from 50 nm to 200 nm.

32. The liposome-based nanocarrier of claim 1, wherein the liposome-based nanocarrier comprises a radiolabel.

33. The liposome-based nanocarrier of claim 1, wherein the nanocarrier is from 0.5 wt. % to 2 wt. % PEG and wherein the liposome-based nanocarrier selectively targets bone marrow.

34. The liposome-based nanocarrier of claim 1, wherein the nanocarrier is from 5 wt. % to 9 wt. % PEG and wherein the liposome-based nanocarrier selectively targets lymph nodes.

* * * * *